United States Patent
Gerster et al.

(10) Patent No.: US 8,119,710 B2
(45) Date of Patent: Feb. 21, 2012

(54) FILLED RUBBER COMPOUNDS WITH IMPROVED PROCESSABILITY

(75) Inventors: Michèle Gerster, Binningen (CH); Gerrit Knobloch, Magden (CH); Pierre Rota-Graziosi, Mulhouse (FR); Francesco Fuso, Therwil (CH)

(73) Assignee: BASF SE, Ludwigshafen (DE)

( * ) Notice: Subject to any disclaimer, the term of this patent is extended or adjusted under 35 U.S.C. 154(b) by 750 days.

(21) Appl. No.: 11/991,813

(22) PCT Filed: Sep. 12, 2006

(86) PCT No.: PCT/EP2006/066261
§ 371 (c)(1),
(2), (4) Date: Mar. 11, 2008

(87) PCT Pub. No.: WO2007/039416
PCT Pub. Date: Apr. 12, 2007

(65) Prior Publication Data
US 2010/0317778 A1    Dec. 16, 2010

(30) Foreign Application Priority Data
Sep. 21, 2005 (EP) .................................... 05108706

(51) Int. Cl.
*C08K 5/5393* (2006.01)
*C08L 23/26* (2006.01)

(52) U.S. Cl. ........ 524/133; 524/580; 524/430; 524/384; 524/186; 524/147; 556/427; 556/428

(58) Field of Classification Search .................. 524/133, 524/580, 430, 384, 186, 147; 556/427, 428
See application file for complete search history.

(56) References Cited

U.S. PATENT DOCUMENTS

| | | | |
|---|---|---|---|
| 3,478,077 A | 11/1969 | Wu | 260/448.2 |
| 3,483,241 A | 12/1969 | Berger | 260/448.2 |
| 5,227,425 A | 7/1993 | Rauline | 524/493 |
| 6,313,205 B1 * | 11/2001 | Chiron et al. | 524/262 |
| 6,414,061 B1 | 7/2002 | Cruse et al. | 524/262 |
| 2003/0229166 A1 | 12/2003 | Krafczyk et al. | 524/261 |
| 2004/0210001 A1 | 10/2004 | Cruse et al. | 525/100 |

FOREIGN PATENT DOCUMENTS

| | | |
|---|---|---|
| EP | 0014599 | 8/1980 |
| WO | 02/081432 | 10/2002 |
| WO | 2005/059022 | 6/2005 |

OTHER PUBLICATIONS

I. Still et al., Heteroatom Chemistry, vol. 5, No. 3, (1994) pp. 251-257.
S. Nakamura et al., J. Org. Chem., vol. 65, (2000), pp. 469-474.
A. Schwan et al., Tetrahedron: Asymmetry, vol. 6, No. (1995), pp. 131-138.
E. Phillips et al., Tetrahedron Letters, vol. 34, No. 15, (1993), pp. 2537-2540.
A. Schwan et al., Can. J. Chem., vol. 72, No. 2, pp. 325-333 (1994).
A. Schwan et al., Eur. J. Org. Chem., (2001), pp. 1643-1654.
Chem. Abstr. 1997:462211 for Y. Yamashita et al., Shikizai Kyokaishi, vol. 70, No. 5, (1997), pp. 300-307.
Chem. Abstr. 1978:61890 for K. S. Mingaleva et al., Zhurnal Obshchei Khimii, vol. 47, No. 10, (1977), pp. 2278-2284.
Chem. Abstr. 1977:43771 for M. M. Tanaskov et al., Zhurnal Obshchei Khimii, vol. 46, No. 9, (1976), pp. 2058-2065.
Chem. Abstr. 1975:479320 for M. M. Tanaskov et al., Zhurnal Obshchei Khimii, vol. 45, No. 4, (1975), pp. 843-854.
Chem. Abstr. 1966:456888 for K. A. Andrianov et al., Zhurnal Obshchei Khimii, vol. 36, No. 5, (1966), pp. 895-900.

* cited by examiner

*Primary Examiner* — Robert D. Harlan
(74) *Attorney, Agent, or Firm* — Tyler A. Stevenson

(57) ABSTRACT

The invention describes a process for the manufacture of a filled rubber compound with improved processability which comprises mixing in one-step a) a rubber, b) a white reinforcing filler, and c) a coupling agent of the Formula (I), wherein the general symbols are as defined in claim 1, or an oligomeric hydrolysis product of the compound of the Formula (I).

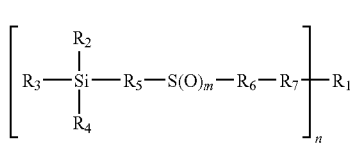

19 Claims, No Drawings

FILLED RUBBER COMPOUNDS WITH IMPROVED PROCESSABILITY

The present invention relates to a process for the manufacture of a filled rubber compound with improved processability (decrease of Mooney viscosity) which comprises mixing in one-step (a) a rubber, (b) a white reinforcing filler, and (c) as coupling agent at least a thio substituted silane or an oligomeric hydrolysis product thereof; to new sulfoxide or sulfone coupling agents; and to compositions comprising an elastomer, e.g. a rubber, susceptible to oxidative, thermal, dynamic or light-and/or ozone-induced degradation, a white reinforcing filler and a new sulfoxide or sulfone coupling agent. The rubber compositions are particularly useful for tread application in vehicle tires.

The tire industry has experienced a milestone development in the late nineties with the discovery by the European tire manufacturer Michelin of the beneficial use of silica as reinforcing white filler in tread tires [see e.g. U.S. Pat. No. 5,227,425]. Indeed, tires with silica-filled tread formulations offer performance advantages over those based on conventional carbon black filler. They also show an improved balance between rolling resistance (reduced fuel consumption) and abrasion resistance versus wet grip (improved driving safety on wet roads).

Because particle surfaces of precipitated silica have hydrophilic silanol groups, which results in strong filler-filler interaction through hydrogen bonds, their affinity to the unpolar rubber matrix is limited and their dispersion in rubber compounds is much worse than of carbon black. In order to improve the compatibility of silica in rubber and ensure its good dispersion within the polymer matrix and to improve the reinforcement effect, coupling agents are necessary to be used.

Silane-based coupling agents used in the rubber industry are usually bifunctional organosilanes, such as bis(3-triethoxysilylpropyl)tetrasulfide (TESPT; or Si 69 from Degussa), bis(3-triethoxysilylpropyl)disulfide (TESPD; or Si 75 from Degussa). Typically, these bis-organosilanes are used to enhance the rubber reinforcement characteristics of silica by reacting with both the silica surface and the rubber elastomer molecules. The critical part of these systems is to maintain control for these two reactions to occur when desired and not before. It is indeed well known that TESPT, with its heat-sensitive tetrasulfide moiety, is a scorchy compound which can induce premature vulcanisation (pre-scorch) if a well controlled complicated multi-step mixing process is not applied. With TESPD, which has a more stable two sulfur atoms bridge in the silane, the premature crosslinking to rubber during compounding also tends to occur but at higher mixing temperatures or at longer times at a lower temperature. The premature cure reaction effects of the silane-rubber reaction are not desirable in rubber processing but cannot totally be avoided with the state-of-the-art coupling agents. Therefore there is a need to develop coupling agents with higher processing safety so that the disadvantageous multi-step mixing process could be simplified and reduced mix times or fewer mix passes applied.

U.S. Pat. No. 6,414,061 discloses blocked mercaptosilanes as coupling agents in mineral filled elastomer compositions. Of special interest is 3-octanoylthio-1-propyltriethoxysilane (NXT Silane from Crompton OSi Specialities). These compounds are indicated as presenting reduced reactivity towards coupling to the polymer during the compounding mixing step but their subsequent coupling to the polymer need to be triggered by the addition of an appropriate deblocking agent.

WO-A-2005/059022 discloses coupling agents for silica in rubber. These coupling agents are added to the rubber and the silica in a multi-step process.

The superior processability of the rubber compound is a highly sought parameter to fulfill in order to enlarge the processing window for mixing ingredients of the rubber compound.

It would therefore be desirable to provide a silica-filled rubber composition with good processability by employing a coupling agent with a larger processing window safety which will remain inert towards the polymer matrix during compounding so that fewer mixing passes, higher processing temperatures or reduced mixing times could be applied. This would result to opportunities for major cost savings and reduce productivity constraints.

It has now been found that a specific group of thio substituted silanes or oligomeric hydrolysis products thereof are particularly suitable as coupling agents for ensuring the coupling of a white reinforcing filler with a rubber in one-step. These coupling agents with their enlarged processing window and high thermal stability can be mixed in a one-step process and/or at higher temperature which advantagely helps shorten processing time and/or decrease of VOC emission without undesirable premature coupling to the rubber.

The present invention therefore provides a process for the manufacture of a filled rubber compound with improved processability which comprises mixing in one-step a) a rubber,
b) a white reinforcing filler, and
c) a coupling agent of the formula I

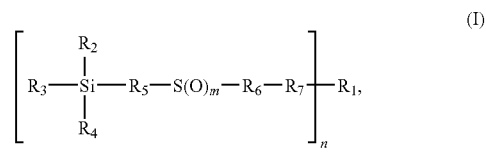

wherein, when n is 1, $R_1$ is hydrogen, $C_1$-$C_{25}$alkyl, $C_1$-$C_{25}$alkyl substituted with furyl, morpholine, $C_1$-$C_4$dialkylamino, $C_1$-$C_4$trialkylammonium or $M^+$ $^-O_3S$—; $C_2$-$C_{25}$alkyl interrupted by oxygen; $C_5$-$C_{12}$cycloalkyl, $C_2$-$C_{25}$alkenyl, unsubstituted or $C_1$-$C_4$alkyl-substituted phenyl; $C_7$-$C_{12}$phenoxyalkyl, unsubstituted or $C_1$-$C_4$alkyl substituted $C_7$-$C_9$bicycloalkyl;

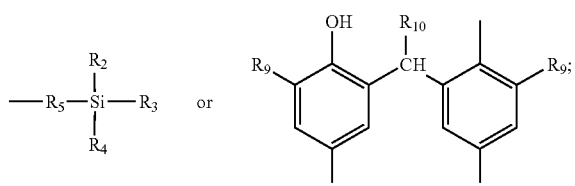

or when $R_7$ is a direct bond, $R_1$ is —CN, —$SOR_8$, —$SO_2R_8$, —$NO_2$ or —$COR_8$; or when $R_6$ and $R_7$ are both a direct bond, $R_1$ is

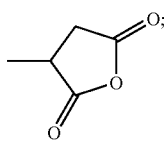

when n is 2,

R₁ is $C_1$-$C_{25}$alkylene, $C_1$-$C_{25}$alkylene substituted with $C_1$-$C_4$alkyl; $C_2$-$C_{25}$alkylene substituted with $C_1$-$C_4$alkyl and interrupted by oxygen; $C_2$-$C_{25}$alkylene interrupted by oxygen, sulfur, phenylene or cyclohexylene;

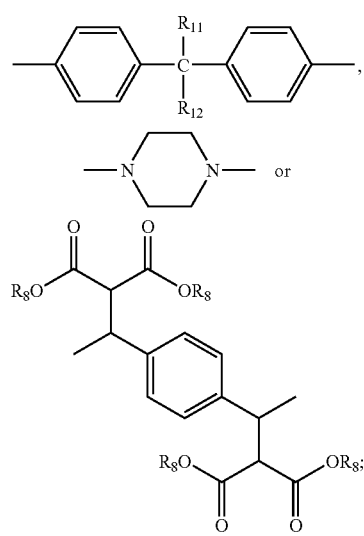

or when $R_6$ and $R_7$ are a direct bond, $R_1$ is

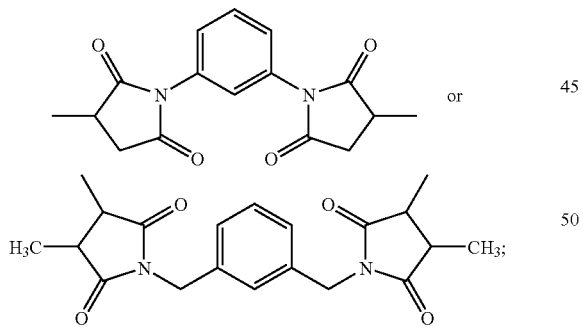

$R_2$, $R_3$ and $R_4$ are each independently of the others $C_1$-$C_{25}$alkyl, $C_2$-$C_{25}$alkyl interrupted by oxygen; $C_5$-$C_{12}$cycloalkyl, $C_2$-$C_{25}$alkenyl, unsubstituted or $C_1$-$C_4$alkyl-substituted phenyl, $C_7$-$C_9$phenylalkyl, $C_1$-$C_{25}$alkoxy, $C_3$-$C_{25}$alkoxy interrupted by oxygen; $C_5$-$C_{12}$cycloalkoxy, $C_2$-$C_{25}$alkenyloxy, unsubstituted or $C_1$-$C_4$alkyl-substituted phenoxy, $C_7$-$C_9$phenylalkoxy, halogen, $C_2$-$C_{25}$alkanoyloxy or unsubstituted or $C_1$-$C_4$alkyl substituted benzoyloxy; or at least two of $R_2$, $R_3$ and $R_4$ are —O—$R_{15}$—O—; or $R_2$ is additionally

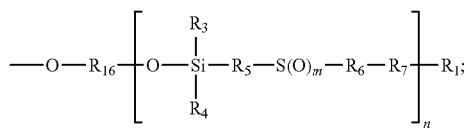

or $R_3$ is additionally

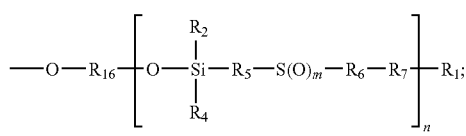

or $R_4$ is additionally

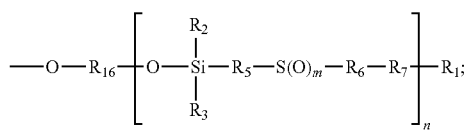

with the proviso that at least one of
$R_2$, $R_3$ or $R_4$ is $C_1$-$C_{25}$alkoxy, $C_3$-$C_{25}$alkoxy interrupted by oxygen; $C_5$-$C_{12}$cycloalkoxy, $C_2$-$C_{25}$alkenyloxy, unsubstituted or $C_1$-$C_4$alkyl-substituted phenoxy, $C_7$-$C_9$phenylalkoxy, halogen, $C_2$-$C_{25}$alkanoyloxy or unsubstituted or $C_1$-$C_4$alkyl substituted benzoyloxy;
$R_5$ is $C_1$-$C_{25}$alkylene, $C_5$-$C_{12}$cycloalkylene, unsubstituted or $C_1$-$C_4$alkyl substituted phenylene;
$R_6$ is a direct bond, $C_1$-$C_{25}$alkylene; or $C_1$-$C_{25}$alkylene substituted with $C_1$-$C_{25}$alkyl, $C_2$-$C_{25}$alkoxycarbonyl, $C_3$-$C_{25}$alkoxycarbonylalkyl or phenyl;
$R_7$ is a direct bond or

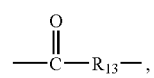

with the proviso that, when $R_7$ is a direct bond and n is 1, $R_6$ is not a direct bond; and with the proviso that, when $R_7$ is

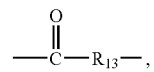

$R_6$ is not a direct bond;
$R_8$ is $C_1$-$C_{25}$alkyl, $C_2$-$C_{25}$alkyl interrupted by oxygen; $C_5$-$C_{12}$cycloalkyl, $C_2$-$C_{25}$alkenyl, $C_2$-$C_{25}$alkinyl, $C_7$-$C_9$phenylalkyl, unsubstituted or $C_1$-$C_4$alkyl-substituted phenyl,
$R_9$ is $C_1$-$C_5$alkyl,
$R_{10}$ is hydrogen or $C_1$-$C_4$alkyl,
$R_{11}$ and $R_{12}$ are each independently of the other hydrogen, $CF_3$, $C_1$-$C_{12}$alkyl or phenyl, or $R_{11}$ and $R_{12}$, together with the carbon atom to which they are bonded, form a $C_5$-$C_8$cycloalkylidene ring that is unsubstituted or substituted by from 1 to 3 $C_1$-$C_4$alkyl groups, $R_{13}$ is oxygen or $-N(R_{14})-$, $R_{14}$ is hydrogen or $C_1$-$C_{12}$alkyl, $R_{15}$ is $C_1$-$C_{25}$alkylene or $C_1$-$C_{25}$alkylene substituted with $C_1$-$C_{25}$alkyl;

$R_{16}$ is $C_1$-$C_{25}$alkylene or $C_1$-$C_{25}$alkylene substituted with $C_1$-$C_{25}$alkyl;

M is sodium, potassium or ammonium, m is 0, 1 or 2, and n is 1 or 2; or an oligomeric hydrolysis product of the compound of the formula I.

Oligomeric hydrolysis products of the compounds of the formula I are those in which at least one of the radicals at the silicium atom ($R_2$, $R_3$ or $R_4$) is replaced by an OH group.

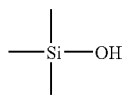

groups can then easily condensate with, for example, another

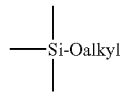

group to form oligomeric compounds. Such condensates or oligomeric hydrolysis products are therefore for example

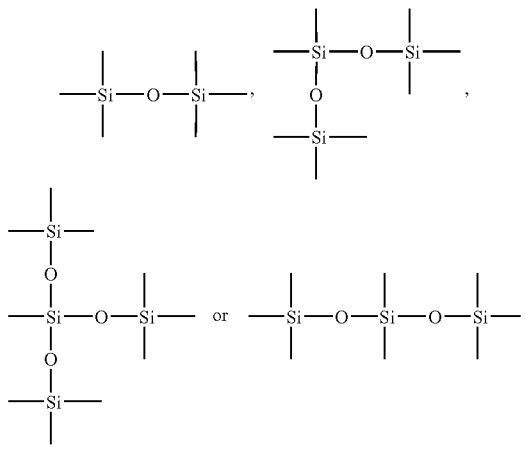

Alkyl having up to 25 carbon atoms is a branched or unbranched radical, such as methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl or eicosyl.

$C_1$-$C_{25}$Alkyl substituted with furyl, morpholine, $C_1$-$C_4$dialkylamino, $C_1$-$C_4$trialkylammonium or $M^+$ $^-O_3S-$ is a branched or unbranched radical, such as furylmethyl, furylethyl, furylpropyl, 2,4-difuryl-hexyl, N-morpholinylethyl, N-morpholinylbutyl, N-morphlinylhexyl, 3—dimethylaminopropyl, 4-dimethylaminobutyl, 5-dimethylaminopentyl, 6-diethylaminohexyl, trimethylammoniumpropyl or potassium sulfoxylpropyl.

$C_2$-$C_{18}$Alkyl interrupted by oxygen is, for example, $CH_3-O-CH_2CH_2-$, $CH_3-O-CH_2CH_2-O-CH_2CH_2-$, $CH_3-(O-CH_2CH_2-)_2O-CH_2CH_2-$, $CH_3-(O-CH_2CH_2-)_3O-CH_2CH_2-$ or $CH_3-(O-CH_2CH_2-)_4O-CH_2CH_2-$.

Alkenyl having 2 to 25 carbon atoms is a branched or unbranched radical such as, for example, vinyl, propenyl, 2-butenyl, 3-butenyl, isobutenyl, n-2,4-pentadienyl, 3-methyl-2-butenyl, n-2-octenyl, n-2-dodecenyl, iso-dodecenyl, oleyl, n-2-octadecenyl or n-4-octadecenyl.

$C_1$-$C_4$Alkyl-substituted phenyl, which contains preferably from 1 to 3, especially 1 or 2, alkyl groups, is, for example, o-, m-or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl.

$C_7$-$C_{12}$Phenoxyalkyl is, for example, phenoxymethyl, phenoxyethyl, phenoxypropyl, phenoxybutyl, phenoxypentyl, or phenoxyhexyl.

$C_7$-$C_8$Bicycloalkylene is, for example, bicycloheptylene or bicyclooctylene $C_1$-$C_4$Alkyl substituted $C_7$-$C_9$bicycloalkyl is, for example,

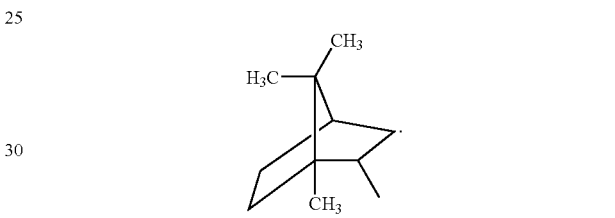

$C_1$-$C_{25}$Alkylene or $C_1$-$C_{25}$alkylene substituted with $C_1$-$C_4$alkyl containing preferably from 1 to 3, especially 1 or 2, branched or unbranched alkyl group radicals, is a branched or unbranched radical, for example methylene, ethylene, propylene, trimethylene, tetramethylene, pentamethylene, hexamethylene, heptamethylene, octamethylene, decamethylene, dodecamethylene, octadecamethylene, 1-methylethylene or 2-methylethylene.

$C_2$-$C_{25}$Alkylene substituted with $C_1$-$C_4$alkyl and interrupted by oxygen is, for example, $-CH_2CH_2-O-CH_2C(CH_3)_2CH_2-O-CH_2CH_2-$.

$C_2$-$C_{25}$Alkylene interrupted by oxygen, sulfur, phenylene or cyclohexylene is, for example, $-CH_2-O-CH_2-$, $-CH_2CH_2-O-CH_2CH_2-$, $-CH_2CH_2-S-CH_2CH_2-$, $-CH_2-O-CH_2CH_2-O-CH_2-$, $-CH_2CH_2-O-CH_2CH_2-O-CH_2CH_2-$, $-CH_2-(O-CH_2CH_2-)_2O-CH_2-$, $-CH_2CH_2-(O-CH_2CH_2-)_2O-CH_2CH_2-$, $-CH_2-(O-CH_2CH_2-)_3O-CH_2-$, $-CH_2-(O-CH_2CH_2-)_4O-CH_2-$, $-CH_2CH_2-(O-CH_2CH_2-)_4O-CH_2CH_2-$, $-CH_2CH_2-O-CH_2C(CH_3)_2CH_2-O-CH_2CH_2-$

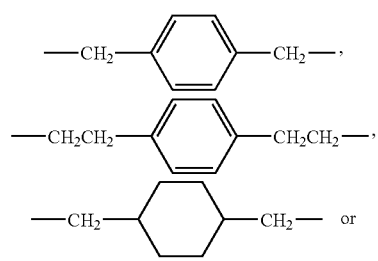

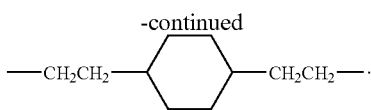

$C_5$-$C_{12}$Cycloalkyl is, for example, cyclopentyl, cyclohexyl, cycloheptyl or cyclooctyl. Preference is given to cyclohexyl.

$C_7$-$C_9$Phenylalkyl is, for example, benzyl, α-methylbenzyl, α,α-dimethylbenzyl or 2-phenylethyl.

Alkoxy containing up to 25 carbon atoms is a branched or unbranched radical, for example methoxy, ethoxy, propoxy, isopropoxy, n-butoxy, isobutoxy, pentyloxy, isopentyloxy, hexyloxy, heptyloxy, octyloxy, decyloxy, tetradecyloxy, hexadecyloxy or octadecyloxy.

$C_3$-$C_{25}$Alkoxy interrupted by oxygen is, for example, $CH_3$—O—$CH_2CH_2$O—, $CH_3$—O—$CH_2CH_2$—O—$CH_2CH_2$O—, $CH_3$—(O—$CH_2CH_2$—)$_2$O—$CH_2CH_2$O—, $CH_3$—(O—$CH_2CH_2$—)$_3$O—$CH_2CH_2$O— or $CH_3$—(O—$CH_2CH_2$—)$_4$O—$CH_2CH_2$O—.

$C_5$-$C_{12}$Cycloalkoxy is, for example, cyclopentyloxy, cyclohexyloxy, cycloheptyloxy, cyclooctyloxy, cyclononyloxy, cyclodecyloxy, cycloundecyloxy or cyclododecyloxy. Preference is given to cyclohexyloxy.

Alkenyloxy containing from 2 to 25 carbon atoms is a branched or unbranched radical, for example vinyloxy, propenyloxy, 2-butenyloxy, 3-butenyloxy, isobutenyloxy, n-2,4-pentadienyloxy, 3-methyl-2-butenyloxy, n-2-octenyloxy, n-2-dodecenyloxy, isododecenyloxy, oleyloxy, n-2-octadecenyloxy or n-4-octadecenyloxy.

$C_1$-$C_4$Alkyl-substituted phenoxy, which contains preferably from 1 to 3, especially 1 or 2, alkyl groups, is, for example, o-, m-or p-methylphenoxy, 2,3-dimethylphenoxy, 2,4-dimethylphenoxy, 2,5-dimethylphenoxy, 2,6-dimethylphenoxy, 3,4-dimethylphenoxy, 3,5-dimethylphenoxy, 2-methyl-6-ethylphenoxy, 4-tert-butylphenoxy, 2-ethylphenoxy or 2,6-diethylphenoxy.

$C_7$-$C_9$-Phenylalkoxy is, for example, benzyloxy, α-methylbenzyloxy, α,α-dimethylbenzyloxy or 2-phenylethoxy.

Halogen is, for example, chlorine, bromine or iodine. Preference is given to chlorine.

Alkanoyloxy containing from 2 to 25 carbon atoms is a branched or unbranched radical, for example acetoxy, propionyloxy, butanoyloxy, pentanoyloxy, hexanoyloxy, heptanoyloxy, octanoyloxy, nonanoyloxy, decanoyloxy, undecanoyloxy, dodecanoyloxy, tridecanoyloxy, tetradecanoyloxy, pentadecanoyloxy, hexadecanoyloxy, heptadecanoyloxy, octadecanoyloxy, eicosanoyloxy or docosanoyloxy.

$C_1$-$C_4$Alkyl substituted benzoyloxy which contains preferably from 1 to 3, especially 1 or 2, alkyl groups, is, for example, o-, m-or p-methylbenzoyloxy, 2,3-dimethylbenzoyloxy, 2,4-dimethylbenzoyloxy, 2,5-dimethylbenzoyloxy, 2,6-dimethylbenzoyloxy, 3,4-dimethylbenzoyloxy, 3,5-dimethylbenzoyloxy, 2-methyl-6-ethylbenzoyloxy, 4—tert -butylbenzoyloxy, 2-ethylbenzoyloxy or 2,6-diethylbenzoyloxy.

$C_1$-$C_4$Alkyl substituted phenylene which contains preferably from 1 to 3, especially 1 or 2, alkyl groups, is, for example, 2-methylphenylene, 2-ethylphenylene, 2-propylphenylene, 2-butylenephenylene, 2,6-dimethylphenylene, 2,5-dimethylphenylene or 2,3-dimethylphenylene.

$C_1$-$C_{25}$Alkylene substituted with $C_1$-$C_{25}$alkyl, $C_2$-$C_{25}$alkoxycarbonyl, $C_3$-$C_{25}$alkoxycarbonylalkyl or phenyl is a branched or unbranched radical, for example —$CH_2$($COOCH_3$)—, —$CH_2$($CH_2COOCH_3$)—, —$CH_2$($COOCH_2CH_3$)—, —$CH_2$($CH_2COOCH_2CH_3$)-2-methylethylene or 2-phenylethylene.

Alkinyl having 2 to 25 carbon atoms is a branched or unbranched radical such as, for example, acetylyl, propargyl, 2-butinyl, 3-butinyl, isobutinyl, n-2,4-pentadiinyl, 3-methyl-2-butinyl, n-2-octinyl, n-2-dodecinyl, iso-dodecinyl, n-2-octadecinyl or n-4-octadecinyl.

$C_5$-$C_{12}$cycloalkylene is for example cyclopentylene, cyclohexylene, cycloheptylene, cyclooctylene, cyclononylene, cyclodecylene, cycloundecylene or cyclododecylene. Cyclohexylene is preferred.

A $C_5$-$C_8$cycloalkylidene ring substituted by $C_1$-$C_4$alkyl, which contains preferably from 1 to 3, especially 1 or 2, branched or unbranched alkyl group radicals, is, for example, cyclopentylidene, methylcyclopentylidene, dimethylcyclopentylidene, cyclohexylidene, methylcyclohexylidene, dimethylcyclohexylidene, trimethylcyclohexylidene, tert-butylcyclohexylidene, cycloheptylidene or cyclooctylidene. Preference is given to cyclohexylidene and tert-butylcyclohexylidene.

Of interest are compositions comprising as component (c) at least one compound of the formula I, wherein when n is 1, $R_1$ is hydrogen, $C_1$-$C_{25}$alkyl, $C_1$-$C_{25}$alkyl substituted with furyl, morpholine, $C_1$-$C_4$dialkylamino, $C_1$-$C_4$trialkylammonium or $M^+$ $^-O_3S$—; $C_2$-$C_{25}$alkyl interrupted by oxygen; $C_5$-$C_{12}$cycloalkyl, $C_2$-$C_{25}$alkenyl, unsubstituted or $C_1$-$C_4$alkyl-substituted phenyl; $C_7$-$C_{12}$phenoxyalkyl, unsubstituted or $C_1$-$C_4$alkyl substituted $C_7$-$C_9$bicycloalkyl;

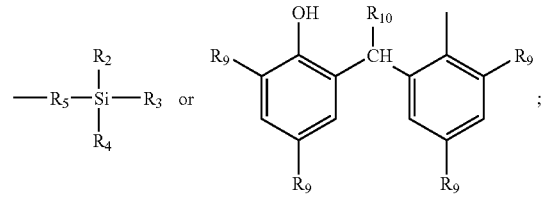

or when $R_7$ is a direct bond, $R_1$ is —CN, —$SOR_8$, —$SO_2R_8$, —$NO_2$ or —$COR_8$, when n is 2, $R_1$ is $C_1$-$C_{25}$alkylene, $C_1$-$C_{25}$alkylene substituted with $C_1$-$C_4$alkyl; $C_2$-$C_{25}$alkylene substituted with $C_1$-$C_4$alkyl and interrupted by oxygen; $C_2$-$C_{25}$alkylene interrupted by oxygen, sulfur, phenylene or cyclohexylene;

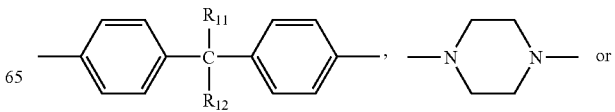

-continued

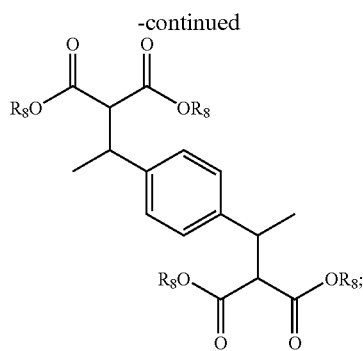

or when $R_6$ and $R_7$ are a direct bond, $R_1$ is

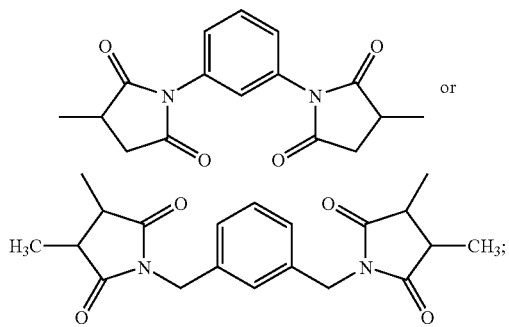

$R_2$, $R_3$ and $R_4$ are each independently of the others $C_1$-$C_{25}$alkyl, $C_2$-$C_{25}$alkyl interrupted by oxygen; $C_5$-$C_{12}$cycloalkyl, $C_2$-$C_{25}$alkenyl, unsubstituted or $C_1$-$C_4$alkyl-substituted phenyl, $C_7$-$C_9$phenylalkyl, $C_1$-$C_{25}$alkoxy, $C_3$-$C_{25}$alkoxy interrupted by oxygen; $C_5$-$C_{12}$cycloalkoxy, $C_2$-$C_{25}$alkenyloxy, unsubstituted or $C_1$-$C_4$alkyl-substituted phenoxy, $C_7$-$C_9$phenylalkoxy, halogen, $C_2$-$C_{25}$alkanoyloxy or unsubstituted or $C_1$-$C_4$alkyl substituted benzoyloxy; with the proviso that at least one of $R_2$, $R_3$ or $R_4$ is $C_1$-$C_{25}$alkoxy, $C_3$-$C_{25}$alkoxy interrupted by oxygen; $C_5$-$C_{12}$cycloalkoxy, $C_2$-$C_{25}$alkenyloxy, unsubstituted or $C_1$-$C_4$alkyl-substituted phenoxy, $C_7$-$C_9$phenylalkoxy, halogen, $C_2$-$C_{25}$alkanoyloxy or unsubstituted or $C_1$-$C_4$alkyl substituted benzoyloxy;

$R_5$ is $C_1$-$C_{25}$alkylene, $C_5$-$C_{12}$cycloalkylene, unsubstituted or $C_1$-$C_4$alkyl substituted phenylene;

$R_6$ is a direct bond, $C_1$-$C_{25}$alkylene; or $C_1$-$C_{25}$alkylene substituted with $C_1$-$C_{25}$alkyl, $C_2$-$C_{25}$alkoxycarbonyl, $C_3$-$C_{25}$alkoxycarbonylalkyl or phenyl;

$R_7$ is a direct bond or

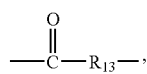

with the proviso that, when $R_7$ is a direct bond and n is 1, $R_6$ is not a direct bond; and with the proviso that, when $R_7$ is

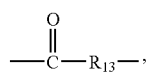

$R_6$ is not a direct bond;

$R_8$ is $C_1$-$C_{25}$alkyl, $C_2$-$C_{25}$alkyl interrupted by oxygen; $C_5$-$C_{12}$cycloalkyl, $C_2$-$C_{25}$alkenyl, $C_2$-$C_{25}$alkinyl, $C_7$-$C_9$phenylalkyl, unsubstituted or $C_1$-$C_4$alkyl-substituted phenyl, $R_9$ is $C_1$-$C_5$alkyl, $R_{10}$ is hydrogen or $C_1$-$C_4$alkyl, $R_{11}$ and $R_{12}$ are each independently of the other hydrogen, $CF_3$, $C_1$-$C_{12}$alkyl or phenyl, or $R_{11}$ and $R_{12}$, together with the carbon atom to which they are bonded, form a $C_5$-$C_8$cycloalkylidene ring that is unsubstituted or substituted by from 1 to 3 $C_1$-$C_4$alkyl groups, $R_{13}$ is oxygen or —$N(R_{14})$—, $R_{14}$ is hydrogen or $C_1$-$C_{12}$alkyl, M is sodium, potassium or ammonium, m is 0, 1 or 2, and n is 1 or 2; or an oligomeric hydrolysis product of the compound of the formula I.

Interesting compositions comprise, as component (c), at least one compound of the formula I wherein when n is 1, $R_1$ is hydrogen, $C_1$-$C_{18}$alkyl, $C_1$-$C_{18}$alkyl substituted with furyl, morpholine, $C_1$-$C_4$dialkylamino, $C_1$-$C_4$trialkylammonium or $M^+$ $^-O_3S$—; $C_2$-$C_{18}$alkyl interrupted by oxygen; $C_5$-$C_8$cycloalkyl, $C_2$-$C_{18}$alkenyl, unsubstituted or $C_1$-$C_4$alkyl-substituted phenyl; $C_7$-$C_{10}$phenoxyalkyl, unsubstituted or $C_1$-$C_4$alkyl substituted $C_7$-$C_9$bicycloalkyl;

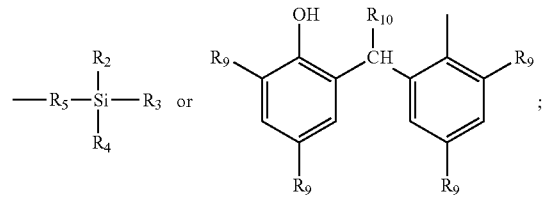

or when $R_7$ is a direct bond, $R_1$ is —CN, —$SOR_8$, —$SO_2R_8$, —$NO_2$ or —$COR_8$, when n is 2, $R_1$ is $C_1$-$C_{18}$alkylene, $C_1$-$C_{18}$alkylene substituted with $C_1$-$C_4$alkyl; $C_2$-$C_{18}$alkylene substituted with $C_1$-$C_4$alkyl and interrupted by oxygen; $C_2$-$C_{18}$alkylene interrupted by oxygen, sulfur, phenylene or cyclohexylene;

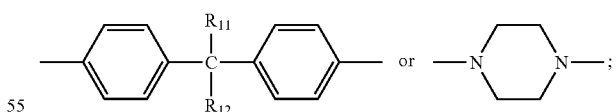

or when $R_6$ and $R_7$ are a direct bond, $R_1$ is

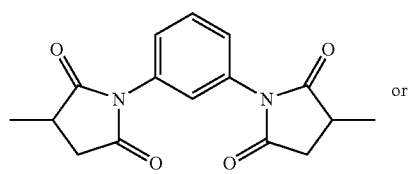

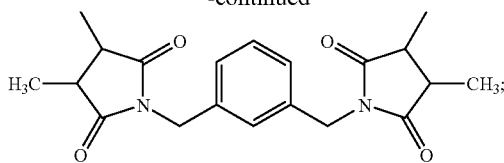

$R_2$, $R_3$ and $R_4$ are each independently of the others $C_1$-$C_{18}$alkyl, $C_2$-$C_{18}$alkyl interrupted by oxygen; $C_5$-$C_8$cycloalkyl, $C_2$-$C_{18}$alkenyl, unsubstituted or $C_1$-$C_4$alkyl-substituted phenyl, $C_7$-$C_9$phenylalkyl, $C_1$-$C_{18}$alkoxy, $C_3$-$C_{18}$alkoxy interrupted by oxygen; $C_5$-$C_8$cycloalkoxy, $C_2$-$C_{18}$alkenyloxy, unsubstituted or $C_1$-$C_4$alkyl-substituted phenoxy, $C_7$-$C_9$phenylalkoxy, halogen, $C_2$-$C_{18}$alkanoyloxy or unsubstituted or $C_1$-$C_4$alkyl substituted benzoyloxy; with the proviso that at least one of $R_2$, $R_3$ or $R_4$ is $C_1$-$C_{18}$alkoxy, $C_3$-$C_{18}$alkoxy interrupted by oxygen; $C_5$-$C_8$cycloalkoxy, $C_2$-$C_{18}$alkenyloxy, unsubstituted or $C_1$-$C_4$alkyl-substituted phenoxy, $C_7$-$C_9$phenylalkoxy, halogen, $C_2$-$C_{18}$alkanoyloxy or unsubstituted or $C_1$-$C_4$alkyl substituted benzoyloxy;

$R_5$ is $C_1$-$C_{18}$alkylene, $C_5$-$C_8$cycloalkylene, unsubstituted or $C_1$-$C_4$alkyl substituted phenylene;

$R_6$ is a direct bond, $C_1$-$C_{18}$alkylene; or $C_1$-$C_{18}$alkylene substituted with $C_1$-$C_{18}$alkyl, $C_2$-$C_{18}$alkoxycarbonyl, $C_3$-$C_{18}$alkoxycarbonylalkyl or phenyl;

$R_7$ is a direct bond or

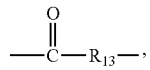

with the proviso that, when $R_7$ is a direct bond and n is 1, $R_6$ is not a direct bond; and with the proviso that, when $R_7$ is

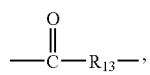

$R_6$ is not a direct bond;

$R_8$ is $C_1$-$C_{18}$alkyl, $C_2$-$C_{18}$alkyl interrupted by oxygen; $C_5$-$C_8$cycloalkyl, $C_2$-$C_{18}$alkenyl, $C_2$-$C_{18}$alkinyl, $C_7$-$C_9$phenylalkyl, unsubstituted or $C_1$-$C_4$alkyl-substituted phenyl, $R_9$ is $C_1$-$C_6$alkyl, $R_{10}$ is hydrogen or methyl, $R_{11}$ and $R_{12}$ are each independently of the other hydrogen, $CF_3$, $C_1$-$C_8$alkyl or phenyl, or $R_{11}$ and $R_{12}$, together with the carbon atom to which they are bonded, form a $C_5$-$C_8$cycloalkylidene ring that is unsubstituted or substituted by from 1 to 3 $C_1$-$C_4$alkyl groups, $R_{13}$ is oxygen or $-N(R_{14})-$, $R_{14}$ is hydrogen or $C_1$-$C_8$alkyl, M is sodium, potassium or ammonium, m is 0, 1 or 2, and n is 1 or 2.

Preferred compositions comprise, as component (c), at least one compound of the formula I wherein $R_2$, $R_3$ and $R_4$ are each independently of the others $C_1$-$C_4$alkyl or $C_1$-$C_4$alkoxy; with the proviso that at least one of $R_2$, $R_3$ or $R_4$ is $C_1$-$C_4$alkoxy.

Preference is also given to compositions comprising, as component (c), at least one compound of the formula I wherein $R_5$ is $C_2$-$C_4$alkylene.

Particular preference is given to compositions comprising, as component (c), at least one compound of the formula I wherein when n is 1, $R_1$ is hydrogen, $C_1$-$C_{18}$alkyl, $C_1$-$C_{12}$alkyl substituted with furyl, morpholine, $C_1$-$C_4$dialkylamino, $C_1$-$C_4$trialkylammonium or $M^+$ $^-O_3S-$; $C_2$-$C_{12}$alkyl interrupted by oxygen; cyclohexyl, $C_4$-$C_{12}$-alkenyl, phenyl, $C_7$-$C_{10}$phenoxyalkyl, unsubstituted or $C_1$-$C_4$alkyl substituted $C_7$-$C_9$bicycloalkyl;

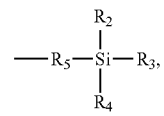

or when $R_7$ is a direct bond, $R_1$ is $-CN$, $-SOR_8$ or $-SO_2R_8$;

when n is 2, $R_1$ is $C_2$-$C_{12}$alkylene, $C_2$-$C_{12}$alkylene substituted with methyl; $C_2$-$C_{12}$alkylene substituted with methyl and interrupted by oxygen; $C_4$-$C_{12}$alkylene interrupted by oxygen, sulfur, phenylene or cyclohexylene;

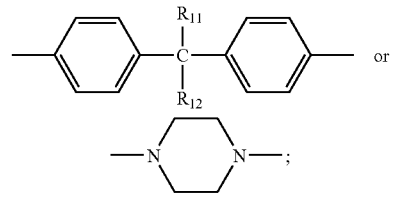

or when $R_6$ and $R_7$ are a direct bond, $R_1$ is

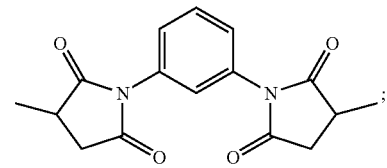

$R_2$, $R_3$ and $R_4$ are each independently of the others $C_1$-$C_8$alkyl, $C_4$-$C_8$alkyl interrupted by oxygen; cyclohexyl, $C_2$-$C_{12}$alkenyl, benzyl, $C_1$-$C_8$alkoxy, $C_3$-$C_8$alkoxy interrupted by oxygen; cyclohexyloxy, $C_2$-$C_{12}$alkenyloxy, phenoxy, benzyloxy, chloro, bromo, $C_2$-$C_8$alkanoyloxy or benzoyloxy; with the proviso that at least one of $R_2$, $R_3$ or $R_4$ is $C_1$-$C_8$alkoxy, $C_3$-$C_8$alkoxy interrupted by oxygen; cyclohexyloxy, $C_2$-$C_{12}$alkenyloxy, phenoxy, benzyloxy, chloro, bromo, $C_2$-$C_8$alkanoyloxy or benzoyloxy;

$R_5$ is $C_2$-$C_8$alkylene, cyclohexylene or phenylene;

$R_6$ is a direct bond, $C_1$-$C_8$alkylene; or $C_1$-$C_8$alkylene substituted with $C_1$-$C_4$alkyl, $C_2$-$C_8$alkoxycarbonyl, $C_3$-$C_8$alkoxycarbonylalkyl or phenyl;

$R_7$ is a direct bond or

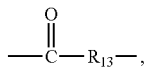

with the proviso that, when $R_7$ is a direct bond and n is 1, $R_6$ is not a direct bond; and with the proviso that, when $R_7$ is

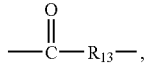

$R_6$ is not a direct bond;
$R_8$ is $C_1$-$C_{12}$alkyl, $C_2$-$C_{12}$alkyl interrupted by oxygen; cyclohexyl, $C_2$-$C_{12}$alkenyl, $C_2$-$C_{12}$alkinyl, benzyl or phenyl,
$R_{11}$ and $R_{12}$ are each independently of the other hydrogen or $C_1$-$C_8$alkyl, or $R_{11}$ and $R_{12}$, together with the carbon atom to which they are bonded, form a cyclohexylidene ring that is unsubstituted or substituted by from 1 to 3 methyl groups,
$R_{13}$ is oxygen or —N($R_{14}$)—,
$R_{14}$ is hydrogen or $C_1$-$C_4$alkyl,
M is sodium or potassium,
m is 0 or 1, and
n is 1 or 2.

Of interest are compositions comprising, as component (c), at least one compound of the formula I wherein
when n is 1,
$R_1$ is hydrogen, $C_1$-$C_{18}$alkyl, $C_1$-$C_8$alkyl substituted with furyl, morpholine, $C_1$-$C_4$dialkylamino, $C_1$-$C_4$trialkylammonium or $M^+$ $^-O_3S$—; $C_2$-$C_8$alkyl interrupted by oxygen; cyclohexyl, $C_4$-$C_{10}$-alkenyl, phenyl, $C_7$-$C_{10}$phenoxyalkyl, unsubstituted or $C_1$-$C_4$alkyl substituted $C_7$-$C_9$bicycloalkyl;

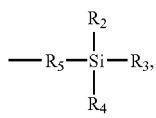

or when $R_7$ is a direct bond, $R_1$ is —CN, —SOR$_8$ or —SO$_2R_8$;
when n is 2,
$R_1$ is $C_2$-$C_8$alkylene, $C_2$-$C_8$alkylene substituted with methyl; $C_2$-$C_{10}$alkylene substituted with methyl and interrupted by oxygen; $C_4$-$C_{12}$alkylene interrupted by oxygen or sulfur;

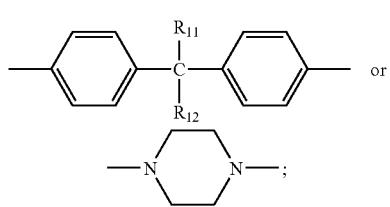

or when $R_6$ and $R_7$ are a direct bond, $R_1$ is

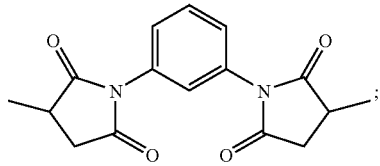

$R_2$, $R_3$ and $R_4$ are each independently of the others $C_1$-$C_4$alkyl, cyclohexyl, $C_2$-$C_6$alkenyl, benzyl, $C_1$-$C_4$alkoxy, cyclohexyloxy, $C_2$-$C_6$alkenyloxy, phenoxy, benzyloxy, chloro, $C_2$-$C_4$alkanoyloxy or benzoyloxy; with the proviso that at least one of $R_2$, $R_3$ or $R_4$ is $C_1$-$C_4$alkoxy, cyclohexyloxy, $C_2$-$C_6$alkenyloxy, phenoxy, benzyloxy, chloro, $C_2$-$C_4$alkanoyloxy or benzoyloxy;
$R_5$ is $C_2$-$C_6$alkylene or cyclohexylene,
$R_6$ is a direct bond, $C_1$-$C_6$alkylene; or $C_1$-$C_6$alkylene substituted with methyl, $C_2$-$C_6$alkoxycarbonyl, $C_3$-$C_6$alkoxycarbonylalkyl or phenyl;
$R_7$ is a direct bond or

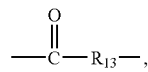

with the proviso that, when $R_7$ is a direct bond and n is 1, $R_6$ is not a direct bond; and with the proviso that, when $R_7$ is

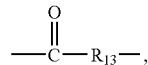

$R_6$ is not a direct bond;
$R_8$ is $C_1$-$C_8$alkyl or $C_2$-$C_{12}$alkenyl,
$R_{11}$ and $R_{12}$ are each independently of the other hydrogen or $C_1$-$C_6$alkyl,
$R_{13}$ is oxygen or —N($R_{14}$)—,
$R_{14}$ is hydrogen or methyl,
M is sodium or potassium,
m is 0 and
n is 1 or 2.

Also of interest are compositions comprising, as component (c), at least one compound of the formula I wherein
when n is 1,
$R_1$ is hydrogen, $C_1$-$C_{18}$alkyl, $C_1$-$C_4$alkyl substituted with furyl, morpholine, $C_1$-$C_4$dialkylamino, $C_1$-$C_4$trialkylammonium or $M^+$ $^-O_3S$—; $C_2$-$C_6$alkyl interrupted by oxygen; cyclohexyl, $C_4$-$C_{10}$alkenyl, phenyl; $C_7$-$C_9$phenoxyalkyl, unsubstituted or $C_1$-$C_4$alkyl substituted $C_7$-$C_9$bicycloalkyl;

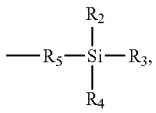

or when $R_7$ is a direct bond, $R_1$ is —CN;
when n is 2,
$R_1$ is $C_2$-$C_6$alkylene, $C_2$-$C_4$alkylene substituted with methyl; $C_4$-$C_8$alkylene substituted with methyl and interrupted by oxygen; $C_4$-$C_8$alkylene interrupted by oxygen;

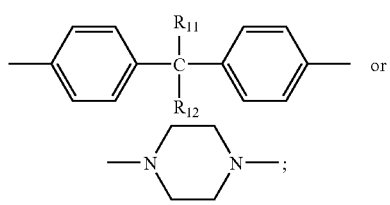

or when $R_6$ and $R_7$ are a direct bond, $R_1$ is

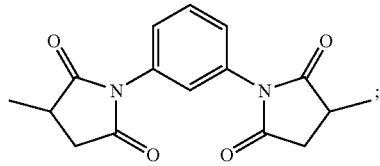

$R_2$, $R_3$ and $R_4$ are each independently of the others $C_1$-$C_4$alkyl or $C_1$-$C_4$alkoxy; with the proviso that at least one of $R_2$, $R_3$ or $R_4$ is $C_1$-$C_4$alkoxy;
$R_5$ is $C_2$-$C_4$alkylene,
$R_6$ is a direct bond, $C_1$-$C_3$alkylene; or $C_1$-$C_3$alkylene substituted with methyl, $C_2$-$C_3$alkoxycarbonyl, $C_3$-$C_6$alkoxycarbonylalkyl or phenyl;

$R_7$ is a direct bond or

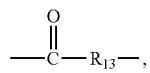

with the proviso that, when $R_7$ is a direct bond and n is 1, $R_6$ is not a direct bond; and with the proviso that, when $R_7$ is

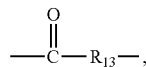

$R_6$ is not a direct bond;
$R_{11}$ and $R_{12}$ are each independently of the other hydrogen or $C_1$-$C_4$alkyl,
$R_{13}$ is oxygen or —N($R_{14}$)—,
$R_{14}$ is hydrogen,
M is potassium,
m is 0 and
n is 1 or 2; or an oligomeric hydrolysis product of the compound of the formula Ia.

Of very special interest are compositions comprising, as component (c), the compounds 101 to 222.

(101)
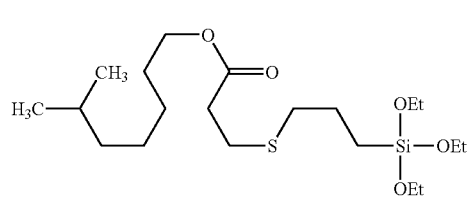

(102)
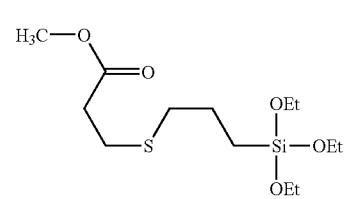

(103)
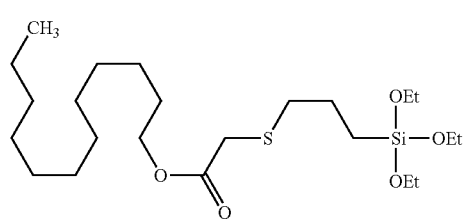

(104)
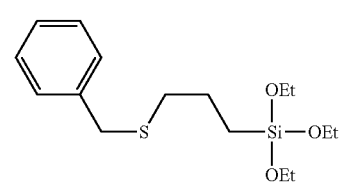

(105)
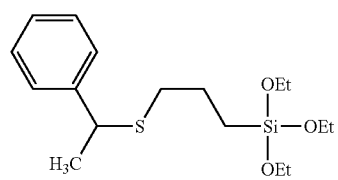

(106)
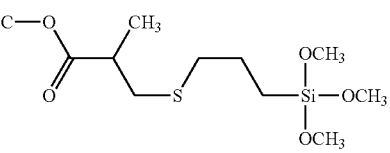

(107)
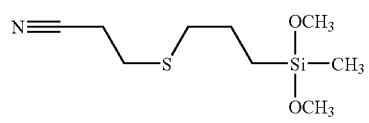

(108)
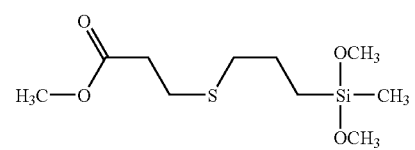

-continued
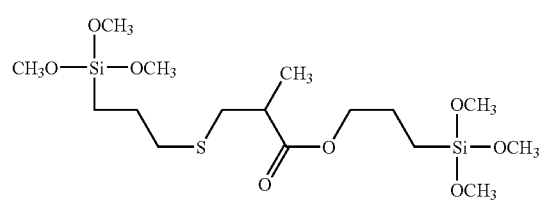
(109)
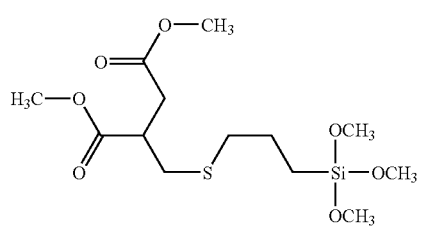
(110)
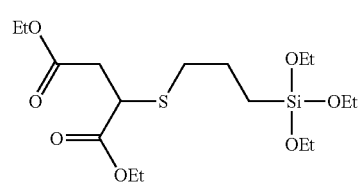
(111)
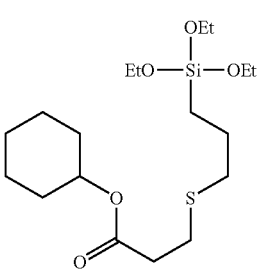
(112)
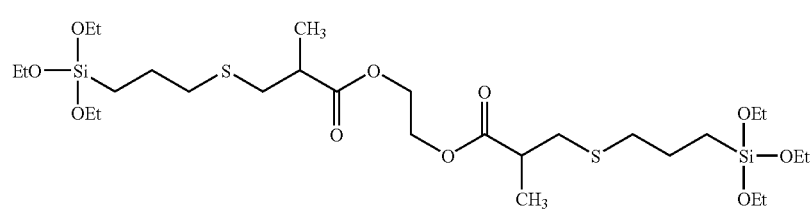
(113)
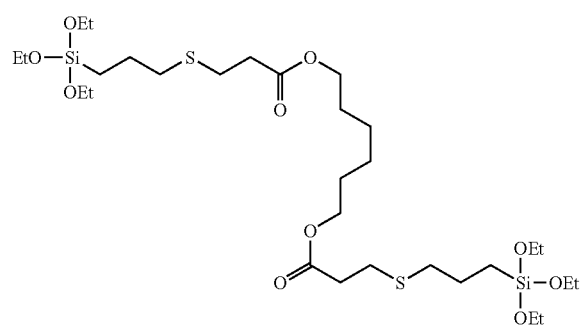
(114)
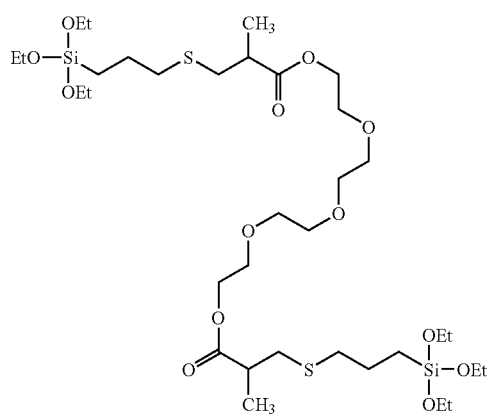
(115)
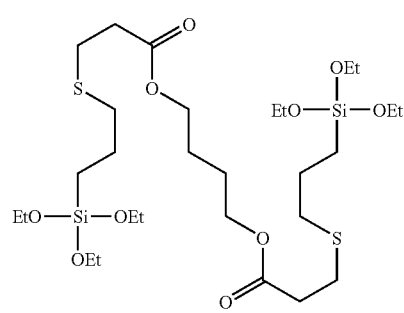
(116)
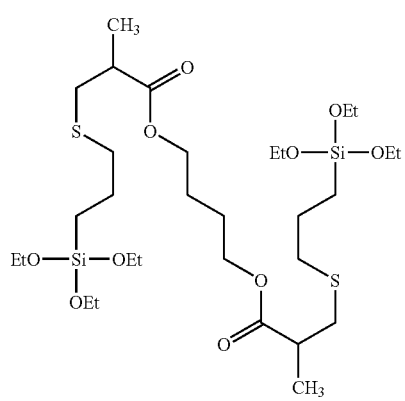
(117)

-continued
(118) 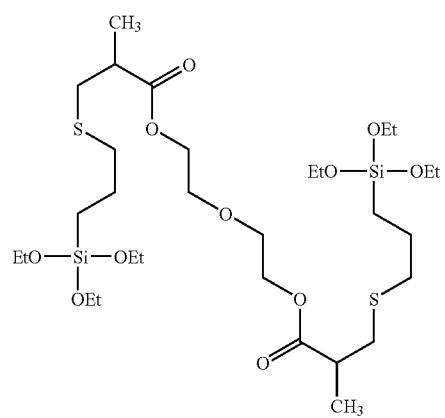
(119) 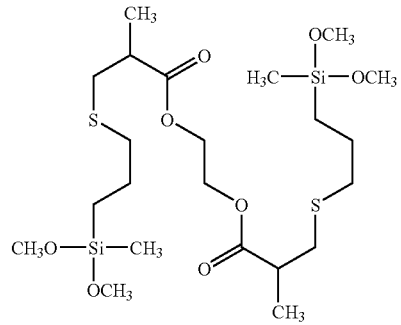
(120) 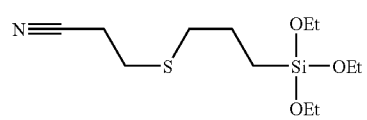
(121)
(122) 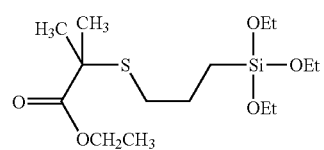
(123)
(124) 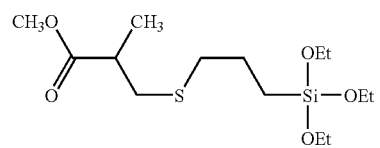
(125)
(126) 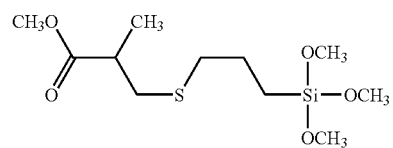
(127)
(128) 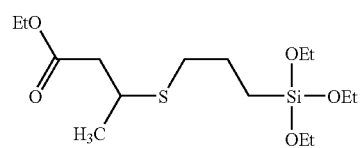
(129)
(130) 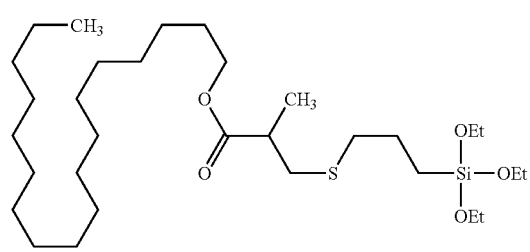
(131) 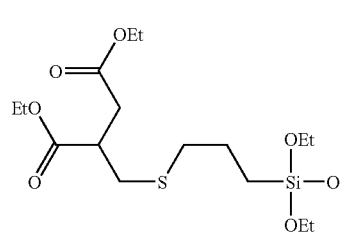

21
(132)
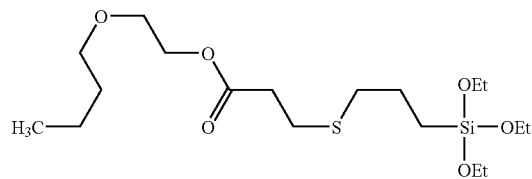
22
-continued
(133)
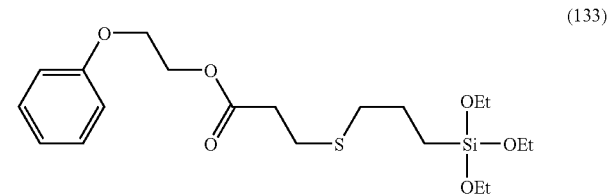
(134)
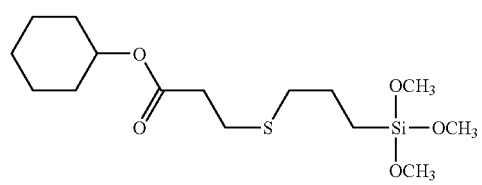
(135)
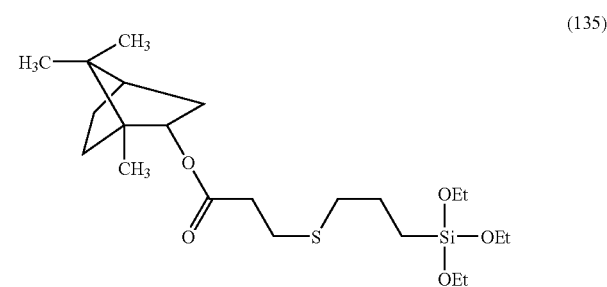
(136)
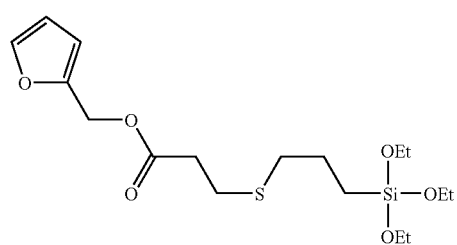
(137)
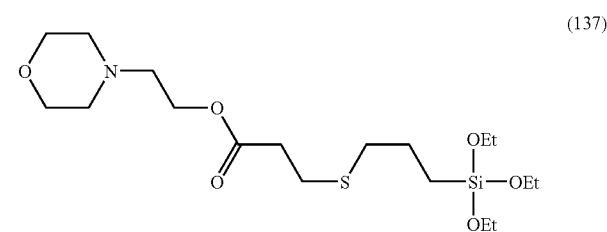
(138)
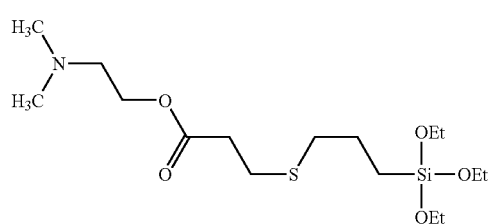
(139)
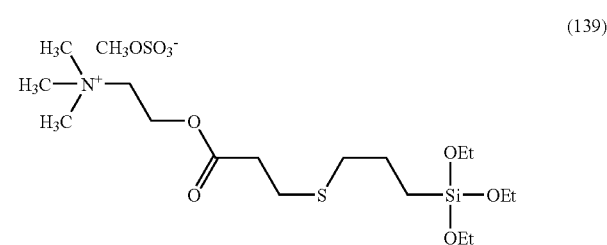
(140)
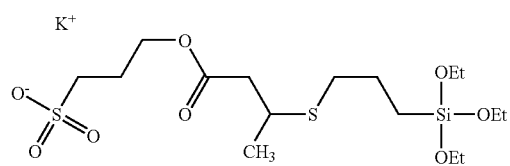
(141)
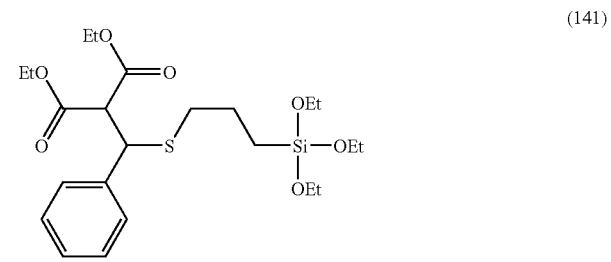
(142)
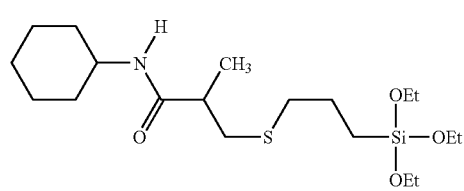
(143)
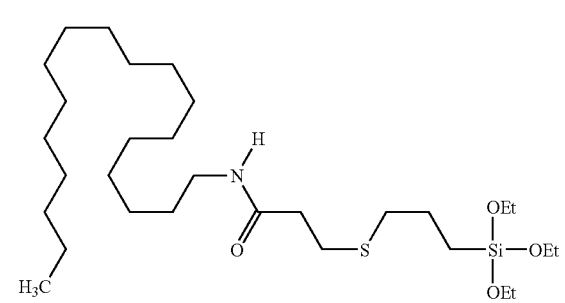

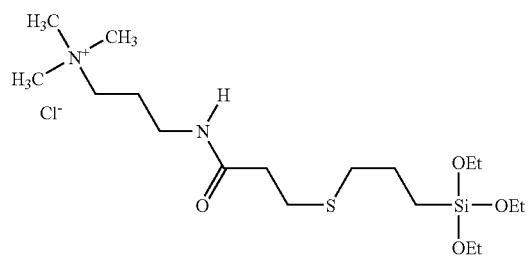
(144)
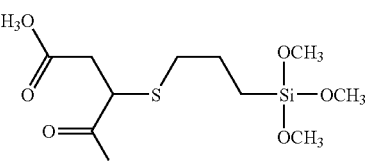
(145)
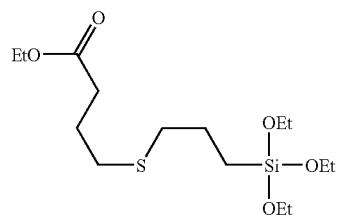
(146)
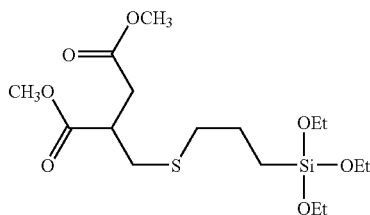
(147)
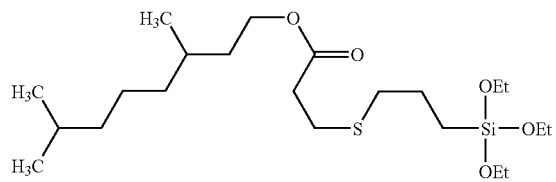
(148)
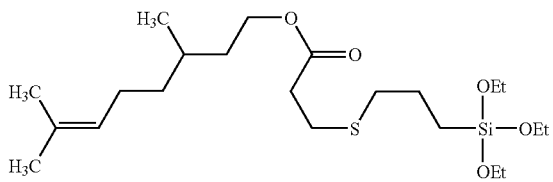
(149)
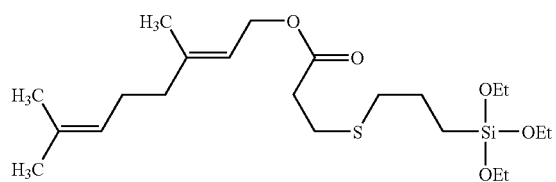
(150)
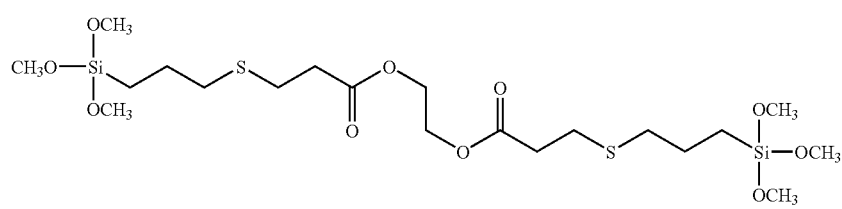
(151)
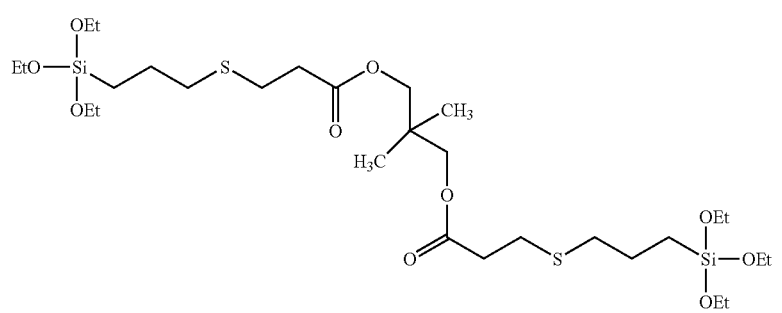
(152)
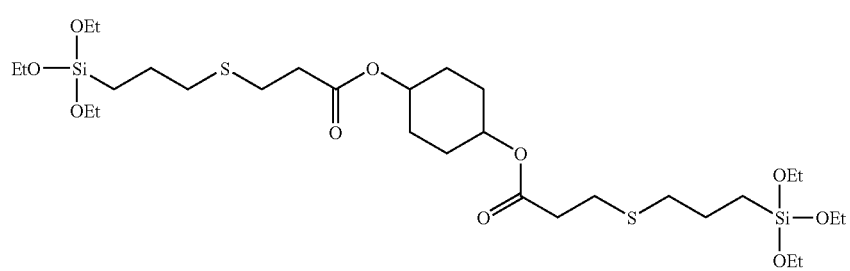
(153)

-continued
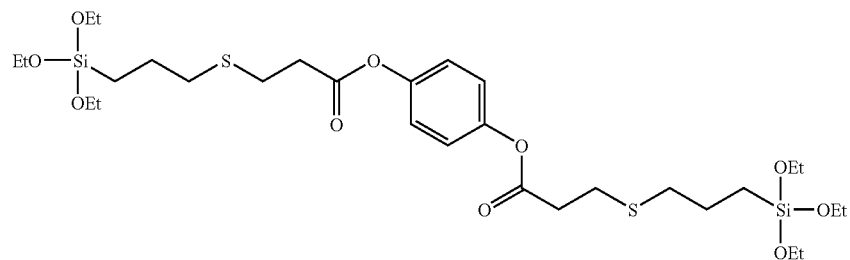
(154)
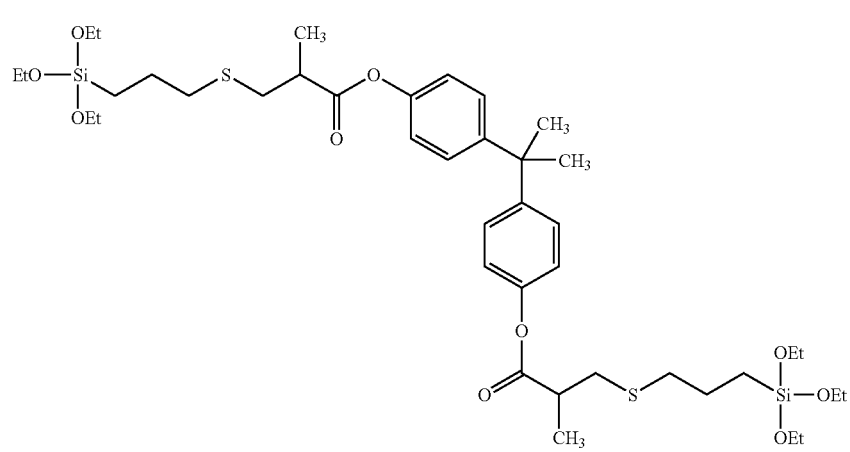
(155)
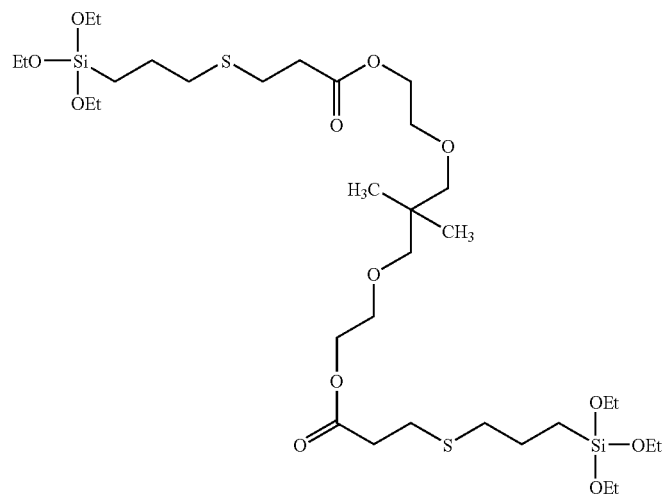
(156)
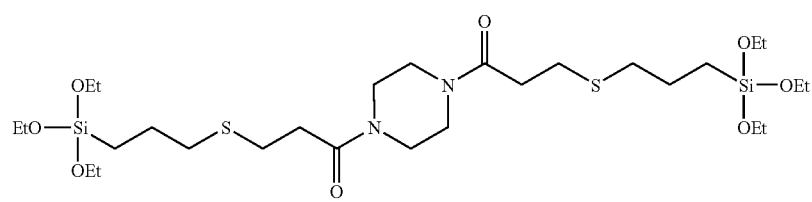
(157)

-continued
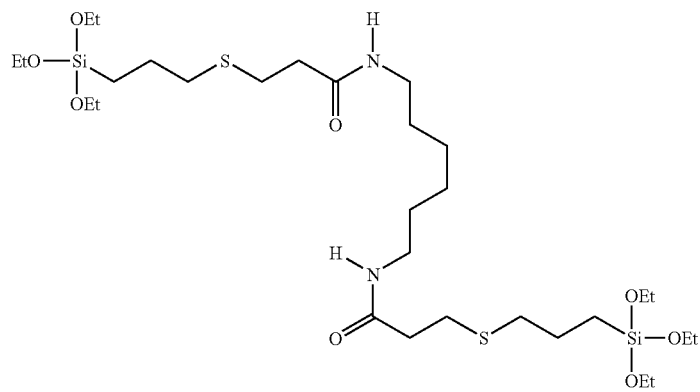
(158)
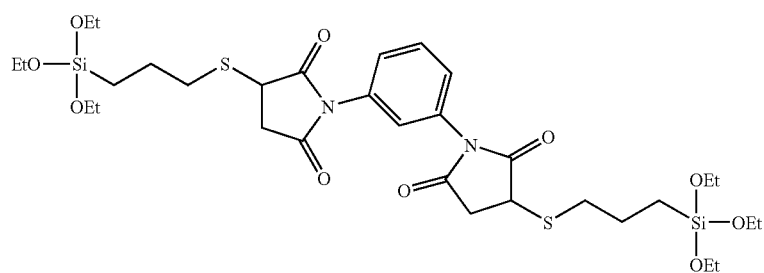
(159)
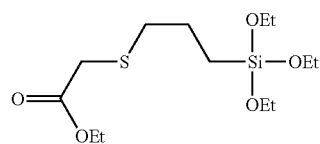
(160)
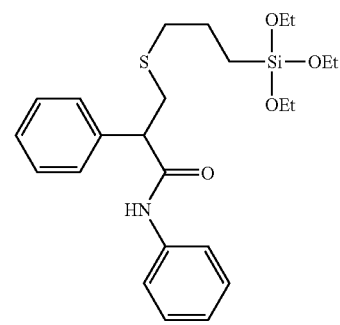
(161)
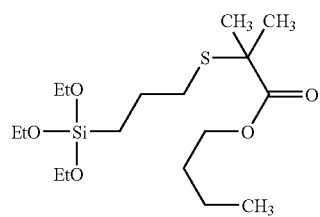
(162)
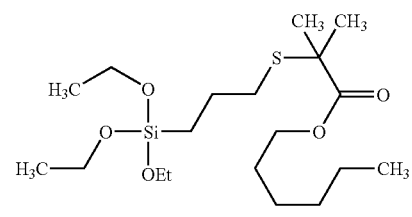
(163)
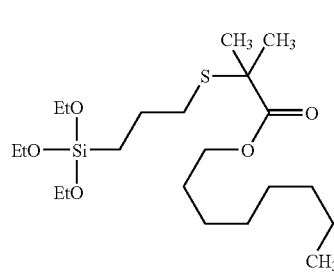
(164)
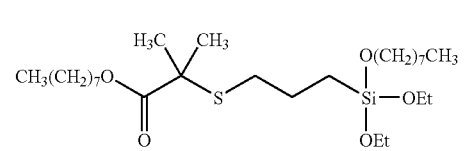
(165)
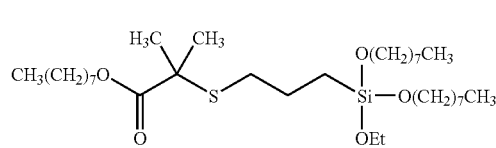
(166)
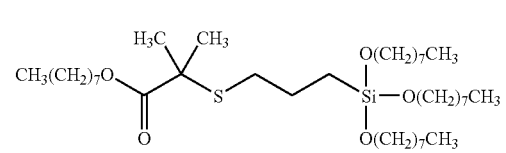
(167)

-continued
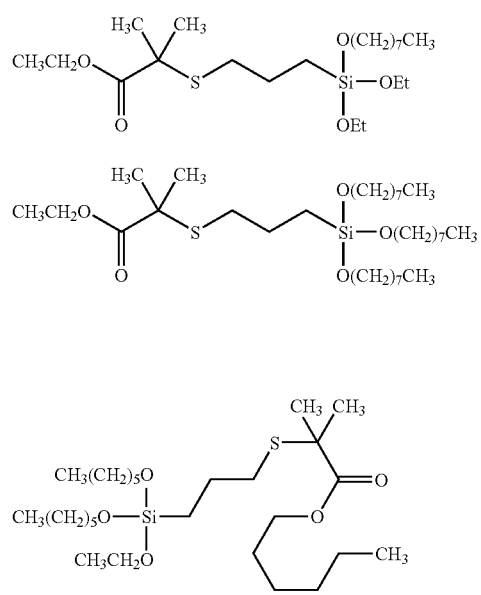
(168)
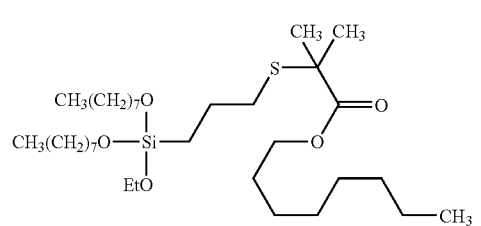
(170)
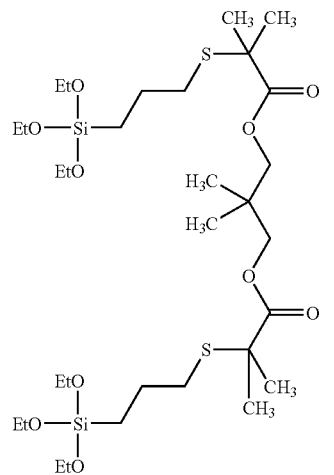
(172)
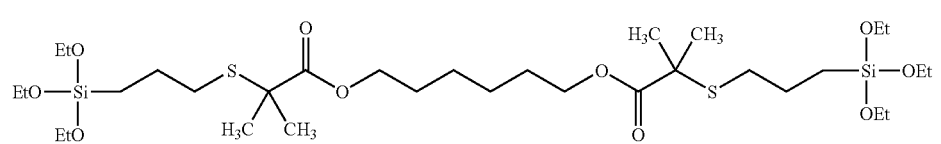
(174)
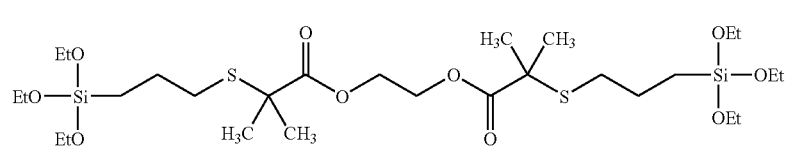
(176)
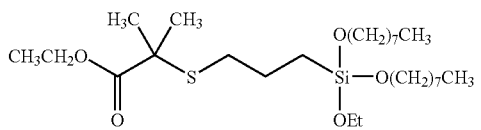
(169)
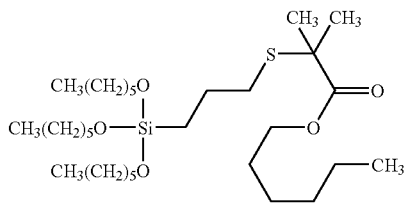
(171)
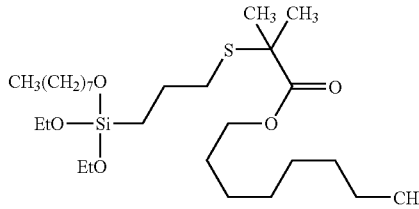
(173)
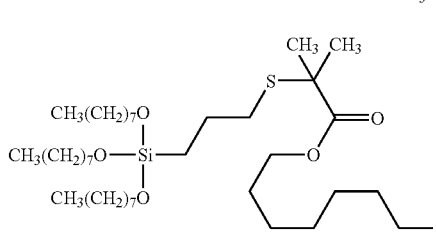
(175)
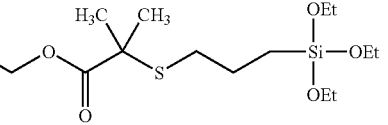
(177)
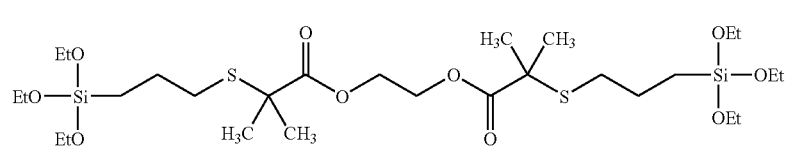
(178)

-continued
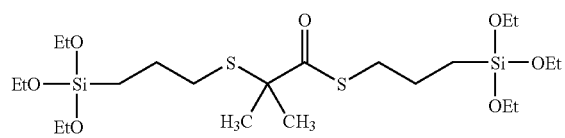(179)
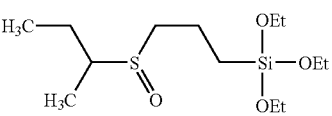(180)
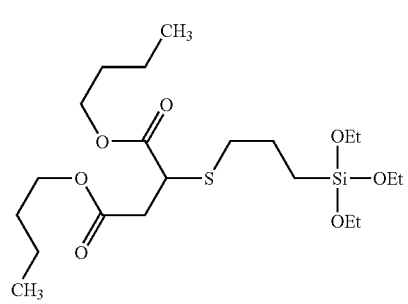(181)
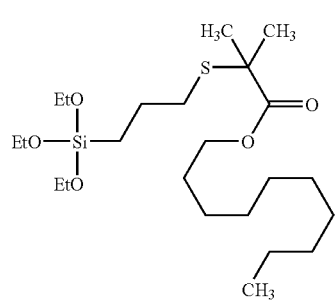(182)
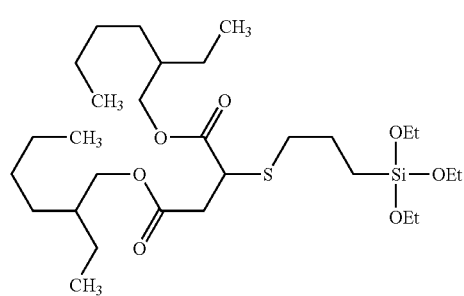(183)
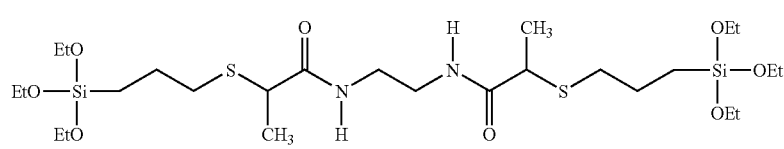(184)
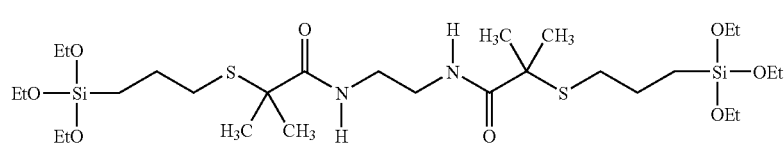(185)
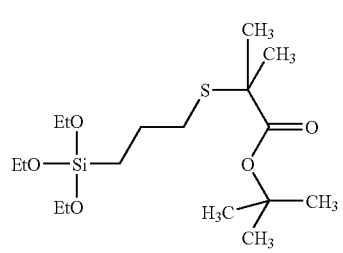(186)
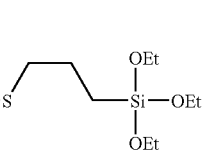(187)
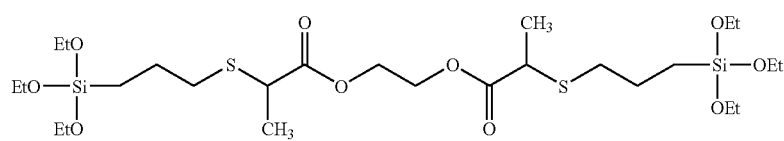(188)

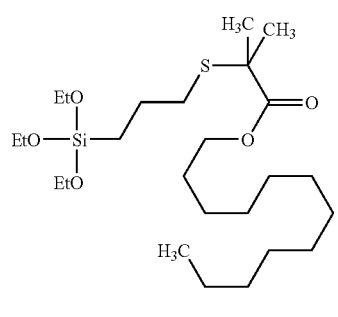
(189)
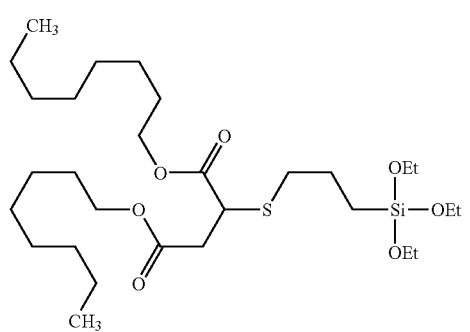
(190)
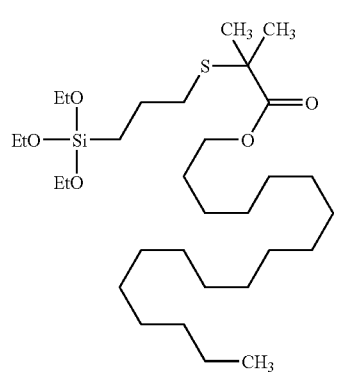
(191)
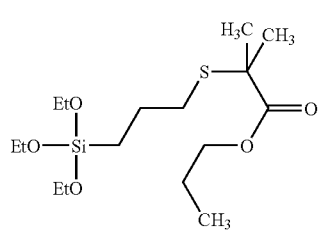
(192)
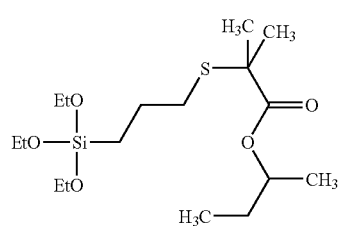
(193)
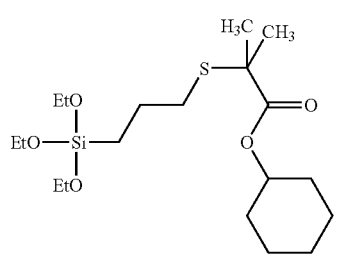
(194)
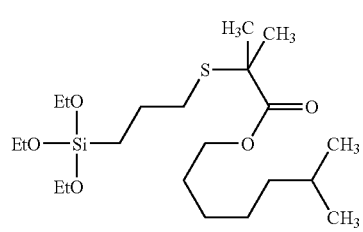
(195)
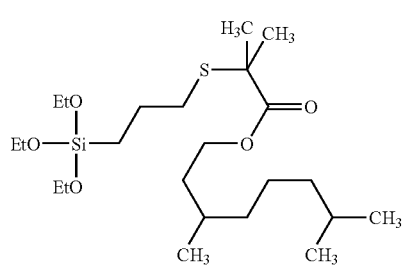
(196)
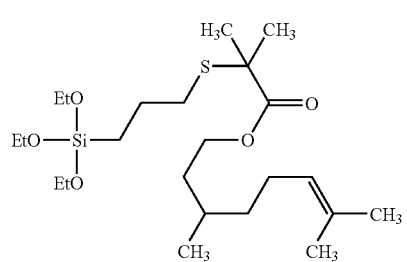
(197)
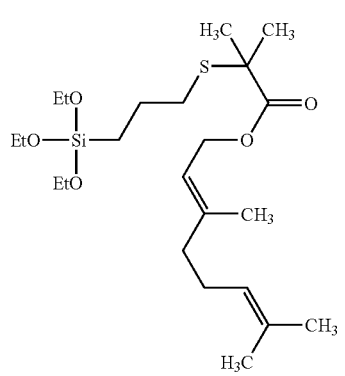
(198)

-continued
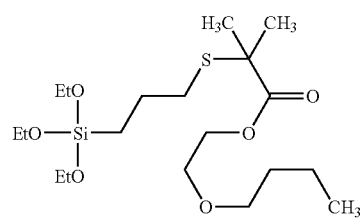 (199)
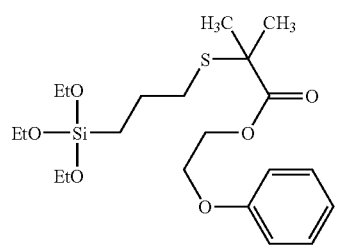 (200)
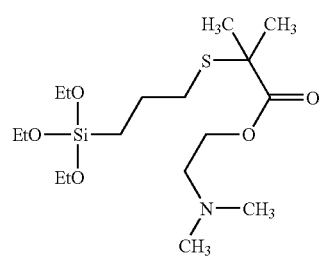 (201)
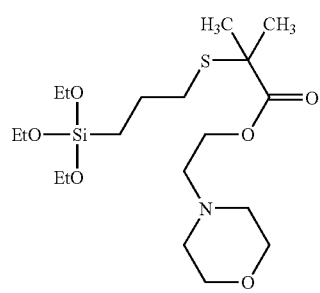 (202)
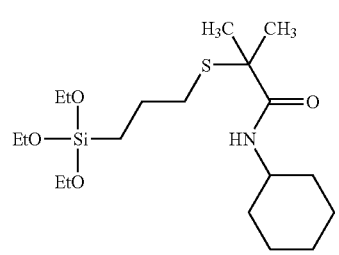 (203)
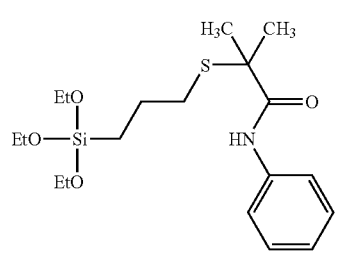 (204)
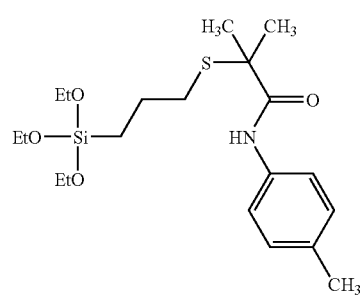 (205)
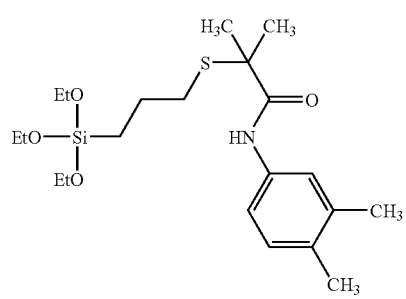 (206)
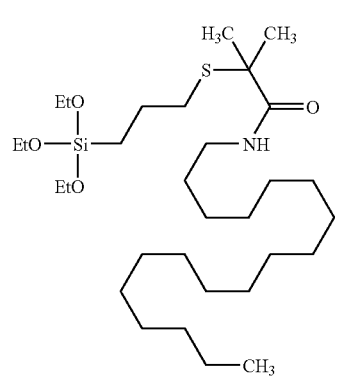 (207)
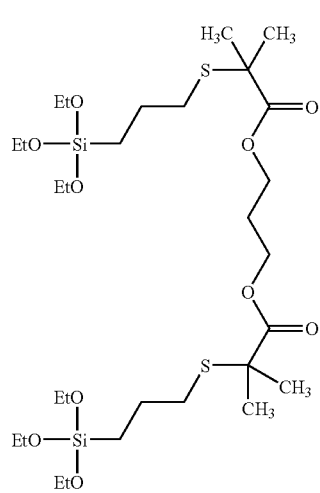 (208)

-continued
(209)
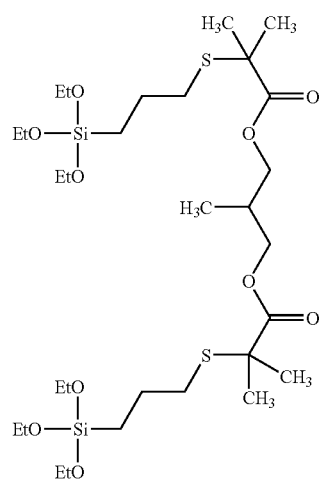
(210)
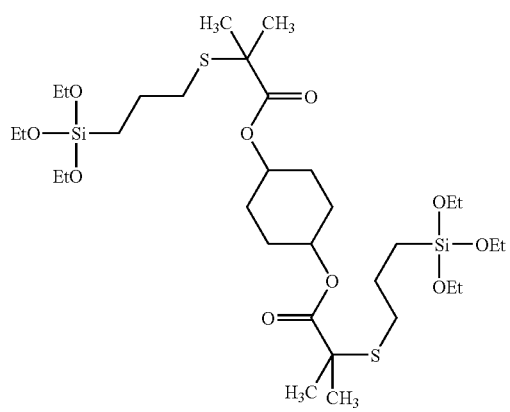
(211)
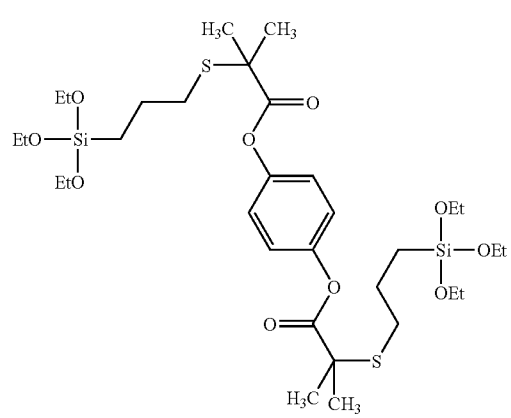
(212)
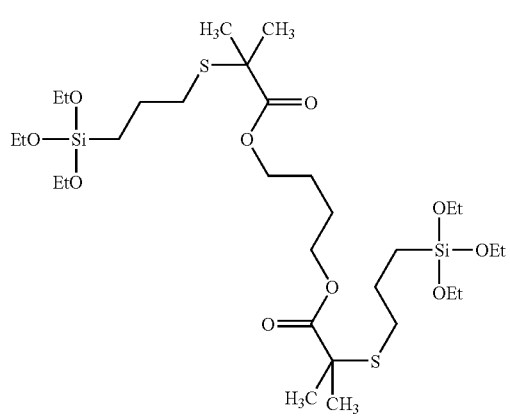
(213)
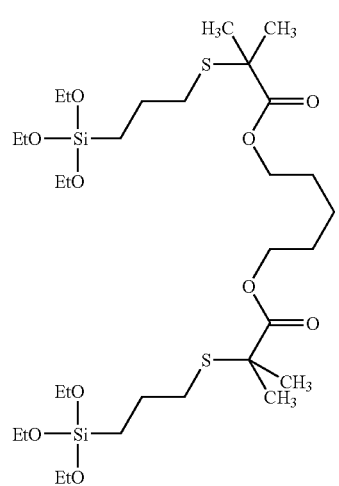
(214)
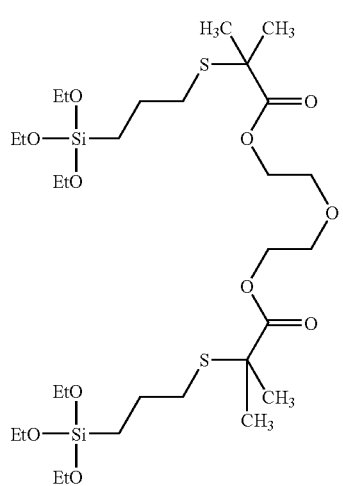

-continued
(215)
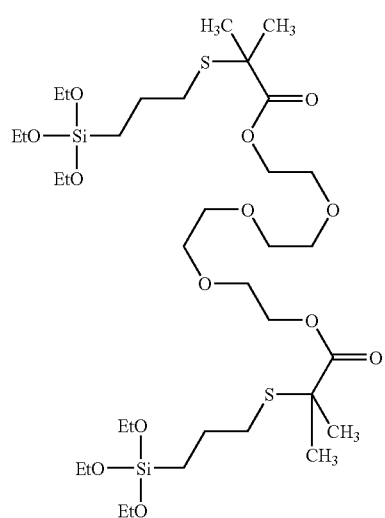
(216)
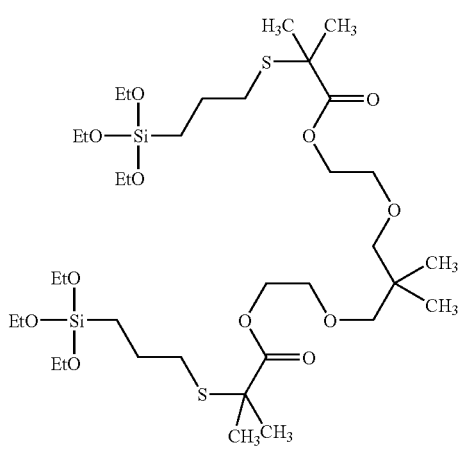
(217)
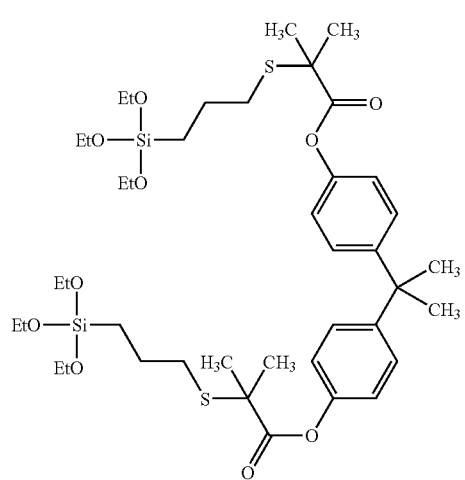
(218)
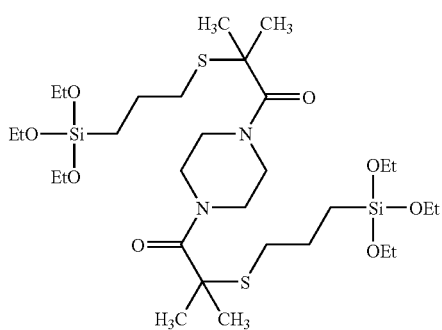
(219)
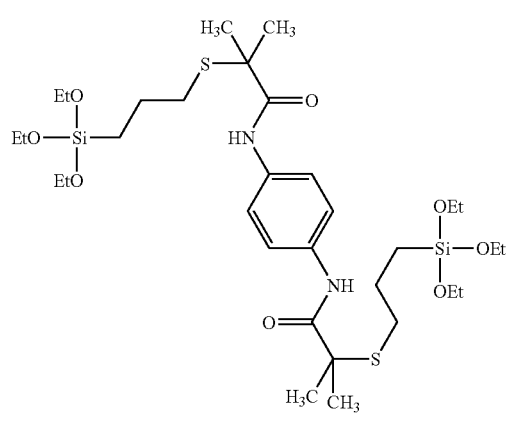
(220)
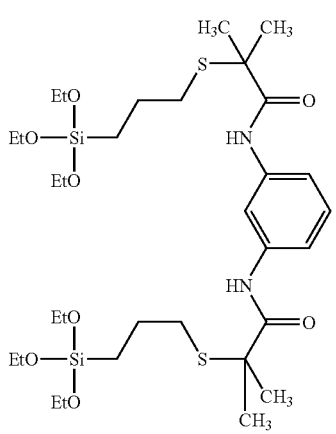

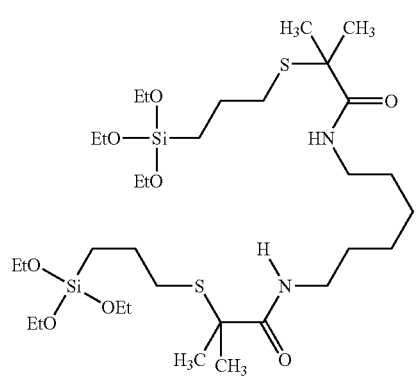
(221)

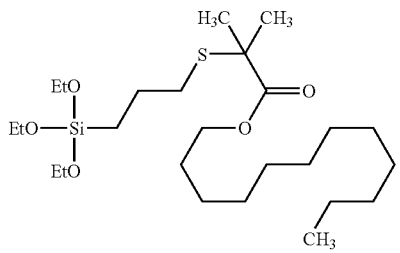
(222)

The preparation of the compounds of the formula I, wherein m is 0, is disclosed for example in WO-A-2005/059022. The preparation of the compounds of the formula I, wherein m is 1 (sulfoxides) or 2 (sulfones) can be accomplished in per se known matter by, for example, oxidation of the sulfides (m is 0) with an oxidizing reagent such as for example a peroxide. The sulfoxides and sulfones can also be formed in-situ while compounding the rubber with the filler.

The process of the present invention has the great advantage that the mixing of the three components (a), (b) and (c), and optionally further additives, is possible at a temperature of up to 180° C.

Rubbers (elastomers) are to be understood as meaning macromolecular materials which after considerable deformation under a small load at room temperature rapidly regain approximately their original shape. See also Hans-Georg Elias, "An Introduction to Polymer Science", Section 12. "Elastomers", pp. 388-393, 1997, VCH Verlagsgesellschaft mbH, Weinheim, Germany or "Ullmann's Encyclopedia of Industrial Chemistry, fifth, completely revised edition, Volume A 23", pp. 221-440 (1993).

Examples of rubbers which may be present in the process of the invention are the following materials:
1. Polymers of conjugated dienes, for example polybutadiene or polyisoprene.
2. Copolymers of mono-and diolefins with one another or with other vinyl monomers, e.g. propylene-isobutylene copolymers, propylene-butadiene copolymers, isobutylene-isoprene copolymers, ethylene-alkyl acrylate copolymers, ethylene-alkyl methacrylate copolymers, ethylene-vinyl acetate copolymers, acrylonitrile-butadiene copolymers, and also terpolymers of ethylene with propylene and with a diene, such as hexadiene, dicyclopentadiene or ethylidenenorbornene.
3. Copolymers of styrene or α-methylstyrene with dienes or with acrylic derivatives, e.g. styrene-butadiene, styrene-butadiene-isoprene, styrene-butadiene-alkyl acrylate and styrene-butadiene-alkyl methacrylate; block copolymers of styrene, e.g. styrene-butadiene-styrene, styrene-isoprene-styrene and styrene-ethylenebutylene-styrene.
4. Halogen-containing polymers, e.g. polychloroprene, chlorinated rubber, chlorinated or brominated copolymers of isobutylene-isoprene (halobutyl rubber), halogenated copolymers of isobutylene and p-methylstyrene.
5. Natural rubber.

Preferably, the rubber component is based on highly unsaturated rubbers such as, for example, natural rubber and/or styrene-butadiene rubber and/or butadiene rubber. Preferably, natural rubbers are used for production of truck tires.

Representative of the highly unsaturated polymers that can be employed in the practice of this invention are diene rubbers. Such rubbers will ordinarily possess an iodine number of between about 20 to about 450, although highly unsaturated rubbers having a higher or a lower (e.g. of 50-100) iodine number can also be employed. Illustrative of the diene rubbers that can be utilized are polymers based on conjugated dienes such as, for example, 1,3-butadiene; 2-methyl-1,3-butadiene; 1,3-pentadiene; 2,3-dimethyl-1,3-butadiene; and the like, as well as copolymers of such conjugated dienes with monomers such as, for example styrene, α-methylstyrene, acetylene, e.g. vinyl acetylene, acrylonitrile, methacrylate, methyl acrylate, ethyl acrylate, methyl methacrylate, ethyl methacrylate, vinyl acetate, and the like. Preferred highly unsaturated rubbers include natural rubber, cis-polyisoprene, polybutadiene, polystyrene-butadiene), styrene-isoprene copolymers, isoprene-butadiene copolymers, styrene-isoprene-butadiene tripolymers, poly -chloroprene, chloro-isobutene-isoprene, nitrile-chloroprene, styrene-chloroprene, and poly-(acrylonitrile -butadiene). Moreover, mixtures of two or more highly unsaturated rubbers with elastomers having lesser unsaturation such as EPDM, EPR, butyl or halogenated butyl rubbers are also within the contemplation of the invention.

In the present application, "reinforcing" white filler is to be understood to mean a white filler capable of reinforcing alone, without any means other than an intermediate coupling agent, a rubber composition intended for the manufacture of tires. In other words the reinforcing white filler is capable of replacing a conventional carbon black filler in its reinforcing function.

Preferably, the reinforcing white filler is silica ($SiO_2$) or alumina ($Al_2O_3$), or a mixture of these two fillers.

The silica used may be any reinforcing silica known to the person skilled in the art, in particular any precipitated or pyrogenic silica having a BET surface area and a specific CTAB surface area both of which are less than 450 $m^2/g$. The highly dispersable precipitated silicas are preferred, in particular when the invention is used to manufacture tires having a low rolling resistance. "Highly dispersible silica" is understood to mean any silica having a very substantial ability to disagglomerate and to disperse in a polymer matrix, which can be observed in known manner by electron or optical microscopy on thin sections. Non-limiting examples of such preferred highly dispersible silicas, include the silica Perkasil KS 430® from Akzo, the silica BV 3380® from Degussa, the silicas Zeosil 1165 MP® and Zeosil 1115 MP® from Rhône-Poulenc, the silica Hi-Sil 2000® from PPG, the silicas Zeopol 8741® or Zeopol 8745® from Huber, and treated precipitated silicas such as, for example, the aluminium-"doped" silicas described in EP-A-0 735 088.

Preferably, the reinforcing alumina is a highly dispersable alumina having a BET surface area from 30 to 400 m$^2$/g, more preferably 80 to 250 m$^2$/g, an average particle size of at most 500 nm, more preferably at most 200 nm, a high amount of reactive Al—OH surface functions, as described in EP-A-0 810 258. Non-limitative examples of such reinforcing aluminas are in particular the aluminas A125®, CR125® and D65CR® of Baikowski.

The physical state in which the reinforcing white filler is present is immaterial, whether it be in the form of a powder, microbeads, granules or balls. The "reinforcing white filler" is also understood to mean mixtures of different reinforcing white fillers, in particular highly dispersible silicas and/or aluminas such as described above.

The reinforcing white filler may also be used in a blend (mixture) with carbon black. Suitable carbon blacks are all the carbon blacks, in particular carbon blacks of the type HAF, ISAF or conventionally used in tires and, particularly, in treads for tires. Non-limiting examples of such blacks, include the blacks N115, N134, N234, N339, N347 and N375. The quantity of carbon black present in the total reinforcing filler may vary within wide limits, this quantity preferably being less than the quantity of reinforcing white filler present in the composition.

Component (b) is usefully added to the rubber in amounts of from 1 to 80%, for example from 1 to 60%, preferably from 5 to 50%, based on the weight of the rubber.

Component (c) is usefully added to the rubber in amounts of from 0.01 to 10%, for example from 0.1 to 10%, preferably from 0.5 to 8%, based on the weight of the rubber.

In addition to components (a), (b) and (c), the process of the invention may comprise further additives, such as the following:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert -butyl-4-methoxymethylphenol, nonylphenols which are linear or branched in the side chains, for example 2,6-di-nonyl-4-methylphenol, 2,4-dimethyl-6-(1'-methylundec-1'-yl)phenol, 2,4-dimethyl-6-(1'-methylheptadec-1'-yl) phenol, 2,4-dimethyl-6-(1'-methyltridec-1'-yl)phenol and mixtures thereof.

1.2. Alkylthiomethylphenols, for example 2,4-dioctylthiomethyl-6-tert -butylphenol, 2,4-dioctylthiomethyl-6-methylphenol, 2,4-dioctylthiomethyl-6-ethylphenol, 2,6-di -dodecylthiomethyl-4-nonylphenol, 2,4-didodecylthiomethyl-6-methylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis (3,5-di -tert-butyl-4-hydroxyphenyl)adipate.

1.4. Tocopherols, for example α-tocopherol, β-tocopherol, γ-tocopherol, δ-tocopherol and mixtures thereof (vitamin E).

1.5. Hydroxylated thiodiphenyl ethers, for example 2,2'-thiobis(6-tert -butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)-disulfide.

1.6. Alkylidenebis-and polyphenols, for example 2, 2'-methylenebis(6-tert-butyl-4-methylphenol), 2,2'-methylenebis (6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis [6-α-methylbenzyl)-4-nonylphenol], 2,2'-methylenebis[6-(α,α-dimethylbenzyl)-4-nonylphenol], 4,4'-methylenebis(2, 6-di-tert-butylphenol), 4,4'-methylenebis(6-tert-butyl-2-methylphenol), 1,1-bis-(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl)dicyclopentadiene, bis[2-(3'-tert-butyl-2'-hydroxy-5'-methylbenzyl)-6-tert -butyl-4-methylphenyl]terephthalate, 1,1-bis-(3, 5-dimethyl-2-hydroxyphenyl)butane, 2,2-bis(3,5-di-tert -butyl-4-hydroxyphenyl)propane, 2,2-bis-(5-tert-butyl-4-hydroxy-2-methylphenyl)-4-n -dodecylmercaptobutane, 1,1,5, 5-tetra(5-tert-butyl-4-hydroxy-2-methylphenyl)pentane, butylated reaction product of p-cresol and dicyclopentadiene.

1.7. O-, N-and S-benzyl compounds, for example 3, 5,3', 5'-tetra-tert-butyl -4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert -butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis(3,5-di -tert-butyl-2-hydroxybenzyl)malonate, di-octadecyl-2-(3-tert-butyl-4-hydroxy-5-methylbenzyl)malonate, di -dodecylmercaptoethyl-2,2-bis(3,5-di-tert-butyl-4-hydroxybenzyl)malonate, bis[4-(1,1,3,3-tetramethylbutyl) phenyl]-2,2-bis(3,5-di-tert-butyl-4-hydroxybenzyl) malonate.

1.9. Aromatic hydroxybenzyl compounds, for example 1,3,5-tris(3,5-di-tert -butyl-4-hydroxybenzyl)-2,4,6-trimethylbenzene, 1,4-bis(3,5-di-tert-butyl-4-hydroxybenzyl)-2,3, 5,6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris(3,5-di -tert-butyl-4-hydroxybenzyl)isocyanurate, 1,3,5-tris(4-tert-butyl-3-hydroxy-2,6-dimethylbenzyl)isocyanurate, 2,4, 6-tris-(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert -butyl-4-hydroxybenzylphosphonate, dioctadecyl-5-tert-butyl-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono-or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, evelinlene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.14. Esters of β-(5-tert-butyl-4-hydroxy-3-methylphenyl) propionic acid with mono-or poly-hydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]-undecane.

1.15. Esters of β-(3,5-dicyclohexyl-4-hydroxyphenyl)propionic acid with mono-or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.16. Esters of 3,5-di-tert-butyl-4-hydroxyphenyl acetic acid with mono-or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl] propionyloxy)ethyl]oxamide.

1.18. Ascorbic Acid (Vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis (4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino] ethane, 1,2-bis(phenylamino)propane, (o-tolyl)biguanide, bis[4-(1,3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazine, N,N,N',N'-tetraphenyl-1,4-diaminobut-2-ene.

1.20. Quinoline derivatives, for example polymerized 2,2, 4-trimethyl-1,2-dihydroquinoline, 6-ethoxy-2,2,4-trimethyl-1,2-dihydroquinoline.

2. UV Absorbers and Light Stabilizers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis(α,α-dimethylbenzyl)-2'-hydroxyphenyl)benzotriazole, 2-(3'-tert-butyl-2'-hydroxy-5'-(2-octyloxycarbonylethyl)phenyl)-5-chlorobenzotriazole, 2-(3'-tert -butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl) phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl) benzotriazole, 2-(3'-dodecyl-2'-hydroxy-5'-methylphenyl) benzotriazole, 2-(3'-tert-butyl-2'-hydroxy-5'-(2-isooctyloxycarbonylethyl)phenylbenzotriazole, 2,2'-methylenebis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H -benzotriazole with polyethylene glycol 300;

where R=3'-tert-butyl-4'-hydroxy-5'-2H-benzotriazol-2-ylphenyl, 2-[2'-hydroxy-3'-(α,α-dimethylbenzyl)-5'-(1,1,3, 3-tetramethylbutyl)phenyl]benzotriazole; 2-[2'-hydroxy-3'-(1,1,3,3-tetramethylbutyl)-5'-(α,α-dimethylbenzyl)phenyl]-benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert -butylphenyl salicylate, phenyl salicylate, octylphenyl salicylate, dibenzoyl resorcinol, bis(4-tert -butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethylbutyl)phenol], such as the 1:1 or 1:2 complex, with or without additional ligands such as n -butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis-(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl)n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert -octylamino-2,6-di-chloro-1,3,5-triazine, tris(2,2,6,6-tetramethyl-4-piperidyl) nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di -tert-butylbenzyl)-malonate, 3-n-octyl-7,7,9,9-tetramethyl-1,3,8-triazaspiro[4.5]decane-2,4-dione, bis(1-octyl-oxy-2,2,6,6-tetramethylpiperidyl)sebacate, bis(1-octyloxy-2,2,6,6-tetramethylpiperidyl)succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro -4,6-bis(4-n-butylamino-2,2,6,6-tetramethylpiperidyl)-1,3,5-triazine and 1,2-bis(3-aminopropylamino)-ethane, the condensate of 2-chloro-4,6-di-(4-n-butylamino-1,2,2,6,6-pentamethylpiperidyl)-1,3,5-triazine and 1,2-bis (3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl) pyrrolidine -2,5-dione, a mixture of 4-hexadecyloxy-and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxo-spiro-[4,5]decane, a reaction product of 7,7,9,9-tetramethyl-2-cycloundecyl-1-oxa-3,8-diaza-4-oxo-spiro-[4,5]decane and epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl)-hexamethylenediamine, a diester of 4-methoxymethylenemalonic acid with 1,2,2,6,6-pentamethyl-4-hydroxypiperidine, poly [methylpropyl-3-oxy-4-(2,2,6,6-tetramethyl-4-piperidyl)]siloxane, a reaction product of maleic acid anhydride-α-olefin copolymer with 2,2,6,6-tetramethyl -4-aminopiperidine or 1,2,2,6,6-pentamethyl-4-aminopiperidine, 2,4-bis[N -(1-cyclohexyloxy-2,2,6,6-tetramethylpiperidine-4-yl)-N-butylamino]-6-(2-hydroxyethyl)amino -1,3,5-triazine, 1-(2-hydroxy-2-methylpropoxy)-4-octadecanoyloxy-2,2,6,6-tetramethylpiperidine, 5-(2-ethylhexanoyl)oxymethyl-3,3,5-trimethyl-2-morpholinone, Sanduvor (Clariant; CAS Reg. No. 106917-31-1], 5-(2-ethylhexanoyl)oxymethyl-3,3,5-trimethyl-2-morpholinone, the reaction product of 2,4-bis[(1-cyclohexyloxy-2,2,6,6-piperidine-4-yl)butylamino]-6-chloro-s-triazine with N,N'-bis(3-aminopropyl) ethylenediamine), 1,3,5-tris(N-cyclohexyl-N-(2,2,6,6-tetramethylpiperazine-3-one-4-yl)amino)-s-triazine, 1,3,5-tris(N-cyclohexyl-N-(1,2,2,6,6-pentamethylpiperazine-3-one-4-yl)amino)-s-triazine.

2.7. Oxamides, for example 4, 4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o-and p -methoxy-disubstituted oxanilides and mixtures of o-and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis (2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy) phenyl-4,6-diphenyl-1,3,5-triazine, 2-(2-hydroxy-4-methoxyphenyl)-4,6-diphenyl-1,3,5-triazine, 2,4,6-tris[2-hydroxy -4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearylpentaerythritol diphosphite, tris(2,4-di-tert-butylphenyl)phosphite, diisodecyl pentaerythritol diphosphite, bis(2,4-di-tert-butylphenyl)pentaerythritol diphosphite, bis(2,4-di-cumylphenyl)pentaerythritol diphosphite, bis(2,6-di-tert-butyl-4-methylphenyl)pentaerythritol diphosphite, diisodecyloxypentaerythritol diphosphite, bis (2,4-di-tert-butyl-6-methylphenyl)-pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-dibenz[d,g]-1,3,2-dioxaphosphocin, 2,2',2"-nitrilo-[triethyltris(3,3',5,5'-tetra-tert-butyl-1,1'-biphenyl-2,2'-diyl) phosphite], 2-ethylhexyl(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

5. Hydroxylamines, for example N,N-dibenzylhydroxylamine, N,N-diethylhydroxylamine, N,N -dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxyylamine, N-heptadecyl-N-octadecylhydroxylamine, N,N-dialkylhydroxylamine derived from hydrogenated tallow amine.

6. Nitrones, for example N-benzyl-alpha-phenylnitrone, N-ethyl-alpha-methylnitrone, N -octyl-alpha-heptylnitrone, N-lauryl-alpha-undecylnitrone, N-tetradecyl-alpha-tridecylnitrone, N-hexadecyl-alpha -pentadecylnitrone, N-octadecyl-alpha-heptadecylnitrone, N-hexadecyl-alpha-heptadecylnitrone, N-ocatadecyl-alpha-pentadecylnitrone, N-heptadecyl-alpha-heptadecylnitrone, N-octadecyl-alpha-hexadecylnitrone, nitrone derived from N,N-dialkylhydroxylamine derived from hydrogenated tallow amine.

7. Thiosynergistic compounds, for example thiodipropionic acid dilauryl ester or thiodipropionic acid distearyl ester or compounds of formula IV

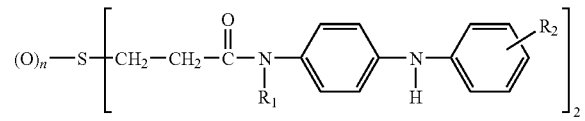
(IV)

wherein
R$_1$ is hydrogen, C$_1$-C$_{12}$alkyl, cyclohexyl, phenyl or benzyl,
R$_2$ is hydrogen or C$_1$-C$_4$alkyl, and
n is the number 0, 1 or 2.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Basic co-stabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.

10. Other additives, for example plasticisers, lubricants, emulsifiers, pigments, rheology additives, catalysts, flow-control agents, optical brighteners, flameproofing agents, antistatic agents and blowing agents.

11. Benzofuranones and indolinones, for example those disclosed in U.S. Pat. Nos. 4,325,863; 4,338,244; 5,175,312; 5,216,052; 5,252,643; DE-A-4316611; DE-A-4316622; DE-A-4316876; EP-A-0589839; EP-A-0591102 or EP-A-1291384 or 3-[4-(2-acetoxyethoxy)phenyl]-5,7-di-tert-butylbenzofuran-2-one, 5,7-di-tert-butyl -3-[4-(2-stearoyloxyethoxy)phenyl]benzofuran-2-one, 3,3'-bis[5,7-di-tert-butyl-3-(4-[2-hydroxyethoxy]phenyl)-benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3, 4-dimethylphenyl)-5,7-di-tert -butylbenzofuran-2-one, 3-(2, 3-dimethylphenyl)-5,7-di-tert-butylbenzofuran-2-one or 3-(2-actyl-5-isooctylphenyl)-5-isoocylbenzofuran-2-one.

Preferred processes of the invention comprise, as other additives, one or more components selected from the group consisting of pigments, dyes, leveling assistants, dispersants, plasticizers, vulcanization activators, vulcanization accelerators, vulcanizers, charge control agents, adhesion promoters, light stabilizers or antioxidants, such as phenolic antioxidants (items 1.1 to 1.18 in the list) or aminic antioxidants (item 1.19 in the list), organic phosphites or phosphonites (item 4 in the list) and/or thiosynergists (item 7 in the list).

An example of the concentrations at which these other additives are added is from 0.01 to 10%, based on the total weight of the elastomer.

Components (b) and (c), and also, if desired, other additives are incorporated into the rubber in one-step, for example during mixing in internal mixers with rams (Banburry), on mixing rolls or in mixing extruders, prior to vulcanization. When added to the rubber, components (b) and (c) and, if desired, other additives may also be in the form of a masterbatch comprising these, for example at a concentration of from 2.5 to 25% by weight.

Components (b) and (c) and, if desired, other additives may be in pure form or encapsulated in waxes, in oils or in polymers when they are incorporated into the rubber to be treated. Components (b) and (c) can also be used in form of surface modified silica.

The resultant rubbers may be used in a wide variety of forms, e.g. ribbons, moulding compositions, profiles, conveyor belts or tires (pneumatic).

The present invention further provides novel compounds of the formula Ia

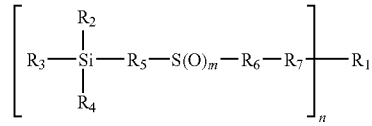
(Ia)

wherein, when n is 1,
R$_1$ is hydrogen, C$_1$-C$_{25}$alkyl, C$_1$-C$_{25}$alkyl substituted with furyl, morpholine, C$_1$-C$_4$dialkylamino, C$_1$-C$_4$trialkylammonium or M$^+$ $^-$O$_3$S—; C$_2$-C$_{25}$alkyl interrupted by oxygen; C$_5$-C$_{12}$cycloalkyl, C$_2$-C$_{25}$alkenyl, unsubstituted or $C_1$-$C_4$alkyl-substituted phenyl; $C_7$-$C_{12}$phenoxyalkyl, unsubstituted or $C_1$-$C_4$alkyl substituted $C_7$-$C_9$bicycloalkyl;

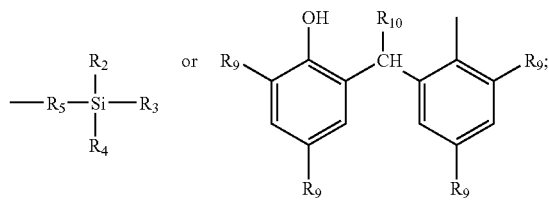

when n is 2, $R_1$ is $C_1$-$C_{25}$alkylene, $C_1$-$C_{25}$alkylene substituted with $C_1$-$C_4$alkyl; $C_2$-$C_{25}$alkylene substituted with $C_1$-$C_4$alkyl and interrupted by oxygen; $C_2$-$C_{25}$alkylene interrupted by oxygen, sulfur, phenylene or cyclohexylene;

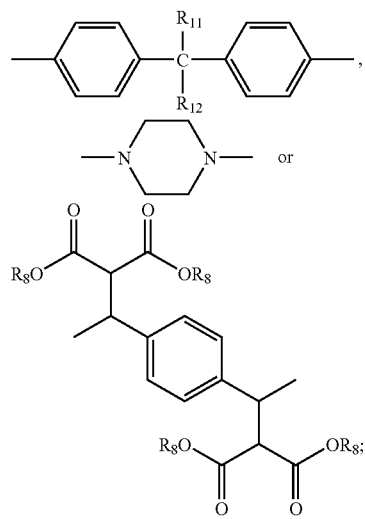

or when $R_6$ and $R_7$ are a direct bond, $R_1$ is

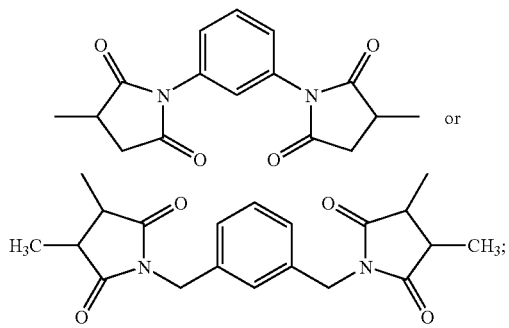

$R_2$, $R_3$ and $R_4$ are each independently of the others $C_1$-$C_{25}$alkyl, $C_2$-$C_{25}$alkyl interrupted by oxygen; $C_5$-$C_{12}$cycloalkyl, $C_2$-$C_{25}$alkenyl, unsubstituted or $C_1$-$C_4$alkyl-substituted phenyl, $C_7$-$C_9$phenylalkyl, $C_1$-$C_{25}$alkoxy, $C_3$-$C_{25}$alkoxy interrupted by oxygen; $C_5$-$C_{12}$cycloalkoxy, $C_2$-$C_{25}$alkenyloxy, unsubstituted or $C_1$-$C_4$alkyl-substituted phenoxy, $C_7$-$C_9$phenylalkoxy, halogen, $C_2$-$C_{25}$alkanoyloxy or unsubstituted or $C_1$-$C_4$alkyl substituted benzoyloxy; with the proviso that at least one of $R_2$, $R_3$ or $R_4$ is $C_1$-$C_{25}$alkoxy, $C_3$-$C_{25}$alkoxy interrupted by oxygen; $C_5$-$C_{12}$cycloalkoxy, $C_2$-$C_{25}$alkenyloxy, unsubstituted or $C_1$-$C_4$alkyl-substituted phenoxy, $C_7$-$C_9$phenylalkoxy, halogen, $C_2$-$C_{25}$alkanoyloxy or unsubstituted or $C_1$-$C_4$alkyl substituted benzoyloxy;

$R_5$ is $C_1$-$C_{25}$alkylene, $C_5$-$C_{12}$cycloalkylene, unsubstituted or $C_1$-$C_4$alkyl substituted phenylene;

$R_6$ is a direct bond, $C_1$-$C_{25}$alkylene substituted with $C_1$-$C_{25}$alkyl, $C_2$-$C_{25}$alkoxycarbonyl, $C_3$-$C_{25}$-alkoxycarbonylalkyl or phenyl;

$R_7$ is a direct bond or

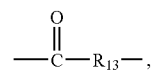

with the proviso that, when $R_7$ is a direct bond and n is 1, $R_6$ is not a direct bond; and with the proviso that, when $R_7$ is

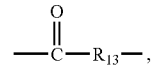

$R_6$ is not a direct bond;

$R_8$ is $C_1$-$C_{25}$alkyl, $C_2$-$C_{25}$alkyl interrupted by oxygen; $C_5$-$C_{12}$cycloalkyl, $C_2$-$C_{25}$alkenyl, $C_2$-$C_{25}$alkinyl, $C_7$-$C_9$-phenylalkyl, unsubstituted or $C_1$-$C_4$alkyl-substituted phenyl, $R_9$ is $C_1$-$C_5$alkyl, $R_{10}$ is hydrogen or $C_1$-$C_4$alkyl, $R_{11}$ and $R_{12}$ are each independently of the other hydrogen, $CF_3$, $C_1$-$C_{12}$alkyl or phenyl, or $R_{11}$ and $R_{12}$, together with the carbon atom to which they are bonded, form a $C_5$-$C_8$-cycloalkylidene ring that is unsubstituted or substituted by from 1 to 3 $C_1$-$C_4$alkyl groups, $R_{13}$ is oxygen or —N($R_{14}$)—, $R_{14}$ is hydrogen or $C_1$-$C_{12}$alkyl, M is sodium, potassium or ammonium, n is 1 or 2; or an oligomeric hydrolysis product of the compound of the formula Ia.

Of special interest are the compounds of the formula Ia, wherein when n is 1, $R_1$ is hydrogen, $C_1$-$C_{18}$alkyl, $C_1$-$C_4$alkyl substituted with furyl, morpholine, $C_1$-$C_4$dialkylamino, $C_1$-$C_4$trialkylammonium or $M^+$ $^-O_3S$—; $C_2$-$C_6$alkyl interrupted by oxygen; cyclohexyl, $C_4$-$C_{10}$alkenyl, phenyl; $C_7$-$C_9$phenoxyalkyl, unsubstituted or $C_1$-$C_4$alkyl substituted $C_7$-$C_9$bicycloalkyl; or

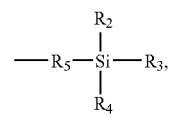

when n is 2, $R_1$ is $C_2$-$C_6$alkylene, $C_2$-$C_4$alkylene substituted with methyl; $C_4$-$C_8$alkylene substituted with methyl and interrupted by oxygen; $C_4$-$C_8$alkylene interrupted by oxygen;

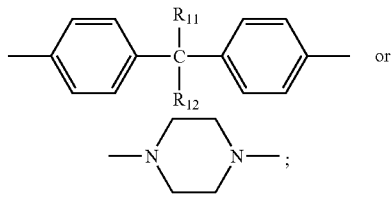

$R_2$, $R_3$ and $R_4$ are each independently of the others $C_1$-$C_4$alkyl or $C_1$-$C_4$alkoxy; with the proviso that at least one of $R_2$, $R_3$ or $R_4$ is $C_1$-$C_4$alkoxy;

$R_5$ is $C_2$-$C_4$alkylene, $R_6$ is $C_1$-$C_3$alkylene substituted with methyl, $C_2$-$C_3$alkoxycarbonyl, $C_3$-$C_6$alkoxycarbonylalkyl or phenyl;

$R_7$ is

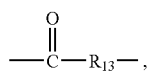

$R_{11}$ and $R_{12}$ are each independently of the other hydrogen or $C_1$-$C_4$alkyl, $R_{13}$ is oxygen or —N($R_{14}$)—, $R_{14}$ is hydrogen, M is potassium, m is 0 or 1, and n is 1 or 2; or an oligomeric hydrolysis product of the compound of the formula Ia.

Of very special interest are the new compounds of the formula Ia wherein when n is 1, $R_1$ is hydrogen, $C_1$-$C_{18}$alkyl, $C_1$-$C_4$alkyl substituted with furyl, morpholine, $C_1$-$C_4$dialkylamino, $C_1$-$C_4$trialkylammonium or $M^+$ $^-O_3S$—; $C_2$-$C_6$alkyl interrupted by oxygen; cyclohexyl, $C_4$-$C_{10}$alkenyl, phenyl; $C_7$-$C_9$phenoxyalkyl, unsubstituted or $C_1$-$C_4$alkyl substituted $C_7$-$C_9$bicycloalkyl; or

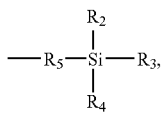

when n is 2, $R_1$ is $C_2$-$C_6$alkylene, $C_2$-$C_4$alkylene substituted with methyl; $C_4$-$C_8$alkylene substituted with methyl and interrupted by oxygen; $C_4$-$C_8$alkylene interrupted by oxygen;

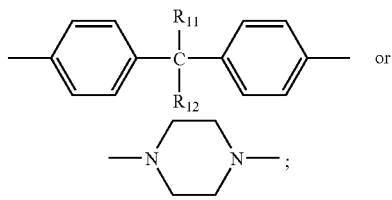

$R_2$, $R_3$ and $R_4$ are each independently of the others $C_1$-$C_4$alkyl or $C_1$-$C_4$alkoxy; with the proviso that at least one of $R_2$, $R_3$ or $R_4$ is $C_1$-$C_4$alkoxy;

$R_5$ is $C_2$-$C_4$alkylene, $R_6$ is $C_1$-$C_3$alkylene; or $C_1$-$C_3$alkylene substituted with methyl, $C_2$-$C_3$alkoxycarbonyl, $C_3$-$C_6$-alkoxycarbonylalkyl or phenyl;

$R_7$ is

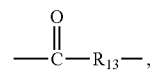

$R_{11}$ and $R_{12}$ are each independently of the other hydrogen or $C_1$-$C_4$alkyl, $R_{13}$ is oxygen or —N($R_{14}$)—, $R_{14}$ is hydrogen, M is potassium, m is 1 or 2, and n is 1 or 2; or an oligomeric hydrolysis product of the compound of the formula Ia.

The preferred meanings of the general symbols in the novel compounds of the formula Ia are the same as the preferred meanings of the general symbols set out in relation to the new process of the invention.

The present invention further provides a composition comprising a) a rubber susceptible to oxidative, thermal, dynamic light-induced and/or ozone-induced degradation, b) a white reinforcing filler, and c) a coupling agent of the formula Ia.

Additionally, the present invention provides a process for ensuring the coupling of a white reinforcing filler to rubber compositions reinforced by a white filler, which comprises incorporating into the rubber at least one coupling agent of the formula Ia and then vulcanizing the composition.

A further embodiment of the present invention is the use of the compound of the formula Ia as coupling agent for ensuring the coupling of a white reinforcing filler with a rubber.

The preferred compounds of the formula I [component (c)] for the process and use listed above are the same as those for the compositions of the invention.

The Examples below further illustrate the invention. Data in parts or percentages are based on weight.

EXAMPLE 1

Preparation of Compound 162

A mixture of butyl 2-bromoisobutyrate (35.0 g, 157 mmol), 3-mercaptopropyltriethoxysilane (39.4 g, 157 mmol) and solid potassium carbonate (43.4 g, 314 mmol) in methyl ethyl ketone (MEK) (160 ml) is heated under reflux and under nitrogen for 22 hours. Water is then added and the product is extracted in toluene. The organic phase is washed with 1M NH4Cl, NaCl, dried over sodium sulfate, filtered and evaporated to dryness using a rotary evaporator to afford a crude product as a pale yellow liquid. The crude product is purified by distillation (oil bath temp. 195° C.; over-head temp. 125-135° C.; vacuum: 0.01-0.1 mbar) to afford 42.5 g (71%) of compound 162 as a clear colorless liquid.

$^1$H-NMR (300 MHz, CDCl$_3$): δ=4.11 (t, J=6.6 Hz, CO$_2$CH$_2$, 2H); 3.90-3.75 (m, SiOCH$_2$, 6H); 2.62 (t, J=7.2 Hz, SCH$_2$, 2H); 1.75-1.55 (m, SCH$_2$CH$_2$+CO$_2$CH$_2$CH$_2$, 4H); 1.50 (s, CH$_3$, 6H), 1.50-1.30 (m, CO$_2$CH$_2$CH$_2$CH$_2$, 2H); 1.30-1.15 (m, SiOCH$_2$CH$_3$, 9H); 0.95 (t, J=7.2 Hz, CO$_2$CH$_2$CH$_2$CH$_2$CH$_3$, 3H); 0.80-0.65 (m, SiCH$_2$, 2H).

$^{13}$C-NMR (75 MHz, CDCl$_3$): 174.7 (s); 65.3 (t); 58.8 (t); 47.3 (s); 33.2 (t); 31.0 (t); 26.2 (q); 23.5 (t); 19.5 (t); 18.7 (q); 14.1 (q); 10.7 (t).

EXAMPLE 2

Preparation of Compound 163

A mixture of hexyl 2-bromoisobutyrate (24.6 g, 97.9 mmol), 3-mercaptopropyltriethoxysilane (23.3 g, 97.9 mmol) and solid potassium carbonate (27.1 g, 196 mmol) in methyl ethyl ketone (MEK) (100 ml) is heated under reflux and under nitrogen for 22 hours. Water is then added and the product is extracted in toluene. The organic phase is washed with 1M NH$_4$Cl, NaCl, dried over sodium sulfate, filtered and evaporated to dryness using a rotary evaporator to afford a crude product as a turbid pale yellow liquid. The crude product is purified by distillation (oil bath temp. 210° C.; overhead temp. 150° C.; 0.01-0.1 mbar) to afford 26.1 g (65%) of compound 163 as a clear colorless liquid.

$^1$H-NMR (300 MHz, CDCl$_3$): δ=4.10 (t, J=6.6 Hz, CO$_2$CH$_2$, 2H); 3.90-3.75 (m, SiOCH$_2$, 6H); 2.63 (t, J=7.2 Hz, SCH$_2$, 2H); 1.75-1.55 (m, SCH$_2$CH$_2$+CO$_2$CH$_2$CH$_2$, 4H); 1.51 (s, CH$_3$, 6H), 1.50-1.15 (m, CH$_2$+SiOCH$_2$CH$_3$, 15H); 0.95-0.85 (m, CH$_3$, 3H); 0.80-0.65 (m, SiCH$_2$, 2H).

$^{13}$C-NMR (100 MHz, CDCl$_3$): 174.3 (s); 65.2 (t); 58.4 (t); 46.9 (s); 32.8 (t); 31.4 (t); 28.5 (t); 25.8 (q); 25.6 (t); 23.1 (t); 22.5 (t); 18.3 (q); 14.0 (q); 10.3 (t).

EXAMPLE 3

Preparation of Compound 164

To toluene (1.5 l) is added at 10° C. and under a weak stream of nitrogen solid sodium ethanolate (48.7 g, 0.68 mol), followed by addition of 3-mercaptopropyltriethoxysilane (170.7 g, 0.72 mol) within 20 minutes. The reaction mixture is stirred for 15 minutes at 15° C., then octyl 2-bromoisobutyrate (200 g, 0.72 mol) is added dropwise over 1 h at 15° C. After 30 minutes of stirring at room temperature, water (500 ml) is added to the reaction mass. The aqueous phase is separated and the organic phase is washed with NaCl (2×350 ml), dried over sodium sulfate, filtered and evaporated to dryness using a rotary evaporator to afford a crude product as a turbid yellow liquid. The crude product is purified by distillation (oil bath temp. 200° C.; overhead temp. 145-155° C.; 0.01-0.1 mbar) to afford 191 g (64%) of compound 164 as a clear colorless liquid.

$^1$H-NMR (400 MHz, CDCl$_3$): δ=4.11 (t, J=6.8 Hz, CO$_2$CH$_2$, 2H); 3.82 (q, J=6.8 Hz, SiOCH$_2$, 6H); 2.63 (t, J=7.6 Hz, SCH$_2$, 2H); 1.72-1.55 (m, SCH$_2$CH$_2$+CO$_2$CH$_2$CH$_2$, 4H); 1.51 (s, CH$_3$, 6H), 1.50-1.18 (m, CH$_2$+SiOCH$_2$CH$_3$, 19H); 0.89 (t, J=6.8 Hz, CH$_3$, 3H); 0.78-0.68 (m, SiCH$_2$, 2H).

$^{13}$C-NMR (100 MHz, CDCl$_3$): 174.3 (s); 65.3 (t); 58.4 (t); 46.9 (s); 32.8 (t); 31.8 (t); 29.2 (t); 28.6 (t); 25.9 (t); 25.8 (q); 23.1 (t); 22.6 (t); 18.3 (q); 14.1 (q); 10.3 (t).

EXAMPLE 4

Preparation of a Four Component Mixture of Compounds 164, 173, 174 and 175

To 1-octanol (118 g, 904 mmol) is added portionwise at 70° C. and under a weak stream of nitrogen sodium (2.10 g, 91.6 mmol). The reaction is stirred for 2 hours at 70° C. and then 30 minutes at 110° C. The reaction is cooled down to 5° C. and 2-bromoisobutyrylbromide (10.5 g, 45.8 mmol) is added slowly. The reaction mixture is stirred for 90 minutes at room temperature, after which time the reaction was cooled down to 10° C. and 3-mercaptopropyltriethoxysilane (10.9 g, 45.8 mmol) is added. The reaction mixture is stirred for 12 hours at room temperature, then water (100 ml) is added and the product is extracted in toluene (350 ml). The organic phase is washed with water (3×), dried over sodium sulfate, filtered and evaporated to dryness using a rotary evaporator to afford a crude product as a pale yellow liquid. The crude product is purified by distilling off 1-octanol (oil bath temp. 190° C.; 0.05-0.1 mbar) to afford 21.5 g of a pale yellow liquid containing 12% (GC) of compound 164, 37% (GC) of compound 173, 34% (GC) of compound 174 and 10% (GC) of compound 175.

Physicochemical data for compound 164 see end of Example 3.

Compound 173: $^1$H-NMR (300 MHz, CDCl$_3$): δ=4.10 (t, J=6.6 Hz, CO$_2$CH$_2$, 2H); 3.80 (q, J=6.9 Hz, SiOCH$_2$CH$_3$, 4H); 3.72 (t, J=6.6 Hz, SiOCH$_2$CH$_2$, 2H); 2.62 (t, J=7.5 Hz, SCH$_2$, 2H); 1.75-1.45 (m, SCH$_2$CH$_2$+CO$_2$CH$_2$CH$_2$+SiOCH$_2$CH$_2$, 6H); 1.50 (s, CH$_3$, 6H), 1.45-1.20 (m, CH$_2$, 20H); 1.22 (t, J=6.9 Hz, SiOCH$_2$CH$_3$, 6H); 1.00-0.80 (m, CH$_3$, 6H); 0.80-0.65 (m, SiCH$_2$, 2H).

Compound 174: $^1$H-NMR (300 MHz, CDCl$_3$): δ=4.11 (t, J=6.6 Hz, CO$_2$CH$_2$, 2H); 3.81 (q, J=6.9 Hz, SiOCH$_2$CH$_3$, 2H); 3.73 (t, J=6.6 Hz, SiOCH$_2$CH$_2$, 4H); 2.63 (t, J=7.5 Hz, SCH$_2$, 2H); 1.75-1.45 (m, SCH$_2$CH$_2$+CO$_2$CH$_2$CH$_2$+SiOCH$_2$CH$_2$, 8H); 1.51 (s, CH$_3$, 6H), 1.45-1.20 (m, CH$_2$, 30H); 1.23 (t, J=6.6 Hz, SiOCH$_2$CH$_3$, 3H); 1.00-0.80 (m, CH$_3$, 9H); 0.80-0.65 (m, SiCH$_2$, 2H).

EXAMPLE 5

Preparation of a Six Component Mixture of Compounds 165, 166, 167, 168, 169 and 170

To 1-octanol (150 g, 1.15 mol) is added portionwise at 90° C. and under a weak stream of nitrogen sodium (2.63 g, 115 mmol). The reaction mixture is stirred for 60 minutes and then cooled down to room temperature. 3-mercaptopropyltriethoxysilane (28.7 g, 115 mmol) is added and the reaction mixture stirred for one hour. Ethyl 2-bromoisobutyrate (23.0 g, 115 mmol) is added slowly to keep the reaction temperature around 20-25° C. The reaction mixture is stirred for 12 hours at room temperature, then water (100 ml) is added and the product is extracted in toluene (350 ml). The organic phase is washed with water (3×), dried over sodium sulfate, filtered and evaporated to dryness using a rotary evaporator to afford a crude product as a colourless liquid. The crude product is purified by distilling off 1-octanol (oil bath temp. 190° C.; 0.05-0.1 mbar) to afford 65.9 g of a slightly turbid yellow liquid containing 3% (GC) of compound 165, 12% (GC) of compound 166, 3% (GC) of compound 167, 5% (GC) of compound 168, 22% (GC) of compound 169, and 34% (GC) of compound 170.

EXAMPLE 6

Preparation of a Mixture of Compounds 171 and 172

To 1-hexanol (100 g, 978 mmol) is added portionwise at 60° C. and under a weak stream of nitrogen sodium (2.25 g, 87.8 mmol). The reaction mixture is then heated up to 110° C. and stirred for 30 minutes, after which time the reaction mixture is cooled down to 5° C. 2-bromoisobutyrylbromide (11.6 g, 48.9 mmol) is added slowly and the reaction mixture is stirred for 90 minutes at room temperature. The reaction mixture is then cooled down at 10° C. and 3-mercaptopropyltriethoxysilane (12.3 g, 48.9 mmol) is added. The reaction mixture is stirred for 12 hours at room temperature, then water (100 ml) is added and the product is extracted in toluene (350 ml). The organic phase is washed with NaCl (3×), dried over sodium sulfate, filtered and evaporated to dryness using a rotary evaporator to afford a crude product as a colourless liquid. The crude product is purified by distilling off 1-hexanol (oil bath temperature 200° C.; 0.05-0.1 mbar) to afford 27.2 g of a colourless liquid containing 64% (GC) of compound 171 and 25.5% (GC) of compound 172.

Compound 171: $^1$H-NMR (300 MHz, CDCl$_3$): δ=4.11 (t, J=6.6 Hz, CO$_2$CH$_2$, 2H); 3.72 (q, J=6.6 Hz, SiOCH$_2$, 6H); 2.62 (t, J=7.2 Hz, SCH$_2$, 2H); 1.75-1.45 (m, SCH$_2$CH$_2$+CO$_2$CH$_2$CH$_2$+SiOCH$_2$CH$_2$, 10H); 1.51 (s, CH$_3$, 6H), 1.45-1.20 (m, CH$_2$, 20H); 1.00-0.80 (m, CH$_3$, 12H); 0.80-0.65 (m, SiCH$_2$, 2H).

Compound 172: $^1$H-NMR (300 MHz, CDCl$_3$): δ=4.10 (t, J=6.6 Hz, CO$_2$CH$_2$, 2H); 3.80 (q, J=6.9 Hz, SiOCH$_2$CH$_3$, 2H); 3.72 (t, J=6.6 Hz, SiOCH$_2$CH$_2$, 4H); 2.62 (t, J=7.5 Hz, SCH$_2$, 2H); 1.75-1.45 (m, SCH$_2$CH$_2$+CO$_2$CH$_2$CH$_2$+SiOCH$_2$CH$_2$, 8H); 1.51 (s, CH$_3$, 6H), 1.45-1.20 (m, CH$_2$+SiOCH$_2$CH$_3$, 21H); 1.00-0.80 (m, CH$_3$, 9H); 0.80-0.65 (m, SiCH$_2$, 2H).

EXAMPLE 7

Preparation of Compound 176

To 2,2-dimethyl-1,3-propanediol (13.2 g, 124 mmol) dissolved in tetrahydrofuran (120 ml) is added at 0° C. and under a weak stream of nitrogen triethylamine (30.2 g, 298 mmol), followed by the dropwise addition at 0-10° C. of 2-bromoisobutyrylbromide (58.8 g, 248 mmol). The reaction mixture is stirred for one hour at room temperature, then water (100 ml) is added and the product is extracted in toluene. The organic phase is washed with 1M NH$_4$Cl, NaCl, dried over sodium sulfate, filtered and evaporated to dryness using a rotary evaporator to afford a crude product as an orange liquid. The crude product is purified by distillation (oil bath temp. 190° C.; overhead temp. 120-125° C.; 0.05-0.1 mbar) to afford 32.8 g (66%) of compound A as a pale yellow liquid.

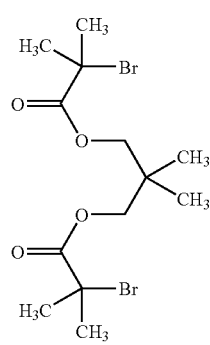

(A)

$^1$H-NMR (300 MHz, CDCl$_3$): δ=4.02 (s, CO$_2$CH$_2$, 4H); 1.94 (s, CH$_3$, 9H); 1.07 (s, CH$_3$, 9H).

A mixture of compound A (30.0 g, 74.6 mmol), 3-mercaptopropyltriethoxysilane (41.2 g, 164 mmol) and solid potassium carbonate (41.2 g, 298 mmol) in methyl ethyl ketone (170 ml) is heated under reflux and under nitrogen for 30 hours. Water is then added and the product is extracted in ethyl acetate. The organic phase is washed with 1M NH$_4$Cl, NaCl, dried over sodium sulfate, filtered and evaporated to dryness using a rotary evaporator to afford a crude product as a pale yellow liquid. The crude product is purified by distilling off the residual volatiles (oil bath temp. 220° C.; 0.05-0.1 mbar) to afford 51.2 g of a yellow liquid containing 93% (GC-purity) of compound 176. $^1$H-NMR (300 MHz, CDCl$_3$): δ=3.93 (s, CO$_2$CH$_2$, 4H); 3.81 (q, J=6.9 Hz, SiOCH$_2$, 12H); 2.61 (t, J=7.5 Hz, SCH$_2$, 4H); 1.75-1.55 (m, SCH$_2$CH$_2$, 4H); 1.51 (s, CH$_3$, 12H); 1.30-1.15 (m, SiOCH$_2$CH$_3$, 18H); 1.02 (s, CH$_3$, 6H); 0.80-0.65 (m, SiCH$_2$, 4H).

EXAMPLE 8

Preparation of Compound 177

A mixture of [6-(2-bromo-2-methyl-propionyloxy)-hexyl]-2-bromoisobutyrate (10.0 g, 24.0 mmol), 3-mercaptopropyltriethoxysilane (12.1 g, 48.0 mmol) and solid potassium carbonate (13.3 g, 96.0 mmol) in methyl ethyl ketone (70 ml) is heated under reflux and under nitrogen for 24 hours. Water is then added and the product is extracted in ethyl acetate. The organic phase is washed with H$_2$O, NaCl, dried over sodium sulfate, filtered and evaporated to dryness using a rotary evaporator to afford a crude product as a clear yellow liquid. The crude product is purified by flash chromatography (hexane/ethyl acetate: 9:1) to afford 5.70 g (GC-purity: 95.4%) of compound 177 as colourless liquid. $^1$H-NMR (400 MHz, CDCl$_3$): δ=4.20-4.05 (m, CO$_2$CH$_2$, 4H); 3.90-3.70 (m, SiOCH$_2$, 12H); 2.70-2.60 (m, SCH$_2$, 4H); 1.80-1.60 (m, SCH$_2$CH$_2$+CO$_2$CH$_2$CH$_2$, 8H); 1.43 (s, CH$_3$, 12H); 1.50-1.35 (m, CO$_2$CH$_2$CH$_2$CH$_2$, 4H); 1.35-1.15 (m, SiOCH$_2$CH$_3$, 18H); 0.80-0.65 (m, SiCH$_2$, 4H). $^{13}$C-NMR (100 MHz, CDCl$_3$): 174.2 (s); 64.9 (t); 58.3 (t); 46.8 (s); 32.7 (t); 28.4 (t); 25.7 (q); 25.5 (t); 23.0 (t); 18.3 (q); 10.2 (t).

EXAMPLE 9

Preparation of Compound 178

A mixture of [2-(2-bromo-2-methyl-propionyloxy)-ethyl]-2-bromoisobutyrate (13.0 g, 36.1 mmol), 3-mercaptopropyltriethoxysilane (17.2 g, 72.2 mmol) and solid potassium carbonate (20.0 g, 144 mmol) in methyl ethyl ketone (100 ml) is heated under reflux and under nitrogen for 24 hours. Water is then added and the product is extracted in ethyl acetate. The organic phase is washed with 1N NH$_4$Cl, NaCl, dried over sodium sulfate, filtered and evaporated to dryness using a rotary evaporator to afford a crude product as a pale yellow suspension. The crude product is purified by flash chromatography (hexane/ethyl acetate: 6:1) to afford 10.4 g (GC-purity: 94.7%) of compound 178 as colourless liquid. $^1$H-NMR (400 MHz, CDCl$_3$): δ=4.32 (s, CO$_2$CH$_2$, 4H); 3.90-3.75 (m, SiOCH$_2$, 12H); 2.80-2.70 (m, SCH$_2$, 4H); 1.70-1.60 (m, SCH$_2$CH$_2$, 4H); 1.52 (s, CH$_3$, 12H); 1.30-1.15 (m, SiOCH$_2$CH$_3$, 18H); 0.80-0.65 (m, SiCH$_2$, 4H). $^{13}$C-NMR (100 MHz, CDCl$_3$): 173.9 (s); 62.6 (t); 58.3 (t); 46.6 (s); 32.8 (t); 25.7 (q); 23.0 (t); 18.2 (q); 10.2 (t).

EXAMPLE 10

Preparation of Compound 179

To toluene (100 ml) is added at 10° C. and under a weak stream of nitrogen triethylamine (6.30 g, 61.9 mmol), then 1-bromoisobutyrylbromide (12.2 g, 51.6 mmol) followed by the dropwise addition of 3-mercaptopropyltriethoxysilane (12.9 g, 51.6 mmol). The reaction mixture is stirred for 1 hour at room temperature and then water (100 ml) is added. The aqueous phase is separated and the organic phase is washed with NaCl (2×80 ml), dried over sodium sulfate, filtered and evaporated to dryness using a rotary evaporator to afford 20.0 g (GC -purity: 99.2%) of the compound S-propyltriethoxysilane-2-bromo-2-methyl-thiopropionate of formula B, clear yellow liquid.

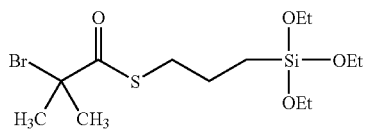

(B)

$^1$H-NMR (400 MHz, CDCl$_3$): δ=3.83 (q, J=7.2 Hz, SiOCH$_2$, 6H); 2.95 (t, J=7.2 Hz, SCH$_2$, 2H); 1.97 (s, CH$_3$, 6H); 1.80-1.65 (m, SCH$_2$CH$_2$, 2H); 1.30-1.20 (m, SiOCH$_2$CH$_3$, 9H); 0.80-0.70 (m, SiCH$_2$, 2H).

A mixture of S-propyltriethoxysilane-2-bromo-2-methyl-thiopropionate of formula B (10.0 g, 25.8 mmol), 3-mercaptopropyltriethoxysilane (6.50 g, 25.8 mmol) and solid potassium carbonate (7.13 g, 51.6 mmol) in methyl ethyl ketone (100 ml) is heated under reflux and under nitrogen for 24 hours. Water is then added and the product is extracted in ethyl acetate. The organic phase is washed with H$_2$O, NaCl, dried over sodium sulfate, filtered and evaporated to dryness using a rotary evaporator to afford 11.6 g (GC-purity: 86.7%) of a crude product as a yellow turbid liquid. The crude product is purified by distilling off the residual volatiles (oil bath temp. 225° C.; 0.05-0.1 mbar) to afford 10.4 g of compound 179 as yellow liquid. $^1$H-NMR (400 MHz, CDCl$_3$): δ=3.90-3.75 (m, SiOCH$_2$, 12H); 2.87 (t, J=7.2 Hz, SCH$_2$, 2H); 2.56 (t, J=7.2 Hz, SCH$_2$, 2H); 1.70-1.60 (m, SCH$_2$CH$_2$, 4H); 1.53 (s, CH$_3$, 6H); 1.35-1.15 (m, SiOCH$_2$CH$_3$, 18H); 0.70-0.55 (m, SiCH$_2$, 4H). $^{13}$C-NMR (100 MHz, CDCl$_3$): 203.0 (s); 58.4 (t); 55.1 (s); 33.1 (t); 32.5 (t); 26.3 (q); 23.1 (t); 22.8 (t); 18.3 (q); 10.2 (t); 10.1 (t).

EXAMPLE 11

Preparation of Compound 180

To a solution of hydrogen peroxide-urea complex (10.6 g) in ethanol (190 ml) is added at 30° C. under a weak stream of nitrogen 2-propyltriethoxysilanesulfanyl-butane (30 g, 102 mmol). The reaction mixture is stirred at room temperature for 21 hours. The solvent is evaporated using a rotary evaporator and the residue is dissolved in dichloromethane (100 ml). The precipitate was filtered off. The filtrate is diluted with dichloromethane (50 ml) and the solid formed filtered off. The filtrate is evaporated to dryness using a rotary evaporator to afford 29.9 g of compound 180 as a clear colourless liquid.

EXAMPLE 12

Preparation of Compound 181

To toluene (70 ml) is added at 0-5° C. and under a weak stream of nitrogen potassium tert-butanolate (0.07 g, 0.62 mmol), then dibutylmaleate (30.4 g, 129 mmol) followed by the dropwise addition of 3-mercaptopropyltriethoxysilane (32.4 g, 129 mmol). The reaction mixture is stirred for 30 minutes at room temperature and then water (50 ml) is added. The aqueous phase is separated and the organic phase is washed with NaCl (2×30 ml), dried over sodium sulfate, filtered and evaporated to dryness using a rotary evaporator to afford 60.5 g of compound 181 as yellow liquid.

EXAMPLE 13

Preparation of Compound 182

To toluene (1.5 l) is added at 10° C. and under a weak stream of nitrogen solid sodium ethanolate (48.7 g, 0.68 mol), followed by addition of 3-mercaptopropyltriethoxysilane (170.7 g, 0.72 mol) within 20 minutes. The reaction mixture is stirred for 15 minutes at 15° C., then octyl 2-bromoisobutyrate (200 g, 0.72 mol) is added dropwise over 1 hour at 15° C. After 30 minutes of stirring at room temperature, water (500 ml) is added to the reaction mass. The aqueous phase is separated and the organic phase is washed with NaCl (2×350 ml), dried over sodium sulfate, filtered and evaporated to dryness using a rotary evaporator to afford a crude product as a turbid yellow liquid. The crude product is purified by distillation (oil bath temp. 200° C.; overhead temperature 145-155° C.; 0.01-0.1 mbar) to afford 191 g (64%) of compound 182 as a clear colorless liquid. $^1$H-NMR (400 MHz, CDCl$_3$): δ=4.09 (t, J=6.8 Hz, CO$_2$CH$_2$, 2H); 3.81 (q, J=6.8 Hz, SiOCH$_2$, 6H); 2.61 (t, J=7.2 Hz, SCH$_2$, 2H); 1.70-1.55 (m, SCH$_2$CH$_2$+CO$_2$CH$_2$CH$_2$, 4H); 1.49 (s, CH$_3$, 6H), 1.40-1.15 (m, CH$_2$+SiOCH$_2$CH$_3$, 23H); 0.95-0.80 (m, CH$_3$, 3H); 0.75-0.65 (m, SiCH$_2$, 2H).

EXAMPLE 14

Preparation of Compound 183

To a suspension of 100 mg (0.87 mmol) of potassium tert-butanolate in 60 ml of dry toluene is added dropwise under nitrogen at 0° C. 21.7 g (86.7 mmol) of 3-mercaptopropyltriethoxysilane, followed by the dropwise addition of 29.5 g (86.7 mmol) of bis(2-ethylhexyl)maleate. The reaction mixture is stirred for one hour at room temperature. Water was then added and the product is extracted by ethyl acetate. The organic phase is washed with H$_2$O, NaCl, dried over sodium sulfate, filtered and evaporated to dryness using a rotary evaporator to afford 54.0 g of compound 183 as yellow liquid.

EXAMPLE 15

Preparation of Compound 184

A mixture of 2-bromo-N-[2-(2-bromo-propionylamino)-ethyl]-propionamide (5.00 g, 15.2 mmol), 3-mercaptopropyltriethoxysilane (7.60 g, 30.4 mmol) and solid potassium carbonate (8.40 g, 60.8 mmol) in methyl ethyl ketone (40 ml) is heated under reflux and under nitrogen for 24 hours. Water is then added and the product is extracted in ethyl acetate. The organic phase is washed with 1N NH$_4$Cl, NaCl, dried over sodium sulfate, filtered and evaporated to dryness using a rotary evaporator to afford a crude product as a colourless viscous liquid. The crude product is purified by flash chromatography (hexane/ethyl acetate: 1:1) to afford 3.40 g (GC-purity: 100%) of compound 184 as white waxy solid. $^1$H-NMR (400 MHz, CDCl$_3$): δ=7.16 (br s, NH, 2H); 3.83 (q, J=7.2 Hz, SiOCH$_2$, 12H); 3.50-3.40 (m, CONHCH$_2$, 4H); 3.38 (q, J=7.2 Hz, SCHCH$_3$, 2H); 2.57 (t, J=7.2 Hz, SCH$_2$, 4H); 1.80-1.65 (m, SCH$_2$CH$_2$, 4H); 1.47 (d, J=7.2 Hz, SCHCH$_3$, 6H); 1.24 (t, J=7.2 Hz, SiOCH$_2$CH$_3$, 18H); 0.80-

0.65 (m, SiCH$_2$, 4H). $^{13}$C-NMR (100 MHz, CDCl$_3$): 173.7 (s); 58.3 (t); 44.2 (d); 39.8 (t); 34.6 (t); 23.0 (t); 18.6 (q); 18.2 (q); 9.9 (t).

EXAMPLE 16

Preparation of Compound 185

A mixture of 2-bromo-N-[2-(2-bromo-2-methyl-propionylamino)-ethyl]-2-methyl-propionamide (15.0 g, 41.9 mmol), 3-mercaptopropyltriethoxysilane (21.0 g, 83.5 mmol) and solid potassium carbonate (23.1 g, 167 mmol) in methyl ethyl ketone (100 ml) is heated under reflux and under nitrogen for 48 hours. Water is then added and the product is extracted by ethyl acetate. The organic phase is washed with 1N NH$_4$Cl, NaCl, dried over sodium sulfate, filtered and evaporated to dryness using a rotary evaporator to afford a crude product as a pale yellow clear liquid. The crude product is purified by flash chromatography (hexane/ethyl acetate: 2:1) to afford 8.50 g of compound 185 as clear colourless liquid. $^1$H-NMR (400 MHz, CDCl$_3$): δ=7.35 (br s, NH, 2H); 3.80 (q, J=7.2 Hz, SiOCH$_2$, 12H); 3.45-3.35 (m, CO$_2$NHCH$_2$, 4H); 2.52 (t, J=7.2 Hz, SCH$_2$, 4H); 1.70-1.60 (m, SCH$_2$CH$_2$, 4H); 1.49 (s, CH$_3$, 12H); 1.21 (t, J=7.2 Hz, SiOCH$_2$CH$_3$, 18H); 0.75-0.65 (m, SiCH$_2$, 4H). $^{13}$C-NMR (100 MHz, CDCl$_3$): 175.7 (s); 58.4 (t); 49.4 (s); 40.1 (t); 33.0 (t); 26.9 (q); 23.1 (t); 18.3 (q); 10.3 (t).

EXAMPLE 17

Preparation of Compound 186

A mixture of tert-butyl 2-bromoisobutyrate (23.7 g, 105 mmol), 3-mercaptopropyltriethoxysilane (26.4 g, 105 mmol) and solid potassium carbonate (29.0 g, 210 mmol) in methyl ethyl ketone (105 ml) is heated under reflux and under nitrogen for 24 hours. Water is then added and the product is extracted with toluene. The organic phase is washed with 1M NH$_4$Cl, NaCl, dried over sodium sulfate, filtered and evaporated to dryness using a rotary evaporator to afford a crude product as a turbid pale yellow liquid. The crude product is purified by distillation (oil bath temperature 180° C.; overhead temperature 120-125° C.; vacuum: 0.05-0.1 mbar) to afford 42.5 g (60%) of compound 186 as a clear colorless liquid. $^1$H-NMR (300 MHz, CDCl$_3$): δ=3.81 (q, J=7.2 Hz, SiOCH$_2$, 6H); 2.64 (t, J=7.5 Hz, SCH$_2$, 2H); 1.75-1.60 (m, SCH$_2$CH$_2$, 2H); 1.47 (s, CH$_3$, 9H), 1.45 (s, CH$_3$, 6H), 1.28-1.15 (m, SiOCH$_2$CH$_3$, 9H); 0.80-0.65 (m, SiCH$_2$, 2H). $^{13}$C-NMR (75 MHz, CDCl$_3$): 173.3 (s); 80.6 (s); 58.3 (t); 47.4 (s); 32.6 (t); 27.8 (q); 25.8 (q); 23.1 (t); 18.2 (q); 10.3 (t).

EXAMPLE 18

Preparation of Compound 187

To toluene (200 ml) is added at room temperature and under a weak stream of nitrogen triethylamine (0.61 g, 6 mmol), then maleic anhydride (11.80 g, 119 mmol) followed by the dropwise addition of 3-mercaptopropyltriethoxysilane (32.4 g, 129 mmol). The reaction mixture is stirred for 12 hours at room temperature and then water (50 ml) is added. The aqueous phase is separated and the organic phase is washed with H$_2$O (3×60 ml), brine (4×50 ml), dried over sodium sulfate, filtered and evaporated to dryness using a rotary evaporator to afford 26.0 g of compound 187 as brown liquid.

EXAMPLE 19

Preparation of Compound 188

A mixture of [2-(2-bromo-propionyloxy)-ethyl]-2-bromopropionate (12.0 g, 36.1 mmol), 3-mercaptopropyltriethoxysilane (17.2 g, 72.2 mmol) and solid potassium carbonate (20.0 g, 144 mmol) in methyl ethyl ketone (100 ml) is heated under reflux and under nitrogen for 18 hours. Water Is then added and the product Is extracted with ethyl acetate. The organic phase is washed with 1N NH$_4$Cl, NaCl, dried over sodium sulfate, filtered and evaporated to dryness using a rotary evaporator to afford a crude product as a clear yellow liquid. The crude product is purified by flash chromatography (hexane/ethyl acetate: 4:1) to afford 16.3 g (GC -purity: 91.0%) of compound 188 as clear colourless liquid. $^1$H-NMR (400 MHz, CDCl$_3$): δ=4.50-4.30 (m, CO$_2$CH$_2$, 4H); 4.00-3.75 (m, SiOCH$_2$, 12H); 3.50-3.35 (m, SCHCH$_3$, 2H); 2.85-2.55 (m, SCH$_2$, 4H); 1.80-1.60 (m, SCH$_2$CH$_2$, 4H); 1.60-1.40 (m, CH$_3$, 6H); 1.40-1.15 (m, SiOCH$_2$CH$_3$, 18H); 0.85-0.65 (m, SiCH$_2$, 4H).

EXAMPLE 20

Preparation of Compound 222

A mixture of dodecyl 2-bromoisobutyrate (54.3 g, 162 mmol), 3-mercaptopropyltriethoxysilane (42.7 g, 170 mmol) and solid potassium carbonate (44.9 g, 325 mmol) in methyl ethyl ketone (200 ml) Is heated under reflux and under nitrogen for 24 hours. Water Is then added and the product Is extracted in ethyl acetate. The organic phase Is washed with H2O, NaCl, dried over sodium sulfate, filtered and evaporated to dryness using a rotary evaporator to afford a crude product as a yellow liquid. The crude product Is purified by distilling off the residual volatiles (oil bath temperature 200° C.; 0.05-0.1 mbar) to afford 42.6 g of a yellow liquid residue containing 90% (GC-purity) of compound 222. $^1$H-NMR (400 MHz, CDCl$_3$): δ=4.11 (t, J=6.8 Hz, CO$_2$CH$_2$, 2H); 3.82 (q, J=6.8 Hz, SiOCH$_2$, 6H); 2.64 (t, J=7.2 Hz, SCH$_2$, 2H); 1.80-1.60 (m, SCH$_2$CH$_2$+CO$_2$CH$_2$CH$_2$, 4H); 1.52 (s, CH$_3$, 6H), 1.50-1.15 (m, CH$_2$+SiOCH$_2$CH$_3$, 27H); 0.90 (t, J=6.8 Hz, CH$_3$, 3H); 0.80-0.65 (m, SiCH$_2$, 2H).

EXAMPLE 21

Preparation of Compound 190

To a suspension of 20 mg (0.17 mmol) of potassium tert-butanolate in 40 ml of dry toluene is added dropwise under nitrogen at 0° C. 4.13 g (17.3 mmol) of 3-mercapto-propyl-triethoxysilane, followed by the dropwise addition of 5.89 g (17.3 mmol) of dioctyl maleate. The reaction mixture is stirred for one hour at room temperature. Water is then added and the product is extracted with ethyl acetate. The organic phase is washed with H$_2$O, NaCl, dried over sodium sulfate, filtered and evaporated to dryness using a rotary evaporator to afford 9.80 g of compound 190 as colourless liquid. $^1$H-NMR (300 MHz, CDCl$_3$): δ=4.20-4.00 (m, CO$_2$CH$_2$, 4H); 3.90-3.75 (m, SiOCH$_2$, 6H); 3.70-3.60 (m, SCHCO$_2$, 1H); 3.10-2.95 (m, SCHCH$_2$CO$_2$, 1H); 2.70-2.60 (m, SCHCH$_2$CO$_2$+SCH$_2$, 3H); 1.80-1.55 (m, SCH$_2$CH$_2$+CO$_2$CH$_2$CH$_2$, 6H); 1.55-1.15 (m, SiOCH$_2$CH$_3$+CH$_2$, 29H); 1.00-0.80 (m, CH$_3$, 6H); 0.80-0.65 (m, SiCH$_2$, 2H).

EXAMPLE 22

Preparation of Compound 191

A mixture of octadecyl 2-bromoisobutyrate (28.1 g, 67.0 mmol), 3-mercaptopropyltriethoxysilane (16.8 g, 67.0 mmol) and solid potassium carbonate (18.5 g, 134 mmol) in methyl ethyl ketone (100 ml) is heated under reflux and under nitrogen for 24 hours. Water is then added and the product is extracted in ethyl acetate. The organic phase is washed with $H_2O$, NaCl, dried over sodium sulfate, filtered and evaporated to dryness using a rotary evaporator to afford a crude product as a yellow liquid. The crude product is purified by distilling off the residual volatiles (oil bath temperature 225° C.; 0.05-0.1 mbar) to afford 34.7 g of a yellow liquid residue containing 89% (GC-purity) of compound 191. $^1$H-NMR (400 MHz, $CDCl_3$): δ=4.11 (t, J=6.8 Hz, $CO_2CH_2$, 2H); 3.82 (q, J=7.2 Hz, $SiOCH_2$, 6H); 2.63 (t, J=7.2 Hz, $SCH_2$, 2H); 1.70-1.60 (m, $SCH_2CH_2+CO_2CH_2CH_2$, 4H); 1.51 (s, $CH_3$, 6H), 1.40-1.15 (m, $CH_2$, 30H); 1.23 (t, J=7.2 Hz, $SiOCH_2CH_3$, 9H); 0.89 (t, J=7.2 Hz, $CH_3$, 3H); 0.75-0.65 (m, $SiCH_2$, 2H).

Application Results

The characteristics of the rubber compounds and vulcanizates are compared to the ones prepared with bis(3-triethoxysilylpropyl)disulfide (TESPD; or Si 75 from Degussa) and 3-octanoylthio-1-propyltriethoxysilane (NXT Silane from Crompton OSi Specialities). In terms of processability, as illustrated by the low values of Mooney viscosity, the new rubber compositions of the instant invention are superior to the ones obtained with TESPD or NXT Silane. In contrary to the polysulfide silanes (TESPT and TESPD), which are sensitive to heat and cause premature vulcanisation during mixing, the treatment of silica with the coupling agents of the formula I in a one-step process do not show any sign of undesirable pre-coupling with the rubber molecules, allowing to maintain the viscosity of the rubber compound favourably very low.

Processing safety advantages are obtained in a one-step mixing procedure which means that a simplified process can be used safely instead of the typically preparatory thermo-chemical mixing multi-steps, referred to as non-productive mixing steps, to blend the rubber and various rubber compounding ingredients prior the addition of the curing system. The enlarged processing windows obtained with the coupling agents of the formula I give as end result the possibility to make a significant improvement in the cost of silica tires in applying a one-step mixing process that helps shorten processing time.

EXAMPLE 23

Preparation of Silica Filled Rubber Compounds and Vulcanization

Employing the ingredients indicated below, which are listed in parts per hundred of rubber per weight, the rubber compositions are compounded in the following manner:

A basic compound containing 103.1 parts of oil extended SSBR [Buna VSL 5025-1], 25 parts of BR [Buna CB 24], 2.5 parts of ZnO, 1.0 part of stearic acid, 80 parts of silica [Ultrasil 7000 GR from Degussa], 5 parts of a plasticizer (Isoftener 450), 2 parts of an antidegradant 6PPD (Vulkanox 4020), 1.5 part of a wax (Antilux 500) and x parts of the coupling agent of the formula I are charged to a laboratory mixer [Werner and Pfleiderer GK 1,5 E] at 115° C. for 15 minutes at a rotor speed of 75 rpm and a fill ractor of 0.72. The temperature of the basic compounds is 190-200° C. The torque (Nm) required to operate the rotors during mixing as well as the stock temperature are recorded continuously. The lower the Maximum Torque at 15 min. mixing time the better.

The curing system is subsequently added on the two roll mill at 60° C. The physical properties of the vulcanizates are then measured. The results are summarized in Table 1. The abrasion resistance is measured according to DIN 53516. Excellent tear growth resistance, measured at room temperature is obtained.

The Rheometer curves are measured at 160° C. with an Oscillating Disc Rheometer (ODR).

From these rubber compounds the Mooney Viscosity is measured according to ASTM Method D 1646. The value is obtained for a rubber tested in a Mooney viscometer. In the viscometer, the material is subjected to shearing forces, and the greater the resistance of the material to shear, the higher the Mooney viscosity value. The viscosity value is obtained by using either a large rotor (L) or a small rotor (S). ML (1+4) (100° C.) indicates a Mooney viscosity number obtained by using a large rotor after 1 min of pre-heating followed by 4 min of heating at 100° C.

The machine is also used to determine the scorch characteristics of rubber mixes according to ASTM Method D 1646. The results are summarized in Table 1. The lower the Mooney Viscosity values the better.

TABLE 1

| Example | Coupling agent | Mooney Viscosity | Tear growth resistance (N/mm) | Abrasion ($mm^3$) | Tan delta (−25° C.) |
|---|---|---|---|---|---|
| 23a[a)] | 5.5 phr Si 75[c)] | 96 | 3.3 | 91 | 0.65 |
| 23b[a)] | 9.7 phr NXT Silane[d)] | 102 | 9.4 | 86 | 0.78 |
| 23c[b)] | 9.5 phr compound 122 | 87 | 16.7 | 92 | 0.65 |
| 23d[b)] | 11.0 phr compound 111 | 83 | 19.4 | 103 | 0.65 |

Explanation of footnotes a)-d) see end of Table 3.

EXAMPLE 24

Preparation of Silica Filled Rubber Compounds and Vulcanization

Employing the ingredients indicated below, which are listed in parts per hundred of rubber per weight, the rubber compositions are compounded in the following manner:

A basic compound containing 75 parts of SSBR [Buna VSI 5025-0, 25 parts of BR [Buna CB 527T], 2.5 parts of ZnO, 1.0 part of stearic acid, 80 parts of silica [Ultrasil VN3 from Degussa], 31 parts of a plasticizer (Ingralen 450), 2 parts of an antidegradant 6PPD (Vulkanox 4020), 1.5 part of a wax (Antilux 500) and x parts of the coupling agent is charged to a laboratory mixer [MixerX Haake Rheomix3010p] at 125° C. for 20 min at a rotor speed of 75 rpm. The temperature of the basic compounds was 167-178° C. The torque (Nm) required to operate the rotors during mixing as well as the stock temperature is recorded continuously. The lower the Maximum Torque at 15 min. mixing time the better.

From these rubber compounds the Mooney Viscosity is measured according to ASTM Method D 1646. The value is obtained for a rubber tested in a Mooney viscometer. In the viscometer, the material is subjected to shearing forces, and the greater the resistance of the material to shear, the higher the Mooney viscosity value. The viscosity value is obtained by using either a large rotor (L) or a small rotor (S). ML (1+4) (100° C.) indicates a Mooney viscosity number obtained by using a large rotor after 1 min of pre-heating followed by 4 min of heating at 100° C. The lower the Mooney Viscosity values the better. The results are summarized in Table 2.

TABLE 2

| Example | Coupling agent | Mooney Viscosity | Maximum Torque at 20 min. mixing time |
|---|---|---|---|
| 24a[a)] | 9.70 phr NXT Silane[d)] | 53 | 102 |
| 24b[b)] | 9.50 phr compound 162 | 34 | 77 |
| 24c[b)] | 10.2 phr compound 163 | 37 | 93 |
| 24d[b)] | 11.0 phr compound 164 | 29 | 72 |
| 24e[b)] | 11.0 phr Example 4 | 35 | 89 |
| 24f[b)] | 11.0 phr Example 5 | 33 | 84 |
| 24g[b)] | 10.2 phr Example 6 | 34 | 81 |
| 24h[b)] | 8.90 phr compound 176 | 46 | 95 |

Explation of footnotes a)-d) see end of Table 3.

The Rheometer curves are measured at 160° C. with an Oscillating Disc Rheometer (ODR).

The $Ts_2$ values of the Rheometer curve (ASTM Method D 2084) indicate the scorch resistance of a rubber compound. MH is the maximum torque. Scorch safety ($Ts_2$) is the time to 2 units above minimum torque and cure time (T95) is the time to 95% of delta torque above minimum. The compounds of the formula I fulfil the high criteria as coupling agents with good scorch resistance for silica filled styrene-butadiene rubber compounds. The results are summarized in Table 3.

TABLE 3

| Example | Coupling agent | MH (dNm) | $Ts_2$ (min) | T95 (min) |
|---|---|---|---|---|
| 24a[a)] | 9.70 phr NXT Silane[d)] | 12.6 | 1.2 | 5.8 |
| 24b[b)] | 9.50 phr compound 162 | 16.5 | 6.7 | 21.7 |
| 24c[b)] | 10.2 phr compound 163 | 16.2 | 7.8 | 23.0 |
| 24d[b)] | 11.0 phr compound 164 | 15.7 | 6.6 | 20.9 |
| 24e[b)] | 11.0 phr Example 4 | 14.0 | 8.2 | 23.9 |
| 24f[b)] | 11.0 phr Example 5 | 14.0 | 8.5 | 23.5 |
| 24g[b)] | 10.2 phr Example 6 | 14.1 | 7.2 | 22.7 |
| 24h[b)] | 8.90 phr compound 176 | 14.9 | 4.6 | 17.1 |

[a)]Comparison Example.
[b)]Example according to the invention.
c) Si 75 (RTM) is bis(3-triethoxysilylpropyl)disulfide or TESPD from Degussa
[d)]NXT Silane (RTM) is 3-octanoylthio-1-propyltriethoxysilane from Crompton OSi Specialities.

What is claimed is:

1. A process for the manufacture of a filled rubber compound with improved processability which comprises mixing in one-step a) a rubber, b) a white reinforcing filler and c) a coupling agent of the formula I

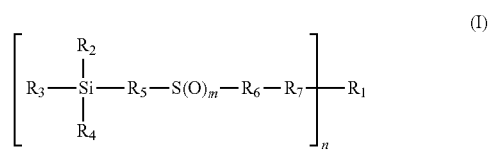

wherein, when n is 1, $R_1$ is hydrogen, $C_1$-$C_{25}$alkyl, $C_1$-$C_{25}$alkyl substituted with furyl, morpholine, $C_1$-$C_4$dialkylamino, $C_1$-$C_4$trialkylammonium or $M^+$ $^-O_3S$—; $C_2$-$C_{25}$alkyl interrupted by oxygen; $C_5$-$C_{12}$cycloalkyl, $C_2$-$C_{25}$alkenyl, unsubstituted or $C_1$-$C_4$alkyl-substituted phenyl; $C_7$-$C_{12}$phenoxyalkyl, unsubstituted or $C_1$-$C_4$alkyl substituted $C_7$-$C_9$bicycloalkyl;

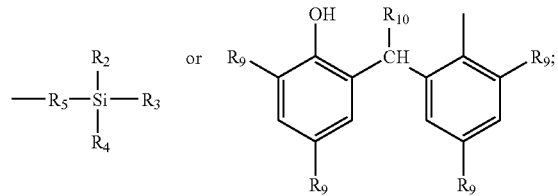

or when $R_7$ is a direct bond, $R_1$ is —CN, —$SOR_8$, —$SO_2R_8$, —$NO_2$ or —$COR_8$;

when n is 2, $R_1$ is $C_1$-$C_{25}$alkylene, $C_1$-$C_{25}$alkylene substituted with $C_1$-$C_4$alkyl; $C_2$-$C_{25}$alkylene substituted with $C_1$-$C_4$alkyl and interrupted by oxygen; $C_2$-$C_{25}$alkylene interrupted by oxygen, sulfur, phenylene or cyclohexylene;

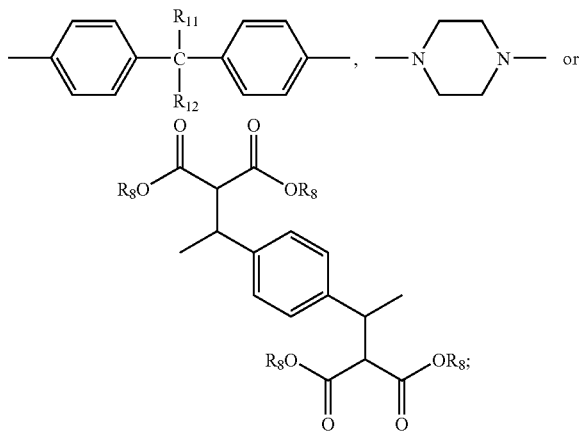

or when $R_6$ and $R_7$ are a direct bond, $R_1$ is

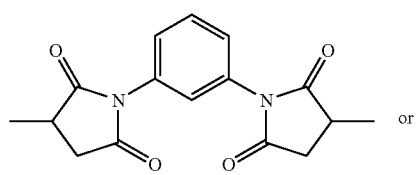

-continued

[structure: 1,3-phenylene-bis(methylene) linked to two 3-methyl-pyrrolidine-2,5-dione groups with CH3 substituents]

$R_2$, $R_3$ and $R_4$ are each independently of the others $C_1$-$C_{25}$alkyl, $C_2$-$C_{25}$alkyl interrupted by oxygen; $C_5$-$C_{12}$cycloalkyl, $C_2$-$C_{25}$alkenyl, unsubstituted or $C_1$-$C_4$alkyl-substituted phenyl, $C_7$-$C_9$phenylalkyl, $C_1$-$C_{25}$alkoxy, $C_3$-$C_{25}$alkoxy interrupted by oxygen; $C_5$-$C_{12}$cycloalkoxy, $C_2$-$C_{25}$alkenyloxy, unsubstituted or $C_1$-$C_4$alkyl-substituted phenoxy, $C_7$-$C_9$phenylalkoxy, halogen, $C_2$-$C_{25}$alkanoyloxy or unsubstituted or $C_1$-$C_4$alkyl substituted benzoyloxy; or at least two of $R_2$, $R_3$ and $R_4$ are —O—$R_{15}$—O—; or $R_2$ is additionally $$-\text{O}-R_{16}\left[-\text{O}-\underset{\underset{R_4}{|}}{\overset{\overset{R_3}{|}}{\text{Si}}}-R_5-\text{S(O)}_m-R_6-R_7\right]_n-R_1;$$

or $R_3$ is additionally $$-\text{O}-R_{16}\left[-\text{O}-\underset{\underset{R_4}{|}}{\overset{\overset{R_2}{|}}{\text{Si}}}-R_5-\text{S(O)}_m-R_6-R_7\right]_n-R_1;$$

or $R_4$ is additionally $$-\text{O}-R_{16}\left[-\text{O}-\underset{\underset{R_3}{|}}{\overset{\overset{R_2}{|}}{\text{Si}}}-R_5-\text{S(O)}_m-R_6-R_7\right]_n-R_1;$$

with the proviso that at least one of $R_2$, $R_3$ or $R_4$ is $C_1$-$C_{25}$alkoxy, $C_3$-$C_{25}$alkoxy interrupted by oxygen; $C_5$-$C_{12}$cycloalkoxy, $C_2$-$C_{25}$alkenyloxy, unsubstituted or $C_1$-$C_4$alkyl-substituted phenoxy, $C_7$-$C_9$phenylalkoxy, halogen, $C_2$-$C_{25}$alkanoyloxy or unsubstituted or $C_1$-$C_4$alkyl substituted benzoyloxy;

$R_5$ is $C_1$-$C_{25}$alkylene, $C_5$-$C_{12}$cycloalkylene, unsubstituted or $C_1$-$C_4$alkyl substituted phenylene;

$R_6$ is a direct bond, $C_1$-$C_{25}$alkylene; or $C_1$-$C_{25}$alkylene substituted with $C_1$-$C_{25}$alkyl, $C_2$-$C_{25}$alkoxycarbonyl, $C_3$-$C_{25}$alkoxycarbonylalkyl or phenyl;

$R_7$ is a direct bond or $$-\overset{\overset{\text{O}}{\|}}{\text{C}}-R_{13}-,$$

with the proviso that, when $R_7$ is a direct bond and n is 1, $R_6$ is not a direct bond; and with the proviso that, when $R_7$ is $$-\overset{\overset{\text{O}}{\|}}{\text{C}}-R_{13}-,$$

$R_6$ is not a direct bond;

$R_8$ is $C_1$-$C_{25}$alkyl, $C_2$-$C_{25}$alkyl interrupted by oxygen; $C_5$-$C_{12}$cycloalkyl, $C_2$-$C_{25}$alkenyl, $C_2$-$C_{25}$alkinyl, $C_7$-$C_9$phenylalkyl, unsubstituted or $C_1$-$C_4$alkyl-substituted phenyl, $R_9$ is $C_1$-$C_5$alkyl, $R_{10}$ is hydrogen or $C_1$-$C_4$alkyl, $R_{11}$ and $R_{12}$ are each independently of the other hydrogen, $CF_3$, $C_1$-$C_{12}$alkyl or phenyl, or $R_{11}$ and $R_{12}$, together with the carbon atom to which they are bonded, form a $C_5$-$C_8$cycloalkylidene ring that is unsubstituted or substituted by from 1 to 3 $C_1$-$C_4$alkyl groups, $R_{13}$ is oxygen or —N($R_{14}$)—, $R_{14}$ is hydrogen or $C_1$-$C_{12}$alkyl, $R_{15}$ is $C_1$-$C_{25}$alkylene or $C_1$-$C_{25}$alkylene substituted with $C_1$-$C_{25}$alkyl;

$R_{16}$ is $C_1$-$C_{25}$alkylene or $C_1$-$C_{25}$alkylene substituted with $C_1$-$C_{25}$alkyl;

M is sodium, potassium or ammonium, m is 0, 1 or 2 and n is 1 or 2; or an oligomeric hydrolysis product of the compound of the formula I.

2. A process according to claim 1, wherein, when n is 1, $R_1$ is hydrogen, $C_1$-$C_{25}$alkyl, $C_1$-$C_{25}$alkyl substituted with furyl, morpholine, $C_1$-$C_4$dialkylamino, $C_1$-$C_4$trialkylammonium or $M^+$ $^-O_3S$—; $C_2$-$C_{25}$alkyl interrupted by oxygen; $C_5$-$C_{12}$cycloalkyl, $C_2$-$C_{25}$alkenyl, unsubstituted or $C_1$-$C_4$alkyl-substituted phenyl; $C_7$-$C_{12}$phenoxyalkyl, unsubstituted or $C_1$-$C_4$alkyl substituted $C_7$-$C_9$bicycloalkyl;

[structures: silyl group with $R_2$, $R_3$, $R_4$, $R_5$; and bisphenol-type structure with OH, $R_{10}$, $R_9$ substituents]

or when $R_7$ is a direct bond, $R_1$ is —CN, —$SOR_8$, —$SO_2R_8$, —$NO_2$ or —$COR_8$, when n is 2, $R_1$ is $C_1$-$C_{25}$alkylene, $C_1$-$C_{25}$alkylene substituted with $C_1$-$C_4$alkyl; $C_2$-$C_{25}$alkylene substituted with $C_1$-$C_4$alkyl and interrupted by oxygen; $C_2$-$C_{25}$alkylene interrupted by oxygen, sulfur, phenylene or cyclohexylene;

[structures: bis-phenyl methane with $R_{11}$, $R_{12}$ substituents; and piperazine ring] or -continued

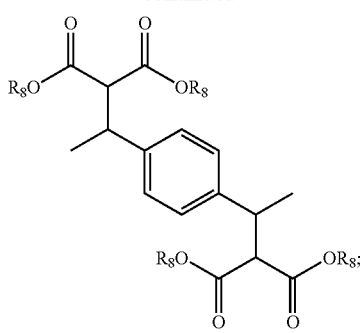

or when R$_6$ and R$_7$ are a direct bond, R$_1$ is

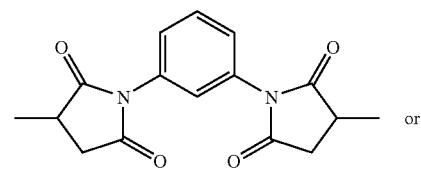

R$_2$, R$_3$ and R$_4$ are each independently of the others C$_1$-C$_{25}$alkyl, C$_2$-C$_{25}$alkyl interrupted by oxygen; C$_5$-C$_{12}$cycloalkyl, C$_2$-C$_{25}$alkenyl, unsubstituted or C$_1$-C$_4$alkyl-substituted phenyl, C$_7$-C$_9$phenylalkyl, C$_1$-C$_{25}$alkoxy, C$_3$-C$_{25}$alkoxy interrupted by oxygen; C$_5$-C$_{12}$cycloalkoxy, C$_2$-C$_{25}$alkenyloxy, unsubstituted or C$_1$-C$_4$alkyl-substituted phenoxy, C$_7$-C$_9$phenylalkoxy, halogen, C$_2$-C$_{25}$alkanoyloxy or unsubstituted or C$_1$-C$_4$alkyl substituted benzoyloxy; with the proviso that at least one of R$_2$, R$_3$ or R$_4$ is C$_1$-C$_{25}$alkoxy, C$_3$-C$_{25}$alkoxy interrupted by oxygen; C$_5$-C$_{12}$cycloalkoxy, C$_2$-C$_{25}$alkenyloxy, unsubstituted or C$_1$-C$_4$alkyl-substituted phenoxy, C$_7$-C$_9$phenylalkoxy, halogen, C$_2$-C$_{25}$alkanoyloxy or unsubstituted or C$_1$-C$_4$alkyl substituted benzoyloxy;

R$_5$ is C$_1$-C$_{25}$alkylene, C$_5$-C$_{12}$cycloalkylene, unsubstituted or C$_1$-C$_4$alkyl substituted phenylene;

R$_6$ is a direct bond, C$_1$-C$_{25}$alkylene; or C$_1$-C$_{25}$alkylene substituted with C$_1$-C$_{25}$alkyl, C$_2$-C$_{25}$alk-oxycarbonyl, C$_3$-C$_{25}$alkoxycarbonylalkyl or phenyl;

R$_7$ is a direct bond or

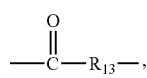

with the proviso that, when R$_7$ is a direct bond and n is 1, R$_6$ is not a direct bond; and with the proviso that, when R$_7$ is

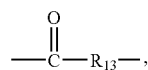

R$_6$ is not a direct bond;

R$_8$ is C$_1$-C$_{25}$alkyl, C$_2$-C$_{25}$alkyl interrupted by oxygen; C$_5$-C$_{12}$cycloalkyl, C$_2$-C$_{25}$alkenyl, C$_2$-C$_{25}$alkinyl, C$_7$-C$_9$phenylalkyl, unsubstituted or C$_1$-C$_4$alkyl-substituted phenyl, R$_9$ is C$_1$-C$_5$alkyl, R$_{10}$ is hydrogen or C$_1$-C$_4$alkyl, R$_{11}$ and R$_{12}$ are each independently of the other hydrogen, CF$_3$, C$_1$-C$_{12}$alkyl or phenyl, or R$_{11}$ and R$_{12}$, together with the carbon atom to which they are bonded, form a C$_5$-C$_8$cycloalkylidene ring that is unsubstituted or substituted by from 1 to 3 C$_1$-C$_4$alkyl groups, R$_{13}$ is oxygen or —(R$_{14}$)—, R$_{14}$ is hydrogen or C$_1$-C$_{12}$alkyl, M is sodium, potassium or ammonium, m is 1 or 2 and n is 1 or 2; or an oligomeric hydrolysis product of the compound of the formula I.

3. A process according to claim 1, wherein when n is 1,

R$_1$ is hydrogen, C$_1$-C$_{18}$alkyl, C$_1$-C$_{18}$alkyl substituted with furyl, morpholine, C$_1$-C$_4$dialkylamino, C$_1$-C$_4$trialkylammonium or M$^+$ $^{-O}$$_3$S—; C$_2$-C$_{18}$alkyl interrupted by oxygen; C$_5$-C$_8$cycloalkyl, C$_2$-C$_{18}$alkenyl, unsubstituted or C$_1$-C$_4$alkyl-substituted phenyl; C$_7$-C$_{10}$phenoxyalkyl, unsubstituted or C$_1$-C$_4$alkyl substituted C$_7$-C$_9$bicycloalkyl;

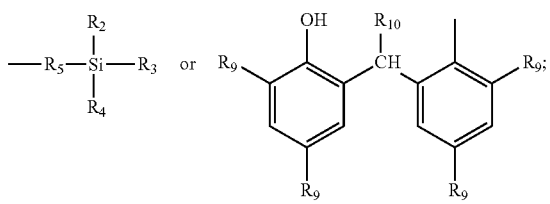

or when R$_7$ is a direct bond,

R$_1$ is —CN, —SOR$_8$, —SO$_2$R$_8$, —NO$_2$ or —COR$_8$, when n is 2,

R$_1$ is C$_1$-C$_{18}$alkylene, C$_1$-C$_{18}$alkylene substituted with C$_1$-C$_4$alkyl; C$_2$-C$_{18}$alkylene substituted with C$_1$-C$_4$alkyl and interrupted by oxygen; C$_2$-C$_{18}$alkylene interrupted by oxygen, sulfur, phenylene or cyclohexylene;

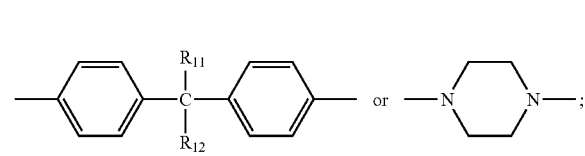

or when $R_6$ and $R_7$ are a direct bond, $R_1$ is

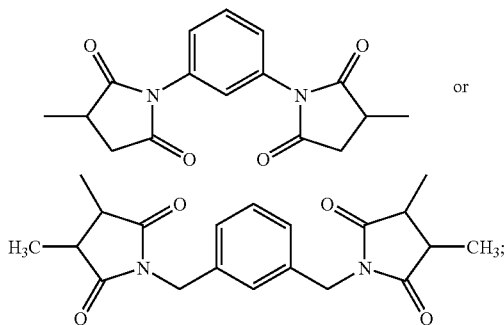

$R_2$, $R_3$ and $R_4$ are each independently of the others $C_1$-$C_{18}$alkyl, $C_2$-$C_{18}$alkyl interrupted by oxygen; $C_5$-$C_8$cycloalkyl, $C_2$-$C_{18}$alkenyl, unsubstituted or $C_1$-$C_4$alkyk-substituted phenyl, $C_7$-$C_9$phenylalkyl, $C_1$-$C_{18}$alkoxy, $C_3$-$C_{18}$alkoxy interrupted by oxygen; $C_5$-$C_8$cycloalkoxy, $C_2$-$C_{18}$alkenyloxy, unsubstituted or $C_1$-$C_4$alkyk-substituted phenoxy, $C_7$-$C_9$phenylalkoxy, halogen, $C_2$-$C_{18}$alkanoyloxy or unsubstituted or $C_1$-$C_4$alkyl substituted benzoyloxy; with the proviso that at least one of $R_2$, $R_3$ or $R_4$ is $C_1$-$C_{18}$alkoxy, $C_3$-$C_{18}$alkoxy interrupted by oxygen; $C_5$-$C_8$cycloalkoxy, $C_2$-$C_{18}$alkenyloxy, unsubstituted or $C_1$-$C_4$alkyl-substituted phenoxy, $C_7$-$C_9$phenylalkoxy, halogen, $C_2$-$C_{18}$alkanoyloxy or unsubstituted or $C_1$-$C_4$alkyl substituted benzoyloxy;

$R_5$ is $C_1$-$C_{18}$alkylene, $C_5$-$C_8$cycloalkylene, unsubstituted or $C_1$-$C_4$alkyl substituted phenylene;

$R_6$ is a direct bond, $C_1$-$C_{18}$alkylene; or $C_1$-$C_{18}$alkylene substituted with $C_1$-$C_{18}$alkyl, $C_2$-$C_{18}$al-koxycarbonyl, $C_3$-$C_{18}$alkoxycarbonylalkyl or phenyl;

$R_7$ is a direct bond or

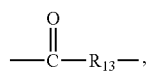

with the proviso that, when $R_7$ is a direct bond and n is 1, $R_6$ is not a direct bond; and with the proviso that, when $R_7$ is

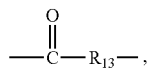

$R_6$ is not a direct bond;

$R_8$ is $C_1$-$C_{18}$alkyl, $C_2$-$C_{18}$alkyl interrupted by oxygen; $C_5$-$C_8$cycloalkyl, $C_2$-$C_{18}$alkenyl, $C_2$-$C_{18}$alkinyl, $C_7$-$C_9$phenylalkyl, unsubstituted or $C_1$-$C_4$alkyl-substituted phenyl, $R_9$ is $C_1$-$C_5$alkyl, $R_{10}$ is hydrogen or methyl, $R_{11}$ and $R_{12}$ are each independently of the other hydrogen, $CF_3$, $C_1$-$C_8$alkyl or phenyl, or $R_{11}$ and $R_{12}$, together with the carbon atom to which they are bonded, form a $C_5$-$C_8$cycloalkylidene ring that is unsubstituted or substituted by from 1 to 3 $C_1$-$C_4$alkyl groups, $R_{13}$ is oxygen or —N($R_{14}$)—, $R_{14}$ is hydrogen or $C_1$-$C_8$alkyl, M is sodium, potassium or ammonium, m is 1 or 2 and n is 1 or 2.

4. A process according to claim 1, wherein $R_2$, $R_3$ and $R_4$ are each independently of the others $C_1$-$C_4$alkyl or $C_1$-$C_4$alkoxy; with the proviso that at least one of $R_2$, $R_3$ or $R_4$ is $C_1$-$C_4$alkoxy.

5. A process according to claim 1, wherein $R_5$ is $C_2$-$C_4$alkylene.

6. A process according to claim 1, wherein when n is 1, $R_1$ is hydrogen, $C_1$-$C_{18}$alkyl, $C_1$-$C_{12}$alkyl substituted with furyl, morpholine, $C_1$-$C_4$dialkylamino, $C_1$-$C_4$trialkylammonium or $M^+$ $^-O_3S$—; $C_2$-$C_{12}$alkyl interrupted by oxygen; cyclohexyl, $C_4$-$C_{12}$-alkenyl, phenyl, $C_7$-$C_{10}$phenoxyalkyl, unsubstituted or $C_1$-$C_4$alkyl substituted $C_7$-$C_9$bicycloalkyl;

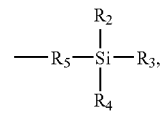

or when $R_7$ is a direct bond, $R_1$ is —CN, —$SOR_8$ or —$SO_2R_8$;

when n is 2, $R_1$ is $C_2$-$C_{12}$alkylene, $C_2$-$C_{12}$alkylene substituted with methyl; $C_2$-$C_{12}$alkylene substituted with methyl and interrupted by oxygen; $C_4$-$C_{12}$alkylene interrupted by oxygen, sulfur, phenylene or cyclohexylene;

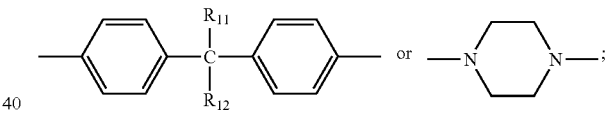

or when $R_6$ and $R_7$ are a direct bond, $R_1$ is

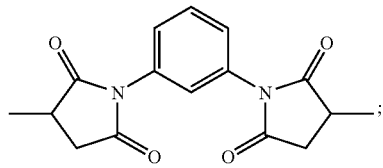

$R_2$, $R_3$ and $R_4$ are each independently of the others $C_1$-$C_8$alkyl, $C_4$-$C_8$alkyl interrupted by oxygen; cyclohexyl, $C_2$-$C_{12}$alkenyl, benzyl, $C_1$-$C_8$alkoxy, $C_3$-$C_8$alkoxy interrupted by oxygen; cyclohexyloxy, $C_2$-$C_{12}$alkenyloxy, phenoxy, benzyloxy, chloro, bromo, $C_2$-$C_8$alkanoyloxy or benzoyloxy; with the proviso that at least one of $R_2$, $R_3$ or $R_4$ is $C_1$-$C_8$alkoxy, $C_3$-$C_8$alkoxy interrupted by oxygen; cyclohexyloxy, $C_2$-$C_{12}$alkenyloxy, phenoxy, benzyloxy, chloro, bromo, $C_2$-$C_8$alkanoyloxy or benzoyloxy;

$R_5$ is $C_2$-$C_8$alkylene, cyclohexylene or phenylene;

$R_6$ is a direct bond, $C_1$-$C_8$alkylene; or $C_1$-$C_8$alkylene substituted with $C_1$-$C_4$alkyl, $C_2$-$C_8$alkoxycarbonyl, $C_3$-$C_8$alkoxycarbonylalkyl or phenyl;

$R_7$ is a direct bond or

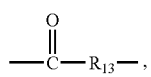

with the proviso that, when $R_7$ is a direct bond and n is 1, $R_6$ is not a direct bond; and with the proviso that, when $R_7$ is

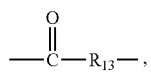

$R_6$ is not a direct bond;
$R_8$ is $C_1$-$C_{12}$alkyl, $C_2$-$C_{12}$alkyl interrupted by oxygen; cyclohexyl, $C_2$-$C_{12}$alkenyl, $C_2$-$C_{12}$alkinyl, benzyl or phenyl,
$R_{11}$ and $R_{12}$ are each independently of the other hydrogen or $C_1$-$C_8$alkyl, or $R_{11}$ and $R_{12}$, together with the carbon atom to which they are bonded, form a cyclohexylidene ring that is unsubstituted or substituted by from 1 to 3 methyl groups,
$R_{13}$ is oxygen or —N($R_{14}$)—,
$R_{14}$ is hydrogen or $C_1$-$C_4$alkyl,
M is sodium or potassium,
m is 1 and
n is 1 or 2.

7. A process according to claim 1 which comprises mixing at a temperature up to 180° C.

8. A process according to claim 1, wherein component (b) is silica or alumina or a mixture of silica and alumina.

9. A process according to claim 1, wherein component (b) is present in an amount of 1 to 80% based on the weight of component (a).

10. A process according to claim 1, wherein component (c) is present in an amount of 0.01 to 10% based on the weight of component (a).

11. A process according to claim 1, comprising in addition, besides components (a) and (b), further additives.

12. A process according to claim 11, comprising as further additives, one or more components selected from the group consisting of pigments, dyes, levelling assistants, dispersants, plasticizers, vulcanization activators, vulcanization accelerators, vulcanizers, charge control agents, adhesion promoters, antioxidants and light stabilizers.

13. A process according to claim 10, comprising, as further additives, phenolic antioxidants, aminic antioxidants, organic phosphites or phosphonites and/or thio-synergists.

14. A compound of the formula Ia

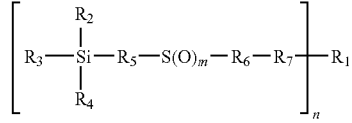
(Ia)

wherein, when n is 1,
$R_1$ is hydrogen, $C_1$-$C_{25}$alkyl, $C_1$-$C_{25}$alkyl substituted with furyl, morpholine, $C_1$-$C_4$dialkylamino, $C_1$-$C_4$trialkylammonium or $M^+$ $^-C_3S$—; $C_2$-$C_{25}$alkyl interrupted by oxygen; $C_5$-$C_{12}$cycloalkyl, $C_2$-$C_{25}$alkenyl, unsubstituted or $C_1$-$C_4$alkyl-substituted phenyl; $C_7$-$C_{12}$phenoxyalkyl, unsubstituted or $C_1$-$C_4$alkyl substituted $C_7$-$C_9$bicycloalkyl;

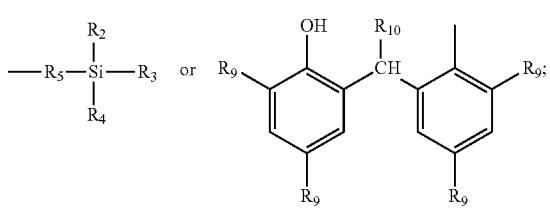

when n is 2,
$R_1$ is $C_1$-$C_{25}$alkylene, $C_1$-$C_{25}$alkylene substituted with $C_1$-$C_4$alkyl; $C_2$-$C_{25}$alkylene substituted with $C_1$-$C_4$alkyl and interrupted by oxygen; $C_2$-$C_{25}$alkylene interrupted by oxygen, sulfur, phenylene or cyclohexylene;

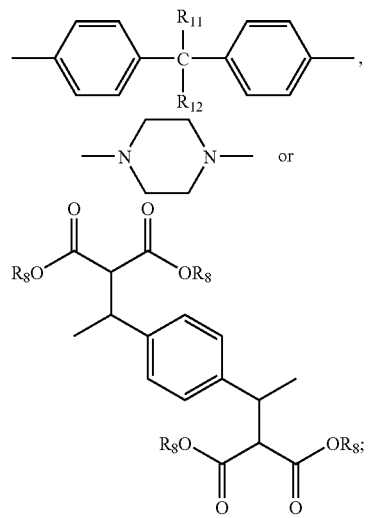

or when $R_6$ and $R_7$ are a direct bond, $R_1$ is

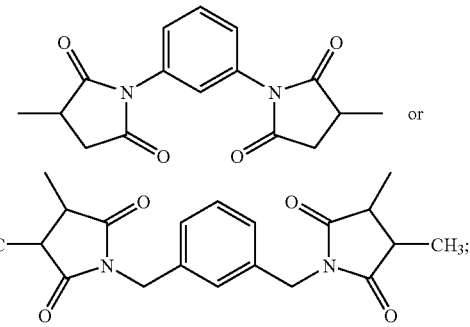

$R_2$, $R_3$ and $R_4$ are each independently of the others $C_1$-$C_{25}$alkyl, $C_2$-$C_{25}$alkyl interrupted by oxygen; $C_5$-$C_{12}$cycloalkyl, $C_2$-$C_{25}$alkenyl, unsubstituted or $C_1$-$C_4$alkyl-substituted phenyl, $C_7$-$C_9$phenylalkyl, $C_1$-$C_{25}$alkoxy, $C_3$-$C_{25}$alkoxy interrupted by oxygen; $C_5$-$C_{12}$cycloalkoxy, $C_2$-$C_{25}$alkenyloxy, unsubstituted or $C_1$-$C_4$alkyl-substituted phenoxy, $C_7$-$C_9$phenylalkoxy, halogen, $C_2$-$C_{25}$alkanoyloxy or unsubstituted or $C_1$-$C_4$alkyl substituted benzoyloxy; with the proviso that at least one of $R_2$, $R_3$ or $R_4$ is $C_1$-$C_{25}$alkoxy, $C_3$-$C_{25}$alkoxy interrupted by oxygen; $C_5$-$C_{12}$cycloalkoxy, $C_2$-$C_{25}$alkenyloxy, unsubstituted or $C_1$-$C_4$alkyl-substituted phenoxy, $C_7$-$C_9$phenylalkoxy, halogen, $C_2$-$C_{25}$alkanoyloxy or unsubstituted or $C_1$-$C_4$alkyl substituted benzoyloxy;

$R_5$ is $C_1$-$C_{25}$alkylene, $C_5$-$C_{12}$cycloalkylene, unsubstituted or $C_1$-$C_4$alkyl substituted phenylene;

$R_6$ is a direct bond, $C_1$-$C_{25}$alkylene substituted with $C_1$-$C_{25}$alkyl, $C_2$-$C_{25}$alkoxycarbonyl, $C_3$-$C_{25}$alkoxycarbonylalkyl or phenyl;

$R_7$ is a direct bond or

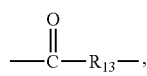

with the proviso that, when $R_7$ is a direct bond and n is 1, $R_6$ is not a direct bond; and with the proviso that, when $R_7$ is

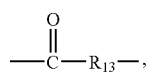

$R_6$ is not a direct bond;

$R_8$ is $C_1$-$C_{25}$alkyl, $C_2$-$C_{25}$alkyl interrupted by oxygen; $C_5$-$C_{12}$cycloalkyl, $C_2$-$C_{25}$alkenyl, $C_2$-$C_{25}$alkinyl, $C_7$-$C_9$phenylalkyl, unsubstituted or $C_1$-$C_4$alkyl-substituted phenyl, $R_9$ is $C_1$-$C_5$alkyl, $R_{10}$ is hydrogen or $C_1$-$C_4$alkyl, $R_{11}$ and $R_{12}$ are each independently of the other hydrogen, $CF_3$, $C_1$-$C_{12}$alkyl or phenyl, or $R_{11}$ and $R_{12}$, together with the carbon atom to which they are bonded, form a $C_5$-$C_8$-cycloalkylidene ring that is unsubstituted or substituted by from 1 to 3 $C_1$-$C_4$alkyl groups, $R_{13}$ is oxygen or —$N(R_{14})$—, $R_{14}$ is hydrogen or $C_1$-$C_{12}$alkyl, M is sodium, potassium or ammonium, m is 1 or 2 and n is 1 or 2; or an oligomeric hydrolysis product of the compound of the formula Ia.

15. A compound according to claim 14, wherein
when n is 1,
$R_1$ is hydrogen, $C_1$-$C_{18}$alkyl, $C_1$-$C_4$alkyl substituted with furyl, morpholine, $C_1$-$C_4$dialkylamino, $C_1$-$C_4$trialkylammonium or $M^+$ $^-O_3S$—; $C_2$-$C_6$alkyl interrupted by oxygen; cyclohexyl, $C_4$-$C_{10}$alkenyl, phenyl; $C_7$-$C_9$phenoxyalkyl, unsubstituted or $C_1$-$C_4$alkyl substituted $C_7$-$C_9$bicycloalkyl; or

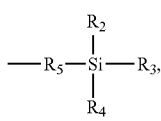

when n is 2,
$R_1$ is $C_2$-$C_6$alkylene, $C_2$-$C_4$alkylene substituted with methyl; $C_4$-$C_8$alkylene substituted with methyl and interrupted by oxygen; $C_4$-$C_8$alkylene interrupted by oxygen;

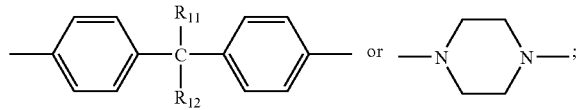

$R_2$, $R_3$ and $R_4$ are each independently of the others $C_1$-$C_4$alkyl or $C_1$-$C_4$alkoxy; with the proviso that at least one of $R_2$, $R_3$ or $R_4$ is $C_1$-$C_4$alkoxy;

$R_5$ is $C_2$-$C_4$alkylene, $R_6$ is $C_1$-$C_3$alkylene substituted with methyl, $C_2$-$C_3$alkoxycarbonyl, $C_3$-$C_6$alkoxycarbonylalkyl or phenyl;

$R_7$ is

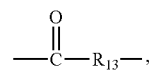

$R_{11}$ and $R_{12}$ are each independently of the other hydrogen or $C_1$-$C_4$alkyl, $R_{13}$ is oxygen or —$N(R_{14})$—, $R_{14}$ is hydrogen, M is potassium, m is 1 and n is 1 or 2; or an oligomeric hydrolysis product of the compound of the formula Ia.

16. A composition comprising
a) a rubber susceptible to oxidative, thermal, dynamic light-induced and/or ozone-induced degradation,
b) a white reinforcing filler and
c) a coupling agent of the formula Ia according to claim 14.

17. A process for ensuring the coupling of a white reinforcing filler to rubber compositions reinforced by a white filler, which comprises incorporating into the rubber at least one coupling agent of the formula Ia according to claim 14 and then vulcanizing the composition.

18. A process for the manufacture of a filled rubber compound with improved processability which comprises mixing in one-step
a) a rubber,
b) a white reinforcing filler and
c) a coupling agent of the formula I

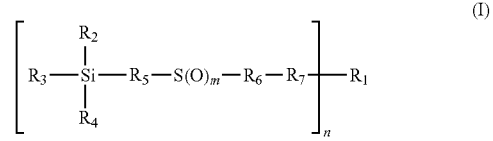

wherein
n is 1;
m is 0, 1 or 2;
$R_6$ and $R_7$ are a direct bond;

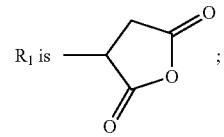

$R_2$, $R_3$ and $R_4$ are each independently of the others $C_1$-$C_{25}$alkyl, $C_2$-$C_{25}$alkyl interrupted by oxygen; $C_5$-$C_{12}$cycloalkyl, $C_2$-$C_{25}$alkenyl, unsubstituted or $C_1$-$C_4$alkyl-substituted phenyl, $C_7$-$C_9$phenylalkyl, $C_1$-$C_{25}$alkoxy, $C_3$-$C_{25}$alkoxy interrupted by oxygen; $C_5$-$C_{12}$cycloalkoxy, $C_2$-$C_{25}$alkenyloxy, unsubstituted or $C_1$-$C_4$alkyl-substituted phenoxy, $C_7$-$C_9$phenylalkoxy, halogen, $C_2$-$C_{25}$alkanoyloxy or unsubstituted or $C_1$-$C_4$alkyl substituted benzoyloxy; or at least two of $R_2$, $R_3$ and $R_4$ are —O-$R_{15}$-O-; or $R_2$ is additionally

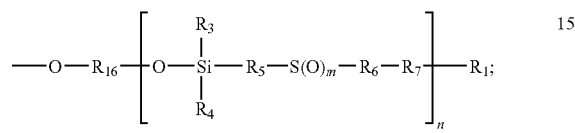

or $R_3$ is additionally

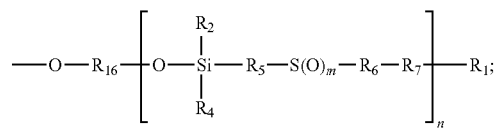

or $R_4$ is additionally

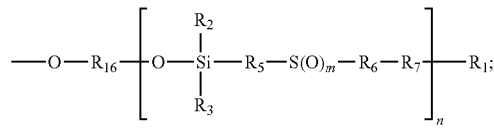

with the proviso that at least one of $R_2$, $R_3$ or $R_4$ is $C_1$-$C_{25}$alkoxy, $C_3$-$C_{25}$alkoxy interrupted by oxygen; $C_5$-$C_{12}$cycloalkoxy, $C_2$-$C_{25}$alkenyloxy, unsubstituted or $C_1$-$C_4$alkyl-substituted phenoxy, $C_7$-$C_9$phenylalkoxy, halogen, $C_2$-$C_{25}$alkanoyloxy or unsubstituted or $C_1$-$C_4$alkyl substituted benzoyloxy;

$R_5$ is $C_1$-$C_{25}$alkylene, $C_5$-$C_{12}$cycloalkylene, unsubstituted or $C_1$-$C_4$alkyl substituted phenylene;

$R_{15}$ is $C_1$-$C_{25}$alkylene or $C_1$-$C_{25}$alkylene substituted with $C_1$-$C_{25}$alkyl;

$R_{16}$ is $C_1$-$C_{25}$alkylene or $C_1$-$C_{25}$alkylene substituted with $C_1$-$C_{25}$alkyl;

or an oligomeric hydrolysis product of the compound of formula I.

19. A process for the manufacture of a filled rubber compound with improved processability which comprises mixing in one-step
a) a rubber,
b) a white reinforcing filler and
c) a coupling agent selected from the group consisting of formulae (165), (166), (167), (169)-(179), (181), (183), (184), (185), (190), (197)-(220) and (221)

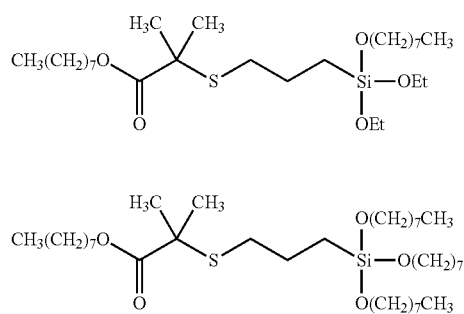

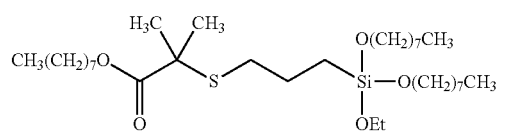

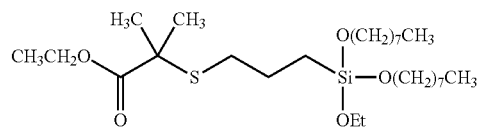

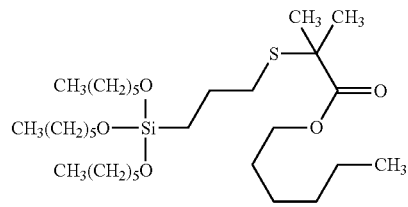

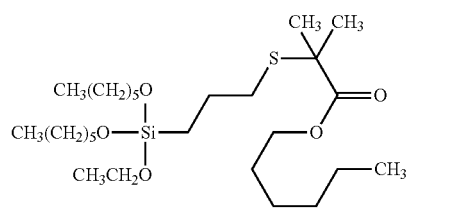

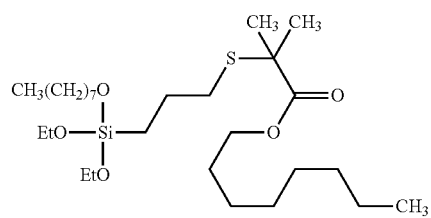

-continued
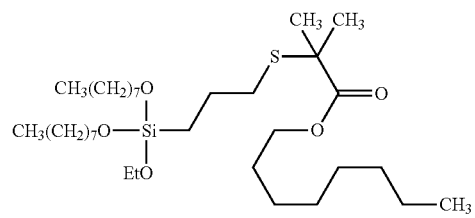
(174)
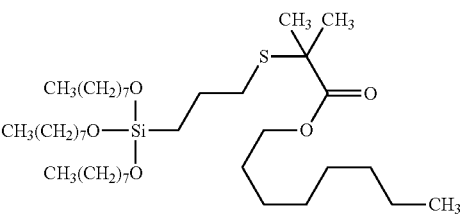
(175)
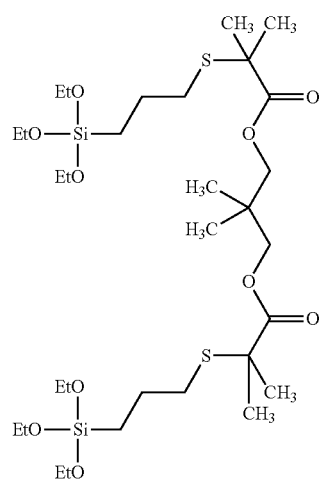
(176)
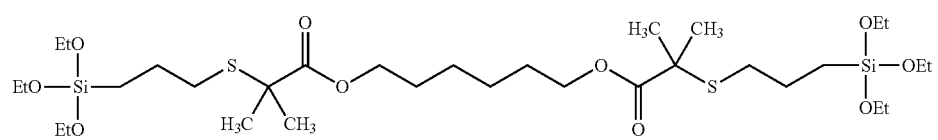
(177)
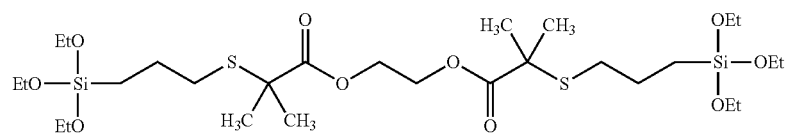
(178)
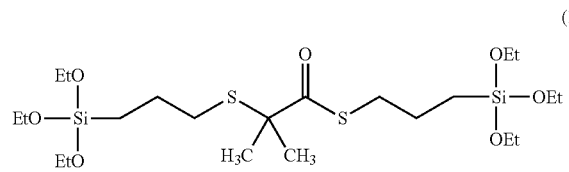
(179)
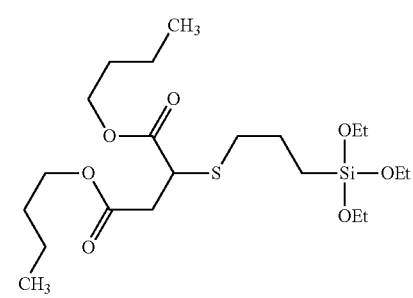
(181)
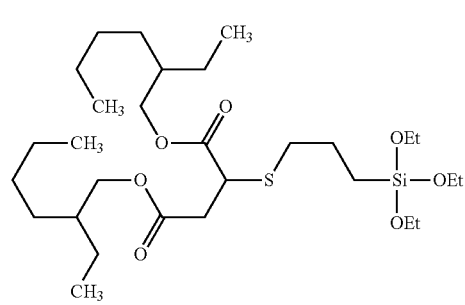
(183)

(184)
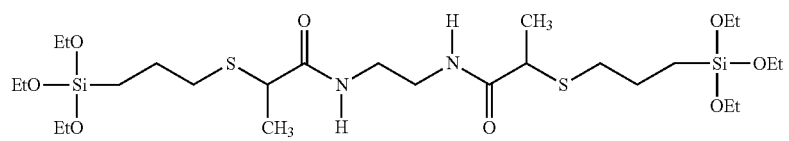
(185)
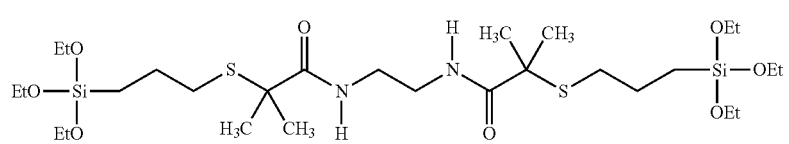
(190)
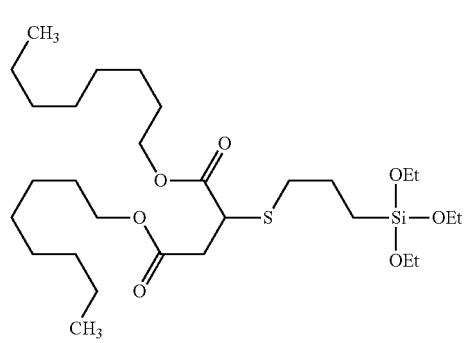
(197)
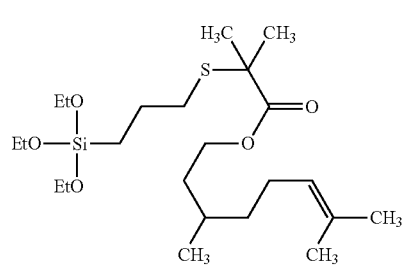
(198)
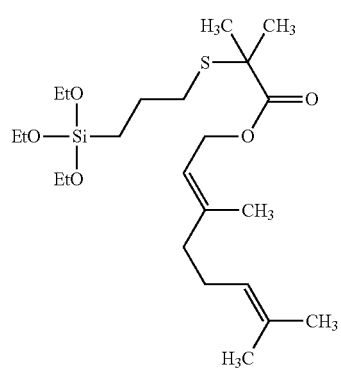
(199)
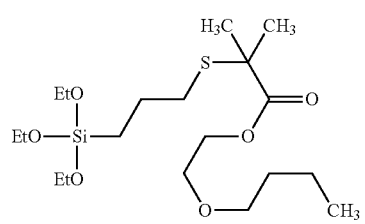
(200)
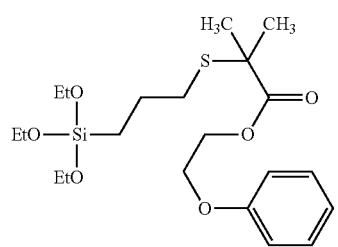
(201)
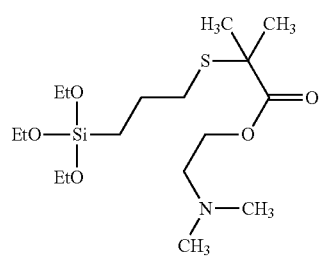
(202)
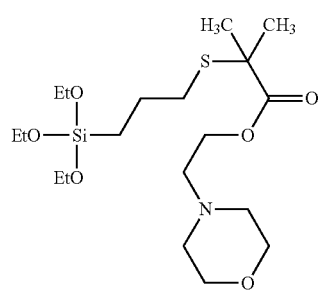
(203)
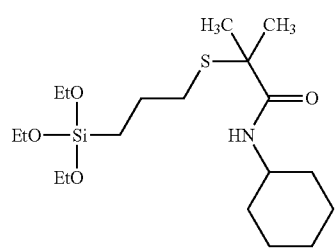

-continued
(204) 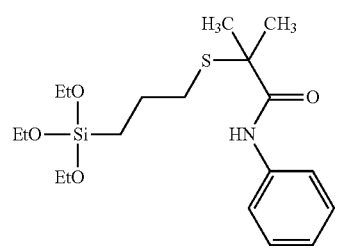
(205) 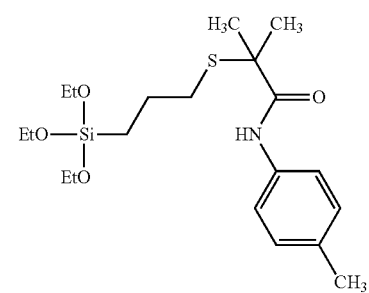
(206) 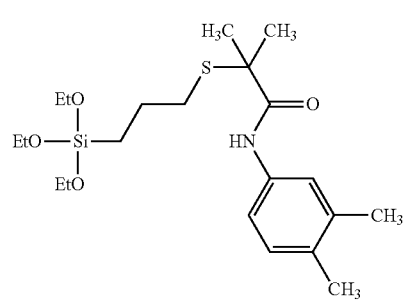
(207) 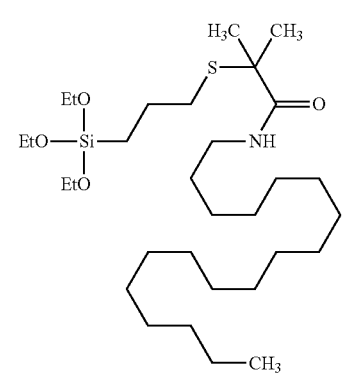
(208) 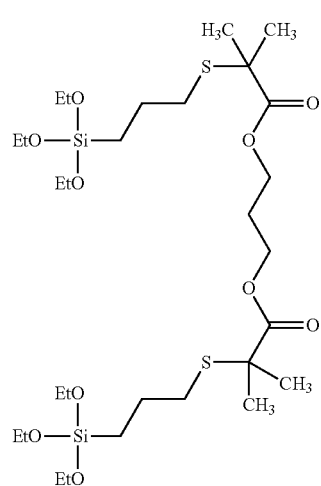
(209) 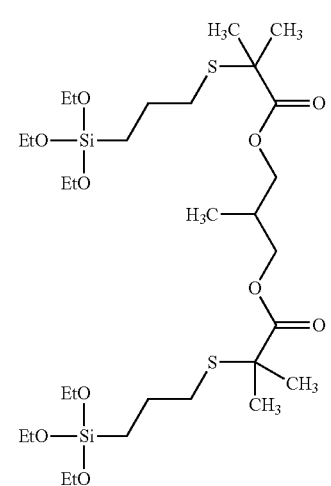
(210) 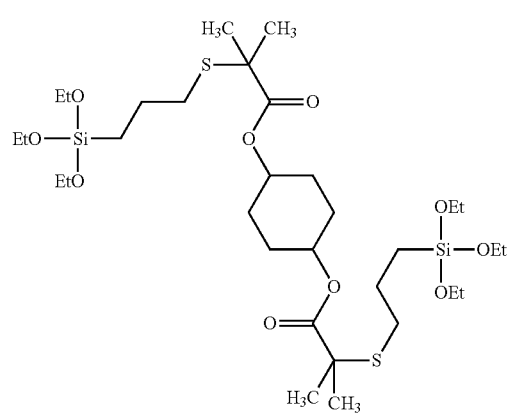
(211) 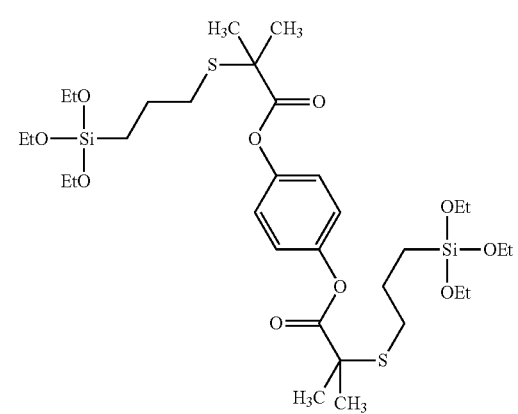

-continued
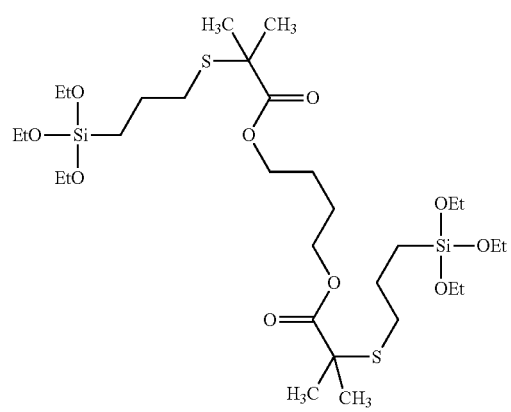
(212)
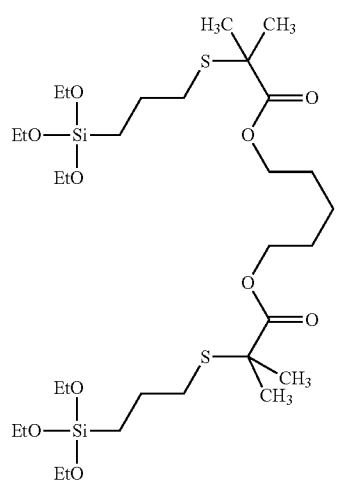
(213)
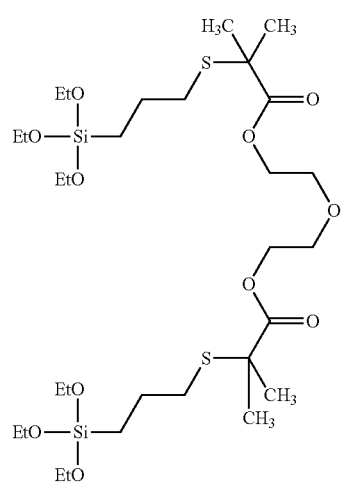
(214)
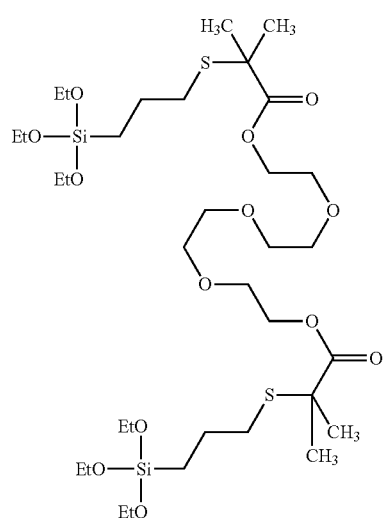
(215)
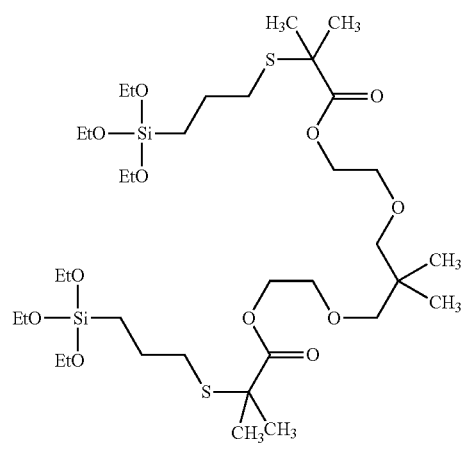
(216)
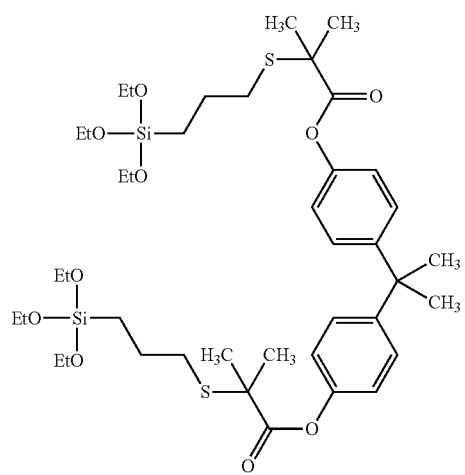
(217)

-continued
(218)
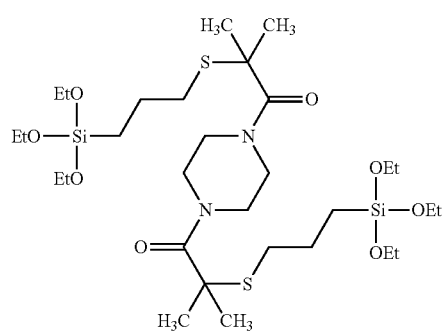
(219)
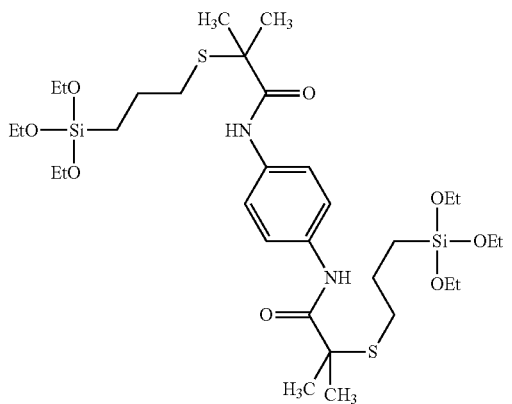
(220)
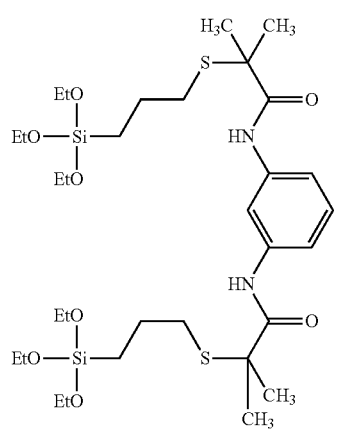
(221)
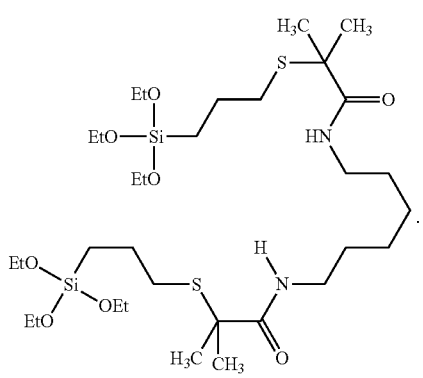
* * * * *